United States Patent
Di Carlo et al.

(10) Patent No.: US 12,370,538 B2
(45) Date of Patent: Jul. 29, 2025

(54) PARTICLE-DROP STRUCTURES AND METHODS FOR MAKING AND USING THE SAME

(71) Applicant: THE REGENTS OF THE UNIVERSITY OF CALIFORNIA, Oakland, CA (US)

(72) Inventors: Dino Di Carlo, Los Angeles, CA (US); Chueh-Yu Wu, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 19/030,466

(22) Filed: Jan. 17, 2025

(65) Prior Publication Data

US 2025/0161932 A1 May 22, 2025

Related U.S. Application Data

(63) Continuation of application No. 18/901,981, filed on Sep. 30, 2024, now Pat. No. 12,239,973, which is a
(Continued)

(51) Int. Cl.
*B01L 3/02* (2006.01)
*B01L 3/00* (2006.01)
(Continued)

(52) U.S. Cl.
CPC ....... *B01L 3/0262* (2013.01); *B01L 3/502715* (2013.01); *B01L 3/502784* (2013.01);
(Continued)

(58) Field of Classification Search
CPC ............. B01L 3/0262; B01L 3/502715; B01L 3/502784; B01L 2300/021;
(Continued)

(56) References Cited

U.S. PATENT DOCUMENTS 5,583,162 A 12/1996 Li et al.
6,190,702 B1 2/2001 Takada et al.
(Continued)

FOREIGN PATENT DOCUMENTS

CA 3005385 A1 11/2019
CN 105764490 A 7/2016
(Continued)

OTHER PUBLICATIONS

Lee "Effects of the poly(ethylene glycol) hydrogel crosslinking mechanism on protein release" Biomater Sci. Mar. 2016 ; 4(3): 405-411. doi:10.1039/c5bm00256g. (Year: 2016).*
(Continued)

*Primary Examiner* — Jennifer Wecker
*Assistant Examiner* — Jonathan Bortoli
(74) *Attorney, Agent, or Firm* — VISTA IP LAW GROUP LLP

(57) ABSTRACT

Sub-millimeter scale three-dimensional (3D) structures are disclosed with customizable chemical properties and/or functionality. The 3D structures are referred to as drop-carrier particles. The drop-carrier particles allow the selective association of one solution (i.e., a dispersed phased) with an interior portion of each of the drop-carrier particles, while a second non-miscible solution (i.e., a continuous phase) associates with an exterior portion of each of the drop-carrier particles due to the specific chemical and/or physical properties of the interior and exterior regions of the drop-carrier particles. The combined drop-carrier particle with the dispersed phase contained therein is referred to as a particle-drop. The selective association results in compartmentalization of the dispersed phase solution into sub-microliter-sized volumes contained in the drop-carrier particles. The compartmentalized volumes can be used for
(Continued)

single-molecule assays as well as single-cell, and other single-entity assays.

19 Claims, 32 Drawing Sheets

Related U.S. Application Data continuation of application No. 18/161,322, filed on Jan. 30, 2023, now Pat. No. 12,233,407, which is a continuation of application No. 16/550,105, filed on Aug. 23, 2019, now Pat. No. 11,590,489, which is a continuation-in-part of application No. PCT/US2018/019486, filed on Feb. 23, 2018.

(60) Provisional application No. 62/463,272, filed on Feb. 24, 2017.

(51) Int. Cl.
 *C12N 1/04* (2006.01)
 *C12N 5/071* (2010.01)
 *C12N 5/0783* (2010.01)
 *C12Q 1/6806* (2018.01)
 *G01N 33/543* (2006.01)

(52) U.S. Cl.
 CPC ............ *C12N 1/04* (2013.01); *C12N 5/0625* (2013.01); *C12N 5/0636* (2013.01); *C12Q 1/6806* (2013.01); *G01N 33/5432* (2013.01); *B01L 2300/021* (2013.01); *B01L 2300/0816* (2013.01); *B01L 2300/0877* (2013.01); *B01L 2300/0896* (2013.01)

(58) Field of Classification Search
 CPC ..... B01L 2300/0816; B01L 2300/0877; B01L 2300/0896; C12N 1/04; C12N 5/0625; C12N 5/0636; C12Q 1/6806; G01N 33/5432
 See application file for complete search history.

(56) References Cited

U.S. PATENT DOCUMENTS

| | | | |
|---|---|---|---|
| 6,391,288 B1 | 5/2002 | Miyazawa et al. |
| 6,806,058 B2 | 10/2004 | Jesperson et al. |
| 7,129,091 B2 | 10/2006 | Ismagilov et al. |
| 7,522,280 B2 | 11/2009 | Holliger et al. |
| 7,622,280 B2 | 11/2009 | Holliger et al. |
| 7,901,939 B2 | 3/2011 | Ismagliov et al. |
| 8,658,430 B2 | 2/2014 | Miller et al. |
| 8,889,083 B2 | 11/2014 | Ismagilov et al. |
| 9,007,433 B2 | 4/2015 | Ozcan et al. |
| 9,029,085 B2 | 5/2015 | Agresti et al. |
| 9,057,702 B2 | 6/2015 | Ozcan et al. |
| 9,816,133 B2 | 11/2017 | Baroud et al. |
| 10,105,703 B2 | 10/2018 | Ismagilov et al. |
| 10,118,174 B2 | 11/2018 | Ismagilov et al. |
| 10,144,911 B2 | 12/2018 | Di Carlo et al. |
| 10,151,429 B2 | 12/2018 | Weitz et al. |
| 10,221,437 B2 | 3/2019 | Weitz et al. |
| 10,562,028 B2 | 2/2020 | Ismagilov et al. |
| 10,668,471 B2 | 6/2020 | Ismagilov et al. |
| 10,683,524 B2 | 6/2020 | Weitz et al. |
| 11,060,541 B2 | 7/2021 | Di Carlo et al. |
| 11,104,961 B2 | 8/2021 | Fontanez et al. |
| 11,278,881 B2 | 3/2022 | Di Carlo |
| 11,512,337 B2 | 11/2022 | Fontanez et al. |
| 11,590,489 B2 | 2/2023 | Di Carlo et al. |
| 11,773,452 B2 | 10/2023 | Fontanez et al. |
| 11,827,936 B2 | 11/2023 | Fontanez et al. |
| 11,866,782 B2 | 1/2024 | Kiani |
| 11,976,325 B2 | 5/2024 | Meltzer |
| 2005/0079510 A1 | 4/2005 | Berka et al. |
| 2006/0154067 A1 | 7/2006 | Cooper et al. |
| 2007/0105972 A1 | 5/2007 | Doyle et al. |
| 2008/0213593 A1 | 9/2008 | Bala Subramaniam et al. |
| 2010/0099048 A1 | 4/2010 | Thomas et al. |
| 2011/0033547 A1 | 2/2011 | Kjems |
| 2011/0091512 A1 | 4/2011 | Li |
| 2011/0106220 A1 | 5/2011 | DeGiorgio et al. |
| 2011/0112603 A1 | 5/2011 | DeGiorgio et al. |
| 2012/0326104 A1 | 12/2012 | Kwon et al. |
| 2013/0157351 A1 | 6/2013 | Ozcan et al. |
| 2014/0127290 A1 | 5/2014 | He et al. |
| 2014/0127305 A1 | 5/2014 | Ortac et al. |
| 2014/0178252 A1 | 6/2014 | Hatch et al. |
| 2014/0230909 A1 | 8/2014 | Di et al. |
| 2014/0342373 A1 | 11/2014 | Viovy et al. |
| 2015/0225777 A1 | 8/2015 | Hindson et al. |
| 2015/0298091 A1* | 10/2015 | Weitz .................. B01F 33/3011 506/28 |
| 2015/0299784 A1 | 10/2015 | Fan et al. |
| 2016/0158755 A1 | 6/2016 | Jeon et al. |
| 2016/0231324 A1 | 8/2016 | Zhao et al. |
| 2016/0289740 A1 | 10/2016 | Fu et al. |
| 2017/0175174 A1* | 6/2017 | Chiu ...................... G01N 21/47 |
| 2017/0368224 A1 | 12/2017 | Griffin et al. |
| 2018/0179590 A1* | 6/2018 | Belgrader .............. C12Q 1/683 |
| 2018/0266452 A1 | 9/2018 | Di Carlo et al. |
| 2019/0009274 A1 | 1/2019 | Novak |
| 2019/0381497 A1 | 12/2019 | Di Carlo et al. |
| 2021/0214721 A1 | 7/2021 | Fontanez et al. |
| 2021/0214763 A1 | 7/2021 | Fontanez et al. |
| 2021/0214769 A1 | 7/2021 | Fontanez et al. |
| 2021/0214792 A1 | 7/2021 | Fontanez et al. |
| 2021/0214802 A1 | 7/2021 | Fontanez et al. |
| 2021/0215591 A1 | 7/2021 | Fontanez et al. |
| 2021/0268465 A1 | 9/2021 | Di Carlo et al. |
| 2021/0292490 A1 | 9/2021 | Di Carlo et al. |
| 2021/0332432 A1 | 10/2021 | Kiani |
| 2021/0340596 A1 | 11/2021 | Meltzer et al. |
| 2021/0354121 A1 | 11/2021 | Di Carlo et al. |
| 2021/0381064 A1 | 12/2021 | Fontanez et al. |
| 2021/0403649 A1 | 12/2021 | Sheikhi et al. |
| 2022/0017892 A1 | 1/2022 | Meltzer et al. |
| 2022/0135966 A1 | 5/2022 | Meltzer |
| 2022/0233413 A1 | 7/2022 | Di Carlo et al. |
| 2022/0235416 A1 | 7/2022 | Fontanez et al. |
| 2022/0267761 A1 | 8/2022 | Fontanez et al. |
| 2022/0372233 A1 | 11/2022 | Xue et al. |
| 2022/0372470 A1 | 11/2022 | Fontanez et al. |
| 2022/0372567 A1 | 11/2022 | Meltzer et al. |
| 2022/0380856 A1 | 12/2022 | Meltzer |
| 2022/0403472 A1 | 12/2022 | Fontanez et al. |
| 2023/0002807 A1 | 1/2023 | Godfrey et al. |
| 2023/0008992 A1 | 1/2023 | Kiani et al. |
| 2023/0018158 A1 | 1/2023 | Kugler et al. |
| 2023/0019117 A1 | 1/2023 | Kiani et al. |
| 2023/0141825 A1 | 5/2023 | Fontanez et al. |
| 2023/0173449 A1 | 6/2023 | De Rutte et al. |
| 2023/0420078 A1 | 12/2023 | Fontanez |
| 2024/0043940 A1 | 2/2024 | Fontanez et al. |
| 2024/0117423 A1 | 4/2024 | Meltzer |
| 2024/0132958 A1 | 4/2024 | Kiani |
| 2024/0203531 A1 | 6/2024 | Agam et al. |
| 2024/0279648 A1 | 8/2024 | Meltzer |

FOREIGN PATENT DOCUMENTS

| | | |
|---|---|---|
| CN | 112867475 B | 3/2024 |
| EP | 3585364 A1 | 1/2020 |
| EP | 3838268 A1 | 6/2021 |
| KR | 20140063888 A | 5/2014 |
| WO | WO-2004103351 A1 | 12/2004 |
| WO | WO-2010042943 A1 | 4/2010 |
| WO | WO-2012116014 A1 | 8/2012 |
| WO | WO-2013049404 A2 | 4/2013 |
| WO | WO 2014/146025 | 9/2014 |
| WO | WO 2015/164212 A1 | 10/2015 |
| WO | WO 2015/164212 A9 | 10/2015 |
| WO | WO 2015/200541 A1 | 12/2015 |

(56) References Cited

FOREIGN PATENT DOCUMENTS

| | | |
|---|---|---|
| WO | WO 2016/018678 | 2/2016 |
| WO | WO 2017/059367 | 4/2017 |
| WO | WO-2017087693 A2 | 5/2017 |
| WO | WO 2018/140966 A1 | 8/2018 |
| WO | WO-2018156935 A1 | 8/2018 |
| WO | WO-2020037214 A1 | 2/2020 |
| WO | WO-2020069298 A1 | 4/2020 |
| WO | WO-2020146031 A1 | 7/2020 |
| WO | WO-2020227321 A1 | 11/2020 |
| WO | WO-2021146166 A1 | 7/2021 |
| WO | WO-2021146168 A1 | 7/2021 |
| WO | WO-2021146183 A1 | 7/2021 |
| WO | WO-2021146184 A1 | 7/2021 |
| WO | WO-2021146187 A1 | 7/2021 |
| WO | WO-2021188500 A1 | 9/2021 |
| WO | WO-2021262312 A2 | 12/2021 |
| WO | WO-2022015970 A1 | 1/2022 |
| WO | WO-2022031857 A2 | 2/2022 |
| WO | WO-2021262312 A3 | 3/2022 |
| WO | WO-2022031857 A3 | 4/2022 |
| WO | WO-2022098726 A1 | 5/2022 |
| WO | WO-2022098736 A1 | 5/2022 |
| WO | WO-2022159896 A2 | 7/2022 |
| WO | WO-2022221391 A1 | 10/2022 |
| WO | WO-2022245825 A1 | 11/2022 |
| WO | WO-2022245826 A1 | 11/2022 |
| WO | WO-2022245827 A1 | 11/2022 |
| WO | WO-2022245830 A1 | 11/2022 |
| WO | WO-2022245868 A1 | 11/2022 |
| WO | WO-2022251445 A1 | 12/2022 |
| WO | WO-2023278537 A2 | 1/2023 |
| WO | WO-2023283408 A1 | 1/2023 |
| WO | WO-2023287957 A1 | 1/2023 |
| WO | WO-2023287980 A1 | 1/2023 |
| WO | WO-2023250418 A2 | 12/2023 |
| WO | WO-2024077114 A1 | 4/2024 |
| WO | WO-2024137573 A1 | 6/2024 |

OTHER PUBLICATIONS

Amini, Hamed et al. Engineering Fluid Flow Using Sequenced Microstructures. Nature Communications vol. 4,1: 1826, pp. 1-8 (2013).

Bong, Ki Wan et al. Lock Release Lithography for 3D and Composite Microparticles. Lab on a Chip vol. 9,7: pp. 863-866 (2009).

Boyd, Darryl A et al. Design and Fabrication of Uniquely Shaped Thiol-ene Microfibers Using a Two-stage Hydrodynamic Focusing Design. Lab on a Chip vol. 13,15: pp. 3105-3110 (2013).

Cao, Jiaojie, et al., Controlling sol-gel polymerization to create bowl-shaped polysilsesquioxane particles with a kippah structure. Polymer 54(10):2493-2497 (2013).

Chang, Lei, et al., Single molecule enzyme-linked immunosorbent assays: theoretical considerations. Journal of Immunological Methods 378(1-2):102-115 (2012).

De Rutte, Joseph, et al., Massively parallel encapsulation of single cells with structured microparticles and secretion-based flow sorting. BioRxiv https://www.biorxiv.org/content/10.1101/2020.03.09.984245v2 (2020).

De Rutte, Joseph, et al., Scalable High-Throughput Production of Modular Microgels for In Situ Assembly of Microporous Tissue Scaffolds. Advanced Functional Materials :1-10 (2019).

Dendukuri, Dhananjay et al. Continuous-Flow Lithography For High-Throughput Microparticle Synthesis. Nature Materials vol. 5,5: 365-369 (2006).

Dendukuri, Dhananjay et al. Stop-flow Lithography in a Microfluidic Device. Lab on a Chip vol. 7,7: pp. 818-828 (2007).

Di Carlo Laboratory Microfluidic Biotechnology. UCLA Software, uFlow, A computer-aided design (CAD) tool for the rational design of inertial flows. Accessed May 28, 2024. p. 1. Retrieved from Internet URL: https://www.biomicrofluidics.com/software.

Dimova, Rumiana et al., Lipid membranes in contact with aqueous phases of polymer solutions, Soft Matter 8:6409-6415 (2012).

Ding et al., Sensitive and predictable separation of microfluidic droplets by size using in-line passive filter. Biomicrofluidics 11(1):014114 (2017).

Duncanson, Wynter J, et al., Microfluidic Synthesis Of Advanced Microparticles For Encapsulation And Controlled Release. Lab on a Chip 12(12):2135-2145 (2012).

Edd, Jon F, et al., Controlled Encapsulation Of Single Cells Into Monodisperse Picoliter Drops. Lab Chip 8(8):1262-1264 (2008).

Fan, Christina H et al. Expression Profiling. Combinatorial Labeling of Single Cells for Gene Expression Cytometry. Science 347(6222):1258367, pp. 1-10 (2015).

Forciniti, D., et al., Influence of polymer molecular weight and temperature on phase composition in aqueous two-phase systems. Fluid Phase Equilibria 61(3):243-262 (1991).

Furukawa, Yuki, et al., Nano- and microsized cubic gel particles from cyclodextrin metal-organic frameworks. Angewandte Chemie 51(42):10566-10569 (2012).

Hackler, Amber L., et al., Off-DNA DNA-Encoded Library Affinity Screening. ACS Combinatorial Science 22(1):25-34 (2019).

Hassanzadeh-Barforoushi, Amin, et al., Static droplet array for culturing single live adherent cells in an isolated chemical microenvironment. Lab on a Chip 18(15):2156-2166 (2018).

Hindson, Benjamin J et al. High-throughput Droplet Digital PCR System for Absolute Quantitation of DNA Copy Number. Analytical Chemistry vol. 83,22: pp. 8604-8610 (2011).

Hu et al.: Microfluidic fabrication of shape-tunable alginate microgels: Effect of size and impact velocity. Carbohydrate Polymers. 120:38-45 (2015).

Hu, Yuandu, et al., Fabrication of shape controllable Janus alginate/pNIPAAm microgels via microfluidics technique and off-chip ionic cross-linking. Langmuir 31(6):1885-1891 (2015).

Huang, Fujian, et al., Two-Photon Lithographic Patterning of DNA-Coated Single-Microparticle Surfaces. Nano Letters 19(1):618-625 (2019).

Kawata, Satoshi, et al., Finer Features for Functional Microdevices. Nature 412(6848):697-698 (2001).

Kc, Pawan, et al., Development and Comparison of Two Immunodisaggregation Based Bioassays for Cell Secretome Analysis. Theranostics 8(2):328-340 (2018).

Kim, Shin-Hyun, et al., Amphiphilic crescent-moon-shaped microparticles formed by selective adsorption of colloids. Journal of the American Chemical Society 133(14):5516-5524 (2011).

Klein, Allon M, et al., Droplet Barcoding for Single-cell Transcriptomics Applied to Embryonic Stem Cells. Cell 161(5):1187-1201 (2015).

Komnatnyy, Vitaly V., Bead-based screening in chemical biology and drug discovery. Chemical Communications 54(50):6759-6771 (2018).

Koyanagi, Keisuke, et al., Sol-Gel Coexisting Phase of Polymer Microgels Triggers Spontaneous Buckling. Langmuir 35(6):2283-2288 (2019).

Liu, Qian, et al., Self-orienting hydrogel micro-buckets as novel cell carriers. Angewandte Chemie 131(2):557-561 (2019).

Long, M Scott, et al., Dynamic microcompartmentation in synthetic cells. Proceedings of the National Academy of Sciences of the United States of America 102(17):5920-5925 (2005).

Ma, Shaohua, et al., Fabrication of microgel particles with complex shape via selective polymerization of aqueous two-phase systems. Small 8(15):2356-2360 (2012).

Min, Nam Gi, et al., Microfluidic Production of Uniform Microcarriers with Multicompartments through Phase Separation in Emulsion Drops. Chemistry of Materials 28(5):1430-1438 (2016).

Novak et al.: Single-Cell Multiplex Gene Detection and Sequencing with Microfluidically Generated Agarose Emulsions. Angewandte Chemie International Edition. 50(2):390-395 (2011).

Novak, Richard, et al., Single-Cell Multiplex Gene Detection and Sequencing with Microfluidically Generated Agarose Emulsions. Angewandte Chemie 50(2): 390-395 (2011).

Nunes, Janine K et al. Fabricating Shaped Microfibers With Inertial Microfluidics. Advanced materials vol. 26,22: pp. 3712-3717 (2014).

Ozawa, Tatsuhiko, et al., Amplification and analysis of cDNA generated from a single cell by 5'-RACE: application to isolation of

(56) References Cited

OTHER PUBLICATIONS antibody heavy and light chain variable gene sequences from single B cells. BioTechniques 40(4):469-478 (2006).
Paulsen, Kevin et al. Optofluidic Fabrication For 3D-Shaped Particles. Nature Communications vol. 6:6976, pp. 1-9 (2015).
Peng, Feifei, et al., A droplet-based microfluidics route to temperature-responsive colloidal molecules. The Journal of Physical Chemistry 123(43):9260-9271 (2019).
Price, Alexander K., et al., hvSABR: Photochemical Dose-Response Bead Screening in Droplets. Analytical Chemistry 88(5):2904-2911 (2016).
Sacanna, S., et al., Lock and key colloids. Nature 464(7288):575-578 (2010).
Schmidt, John J, et al., Hydrogels Used For Cell-Based Drug Delivery. Journal of Biomedical Materials Research Part A 87(4):1113-1122 (2008).
Shah, Rhutesh K., et al., Janus Supraparticles by Induced Phase Separation of Nanoparticles in Droplets. Advanced Materials 21(19):1949-1953 (2009).
Sheikhi, Amir, et al., Microengineered Emulsion-to-Powder Technology for the High-Fidelity Preservation of Molecular, Colloidal, and Bulk Properties of Hydrogel Suspensions. ACS Applied Polymer Materials 1(8):1935-1941 (2019).
Shi, Guixin, et al., Isolation of rare tumor cells from blood cells with buoyant immuno-microbubbles. PLoS One 8(3):e58017 (2013).
Snyder, Steven M., et al., Phase compositions, viscosities, and densities for aqueous two-phase systems composed of polyethylene glycol and various salts at 25 .degree.C. Journal of Chemical & Engineering Data 37(2):268-274 (1992).
Tan, Wei-Heong, et al., Monodisperse Alginate Hydrogel Microbeads for Cell Encapsulation. Advanced Materials 19(18):2696-2701 (2007).
Tees, D.F., et al., A microcantilever device to assess the effect of force on the lifetime of selectin-carbohydrate bonds. Biophysical Journal 80(2):668-682 (2001).
Thangawng, Abel L et al. A Simple Sheath-flow Microfluidic Device for Micro/nanomanufacturing: Fabrication of Hydrodynamically Shaped Polymer Fibers. Lab on a Chip vol. 9,21: pp. 3126-3130 (2009).
Tseng, Derek, et al., Lensfree microscopy on a cellphone. Lab on a Chip 10(14):1787-1792 (2010).
Uspal, William E et al. Engineering Particle Trajectories in Microfluidic Flows Using Particle Shape. Nature Communications vol. 4: 2666, pp. 1-9 (2013).
Van Zee, Mark, et al. High-throughput selection of microalgae based on biomass accumulation rates in production environments using PicoShell Particles. bioRxiv (2021) (preprint published online Feb. 4, 2021).
Vis, Mark, et al., Donnan Potentials in Aqueous Phase-Separated Polymer Mixtures. Langmuir 30(20):5755-5762 (2014).
Wan, Jiandi, et al., Microfluidic-Based Synthesis of Hydrogel Particles for Cell Microencapsulation and Cell-Based Drug Delivery. Polymers 4(2):1084-1108 (2012).
Wang, Baoguo, et al., Fabrication of Monodisperse Toroidal Particles by Polymer Solidification in Microfluidics. Chemphyschem 10(4):641-645 (2009).
Wang, Wei, et al., Hole-shell microparticles from controllably evolved double emulsions. Angewandte Chemie 52(31):8084-8087 (2013).
Wong, Ada Hang-Heng, et al., Drug screening of cancer cell lines and human primary tumors using droplet microfluidics. Scientific Reports 7(1):9109 (2017).
Wu, Chueh-Yu, et al. Monodisperse drops templated by 3D-structured microparticles. Science Advances 6.45:eabb9023 (2020).
Yanagisawa, Miho, et al., Multiple patterns of polymer gels in microspheres due to the interplay among phase separation, wetting, and gelation. Proceedings of the National Academy of Sciences of the United States of America 111(45):15894-15899 (2014).
Yeredla, Nitish, et al., Aqueous Two Phase System Assisted Self-Assembled PLGA Microparticles. Scientific Reports 6:1-8 (2016).
Yuan, Hao, et al., Phase-Separation-Induced Formation of Janus Droplets Based on Aqueous Two-Phase Systems. Macromolecular Chemistry and Physics 218(2):1-8 (2016).
Zhang et al.: Synthesis of shape-controlled particles based on synergistic effect of geometry confinement, double emulsion template, and polymeriation quenching. Microfluid Nanoflued. 12:33-39 (2012).
Zhang, Hong, et al., Microfluidic Production of Biopolymer Microcapsules with Controlled Morphology. Journal of the American Chemical Society 128(37):12205-12210 (2006).
Zhang, Xunan, et al., Hierarchical drug release of pH-sensitive liposomes encapsulating aqueous two phase system. European Journal of Pharmaceutics and Biopharmaceutics 127:177-182 (2018).
Reply to Communication regarding to Rule 71(3) EPC dated Sep. 6, 2024 for EP application 23153240.9, (7 pages).
Decision to Grant dated Sep. 19, 2024 for EP application 23153240.9, (2 pages).
The extended European search report dated Oct. 16, 2024 for EP application 24200492.7, (7 pages).
Ju Hyeon Kim et al., Droplet Microfluidics for Producing Functional Microparticles, Langmuir 2014, 30, 1473-1488.
Wook Park et al., Free-floating amphiphilic picoliter droplet carriers for multiplexed liquid loading in a microfluidic channel, Microfluid Nanofluid (2012) 13:511-518.
Office Action dated Sep. 16, 2024 for U.S. Appl. No. 17/268,954, (22 pages).
Qingquan Zhang et al., Synthesis of shape-controlled particles based on synergistic effect of geometry confinement, double emulsion template, andpolymerization quenching, Microfluid Nanofluid (2012) 12:33-39.
Shaohua Ma et al., Fabrication of Microgel Particles with Complex Shape via Selective Polymerization of Aqueous Two-Phase Systems, Small (2012) 8:15, 2356-2360.
Yuandu Hu et al., Microfluidic fabrication of shape-tunable alginate microgels: Effect of size and impact velocity, Carbohydrate Polymers, (2015) 120, 38-45.
Response to Third Office Action dated Jul. 5, 2024 for Japanese Patent Appl No. 2021-507857, English translations for claims only (8 pages).
Response to the first Examination Report dated Oct. 14, 2024 for Australian Appl No. 2019321593, (143 pages).
Notice of Allowance date Sep. 17, 2024 for Japanese Appl No. 2021-507857, (4 pages).
Notice of Allowance dated Aug. 8, 2024 for U.S. Appl. No. 18/161,322, (16 pages).
Request for Continued Examination dated Oct. 30, 2024 for U.S. Appl. No. 18/161,322, (15 pages).
PCT International Search Report for PCT/US2018/019486, Applicant: The Regents of the University of California, Form PCT/ISA/210 and 220, dated Apr. 20, 2018 (4pages).
PCT Written Opinion of the International Search Authority for PCT/US2018/019486, Applicant: The Regents of the University of California, Form PCT/ISA/237, dated Apr. 20, 2018 (11 pages).
Macosko, E.Z. et al., Highly parallel genome-wide expression profiling of individual cells using nanoliter droplets, Cell. 161, 1202-1214 (2015).
Na, X.M. et al., Biodegradable Microcapsules Prepared by Self-Healing of Porous Microspheres, ACS Macro Letters, 2012, vol. 1, No. 6, abstract; pp. 698-699.
Yin, W. et al., Encapsulation and sustained release from biodegradable microcapsules made by emulsification/freeze drying and spray/freeze drying, Journal of Colloid and Interface Science 336 (2009) 155-161.
Dendukuri, D. et al., Synthesis and Self-Assembly of Amphiphilic Polymeric Microparticles, Langmuir 2007, 23, 4669-4674.
Kang, C.C. et al., Single cell-resolution western blotting, Nature Protocols, vol. 11, No. 8, 1508 (2016).
Mitra, R.D. et al., In situ localized amplification and contact replication of many individual DNA molecules, Nucleic Acids Research, 1999, vol. 27, No. 24, e34.
Peterson, V.M. et al., Multiplexed quantification of proteins and transcripts in single cells, Nature Biotechnology, vol. 35, No. 10, Oct. 2017.

(56) References Cited

OTHER PUBLICATIONS

Plesa, C. et al., Multiplexed gene synthesis in emulsions for exploring protein functional landscapes, Science 359, 343-347 (2018).
Wu, C.Y. et al., Rapid Software-Based Design and Optical Transient Liquid Molding of Microparticles, Adv. Mater. 2015, 27, 7970-7978.
Wu, J. et al., Recent Studies of Pickering Emulsions: Particles Make the Difference, small 2016, 12, No. 34, 4633-4648.
Xu, L. et al., Virtual microfluidics for digital quantification and single-cell sequencing, Nature Methods, vol. 13, No. 9, Nov. 2016, 759.
PCT International Preliminary Report on Patentability (Chapter I of the Patent Cooperation Treaty) for PCT/US2018/019586 Applicant: The Regents of the University of California, Form PCT/IB/326 and 373, dated Sep. 6, 2019 (13 pages).
The extended European search report dated Jan. 23, 2020 in European Patent Application No. 18758232.5 (5pages).
Park, Wook et al., Free-floating amphiphilic picoliter droplet carriers for multiplexed liquid loading in a microfluidic channel, Microfluidic Nanofluid (2012) 13:511-518.
Kim, Ju Hyeon et al., Droplet Microfluidics for Producing Functional Microparticles, Langmuir 2014, 30, 1473-1488.
Wang, Jianmei et al., Droplet Microfluidics for the Production of Microparticles and Nanoparticles, Micromachines 2017, 8, 22; doi:10.3390/mi8010022.
Communication pursuant to Rules 70(2) and 70a(2) EPC dated Feb. 11, 2020 in European Patent Application No. 18758232.5 (1page).
Office Action dated Dec. 10, 2021 for U.S. Appl. No. 17/387,990 (18 pages).
Ghulam Destgeer et al., Fabrication of 3D concentric amphiphilic microparticles to form uniform nanoliter reaction volumes of amplified affinity assays, Lab Chip, 2020, 20, 3503-3514 (Year: 2020).
Kyung Jin Son et al., Microfluidic compartments with sensing microbeads for dynamic monitoring of cytokine and exosome release from single cells, Analyst, 2016, 141, 679-688 (Year: 2016).
Notice of Allowance dated Feb. 1, 2022 for U.S. Appl. No. 17/387,990 (8 pages).
Woo Park et al., Free-floating amphiphilic picoliter droplet carriers for multiplexed liquid loading in a microfluidic channel, Microfluid Nanofluid (2012) 13:511-518.
Jianmei Wang et al., Droplet Microfluidics for the Production of Microparticles and Nanoparticles, Micromachines 2017, 8, 22; doi:10.3390/mi8010022 (23 pages).
Extended European Search Report dated Mar. 19, 2021, for European Patent Application No. EP 21 15 6199 (3 pages).
Communication under Rule 71(3) EPC dated Oct. 8, 2020, for European Patent Application No. 18758232.5-111, (7 pages).
Response to Communication pursuant to Rules 70(2) and 70a(2) EPC and extended European search report and dated Aug. 20, 2020, for European Patent Application No. 18758232.5-111, (89 pages).
Decision to Grant dated Apr. 1, 2021, for European Patent Application No. 18758232.5-111, (2 pages).
Communication pursuant to Article 94(3) EPC dated Jan. 27, 2022, for European Patent Application No. 21156199.8-111, (3 pages).
Response to Communication pursuant to Article 94(3) EPC dated Jun. 8, 2022, for European Patent Application No. 21156199.8-111, (65 pages).
Communication under Rule 71(3) EPC dated Jul. 28, 2022, for European Patent Application No. 21156199.8-111, (7 pages).
The extended European search report dated Jun. 30, 2023 for EP application 23153240.9, (6 pages).
Communication pursuant to Rule 69 EPC-reminder concerning payment of the designation fee (Art. 79(2) EPC) and of the examination fee (Art. 94(1) EPC)—and invitation pursuant to Rule 70a(1) EPC dated Aug. 7, 2023, (2 pages).
Reply to the extended European search report, Communication pursuant to Rule 69 EPC dated Feb. 2, 2024 for EP application 23153240.9, (69 pages).
Communication under Rule 71(3) EPC dated May 6, 2024 for EP application 23153240.9, (97 pages).
Office Action dated Mar. 28, 2024 for U.S. Appl. No. 17/268,954, (59 pages).
Examiner's Interview Summary dated May 23, 2024 for U.S. Appl. No. 17/268,954, (6 pages).
Amendment and Response dated Jun. 28, 2024 for U.S. Appl. No. 17/268,954, (21 pages).
Examination report No. 1 for standard patent application dated Jun. 24, 2024 for Australian App No. 2019321593, (4 pages).
Communication under Rule 71(3) dated Feb. 9, 2024 for 19850668.5, (98 pages).
Reply to the communication about intention to grant a European patent under Rule 71(3) EPC dated Jun. 10, 2024 for European Patent Appl No. 19850668.5, (8 pages).
Decision to Grant dated Jun. 20, 2024 for European Patent Appl No. 19850668.5, (2 pages).
Third Office Action dated Apr. 9, 2024 for Japanese Patent Appl No. 2021-507857, (4 pages).
Examination report No. 2 for standard patent application dated Nov. 14, 2024 for Australian Patent Application No. 2019321593, (7 pages).
Notice of Allowance and Issue Fee dated Dec. 2, 2024 for U.S. Appl. No. 18/161,322, (38 pages).
Response to Examination report No. 2 for standard patent application dated Dec. 5, 2024 for Australian Patent Application No. 2019321593, (2 pages).
Response to Office Action dated Dec. 16, 2024 for U.S. Appl. No. 17/268,954, (19 pages).

* cited by examiner

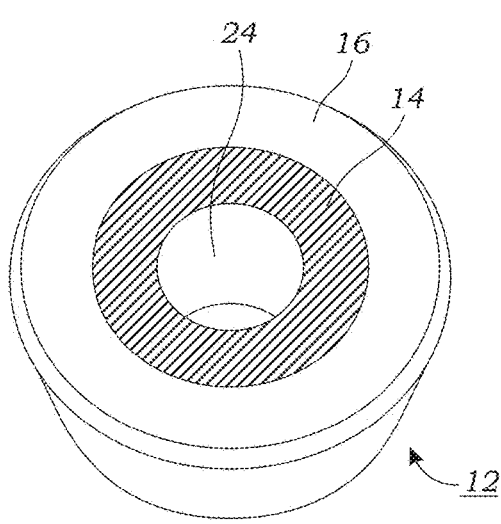 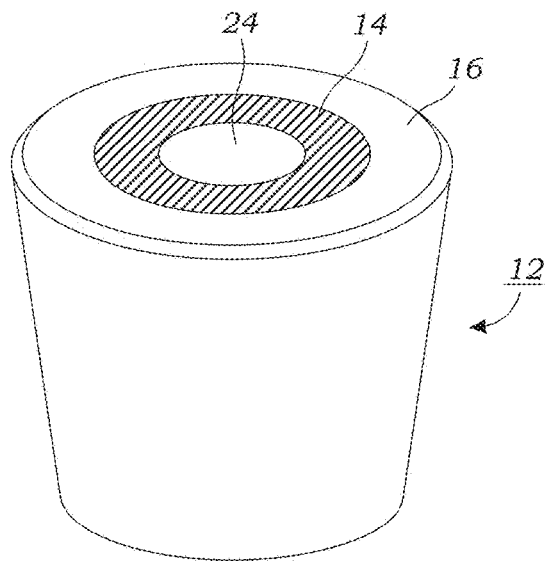
FIG. 9A    FIG. 9B
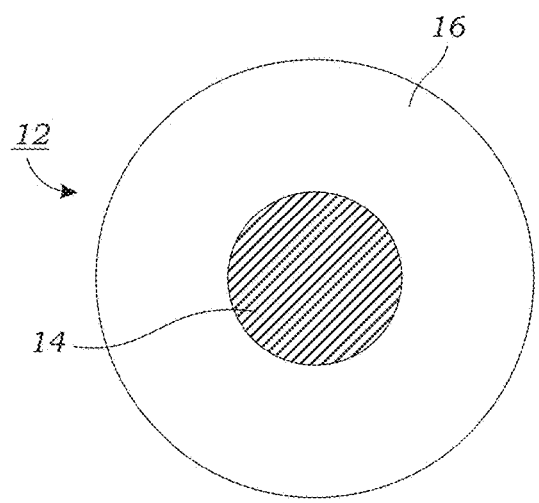 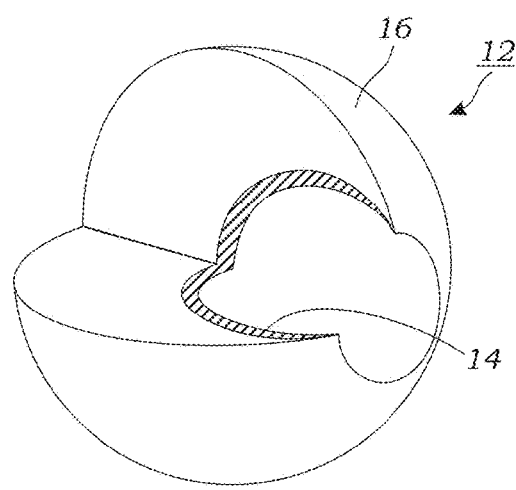
FIG. 10A    FIG. 10B

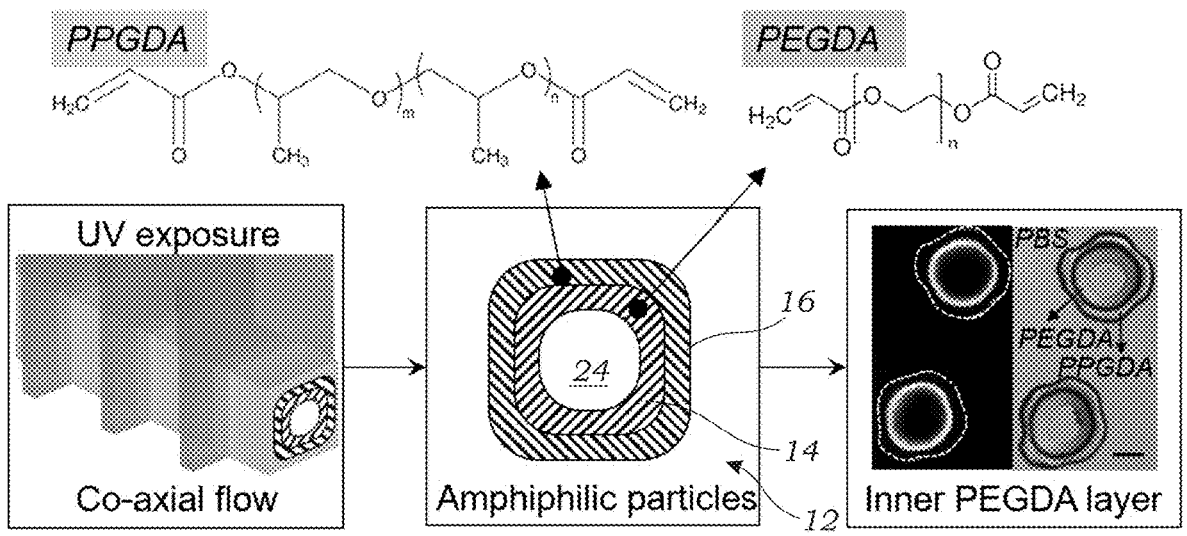
FIG. 20C    FIG. 20D    FIG. 20E
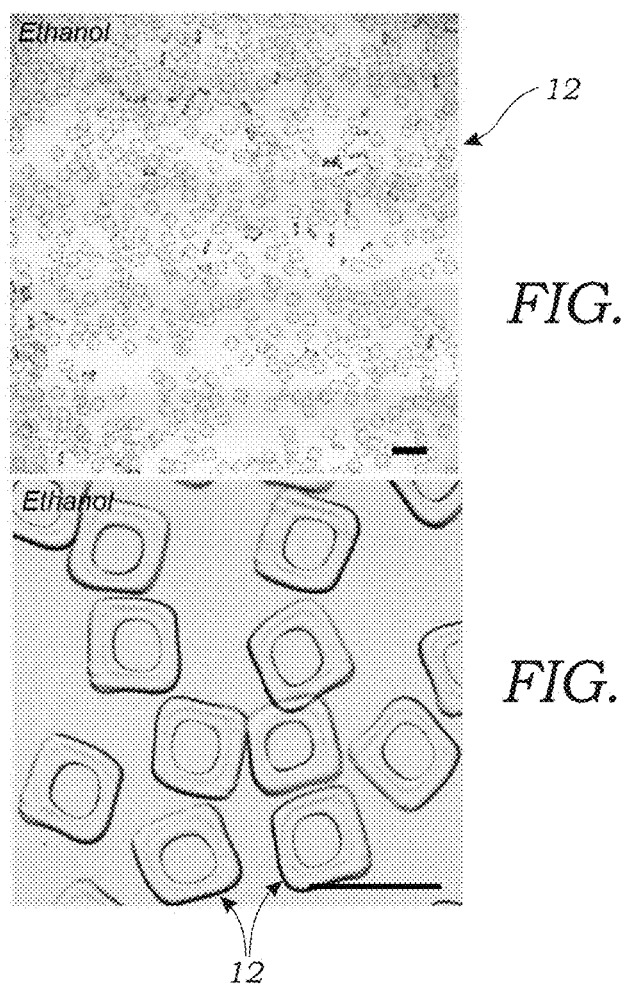
FIG. 20F
FIG. 20G

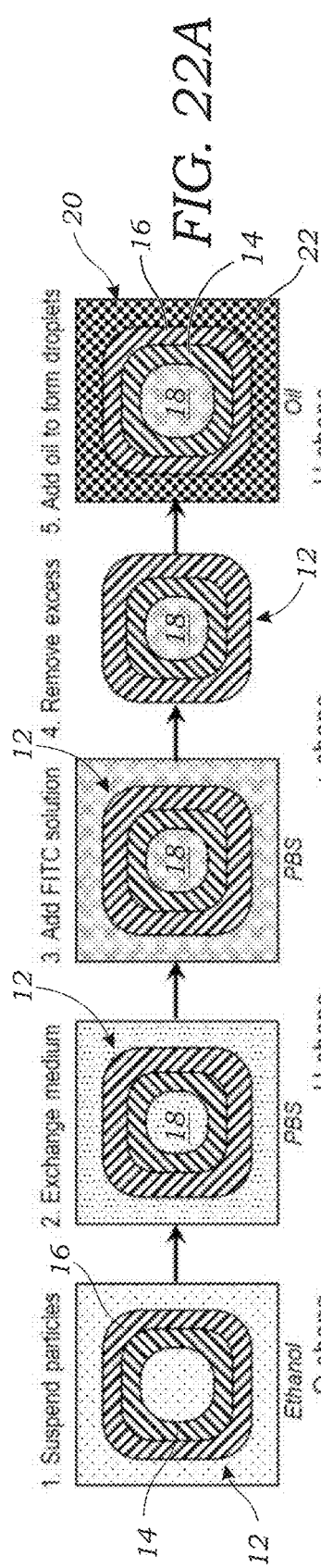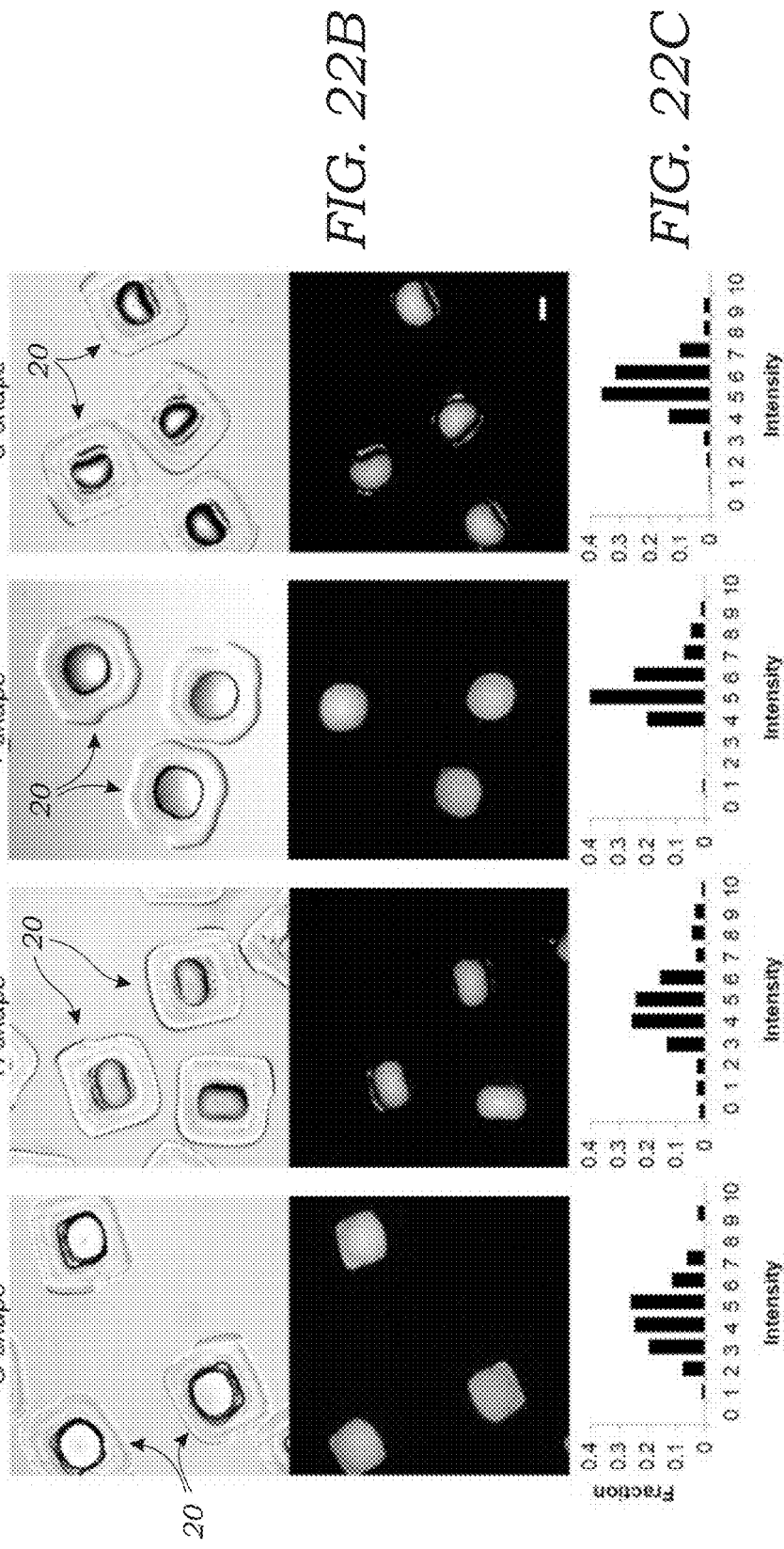
FIG. 22A
FIG. 22B
FIG. 22C

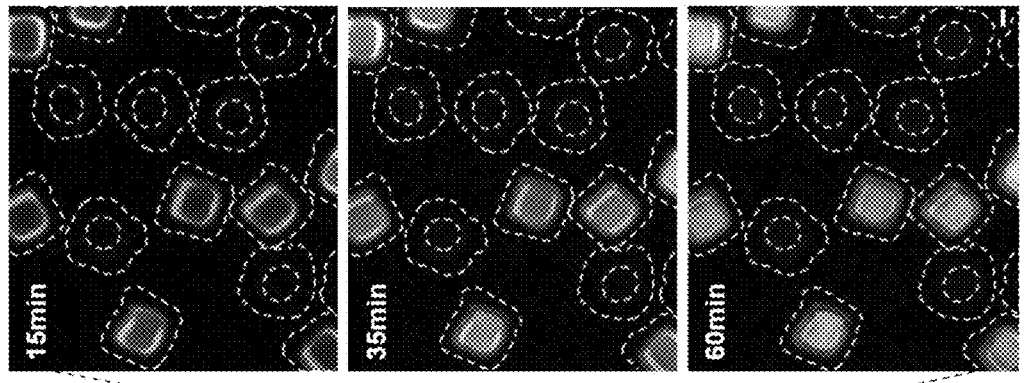
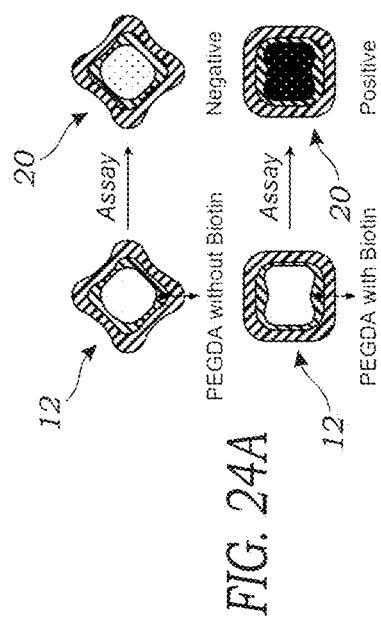
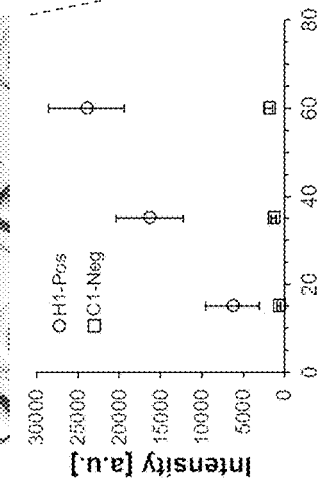
FIG. 24A  FIG. 24B  FIG. 24C  FIG. 24D  FIG. 24E

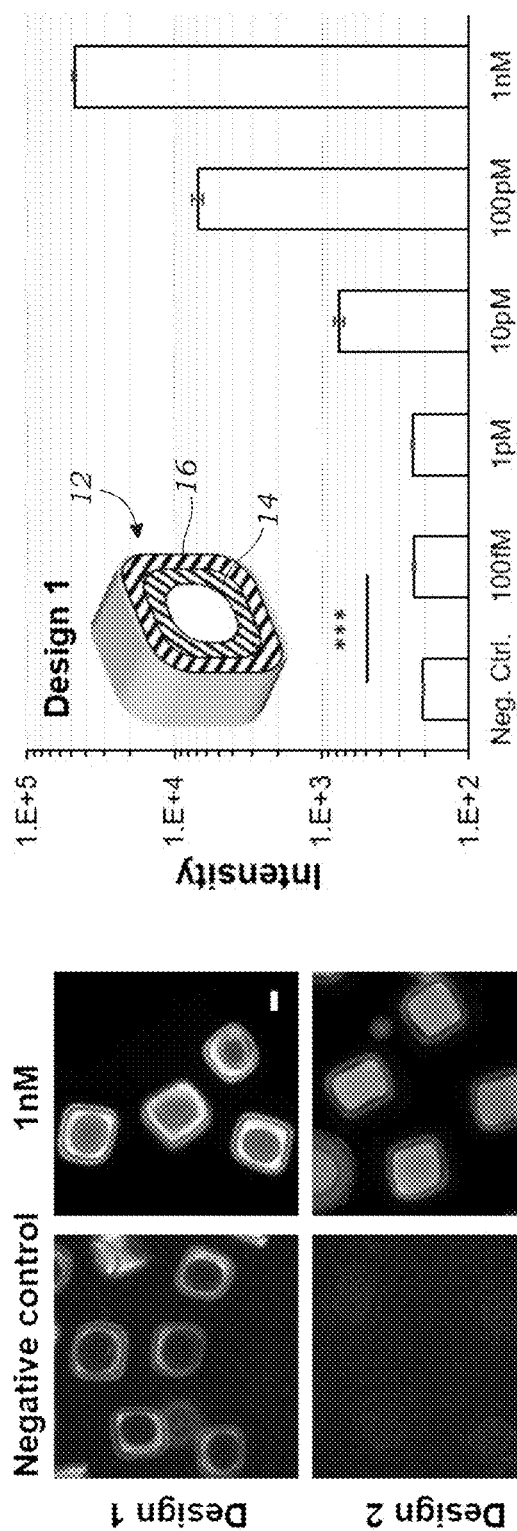
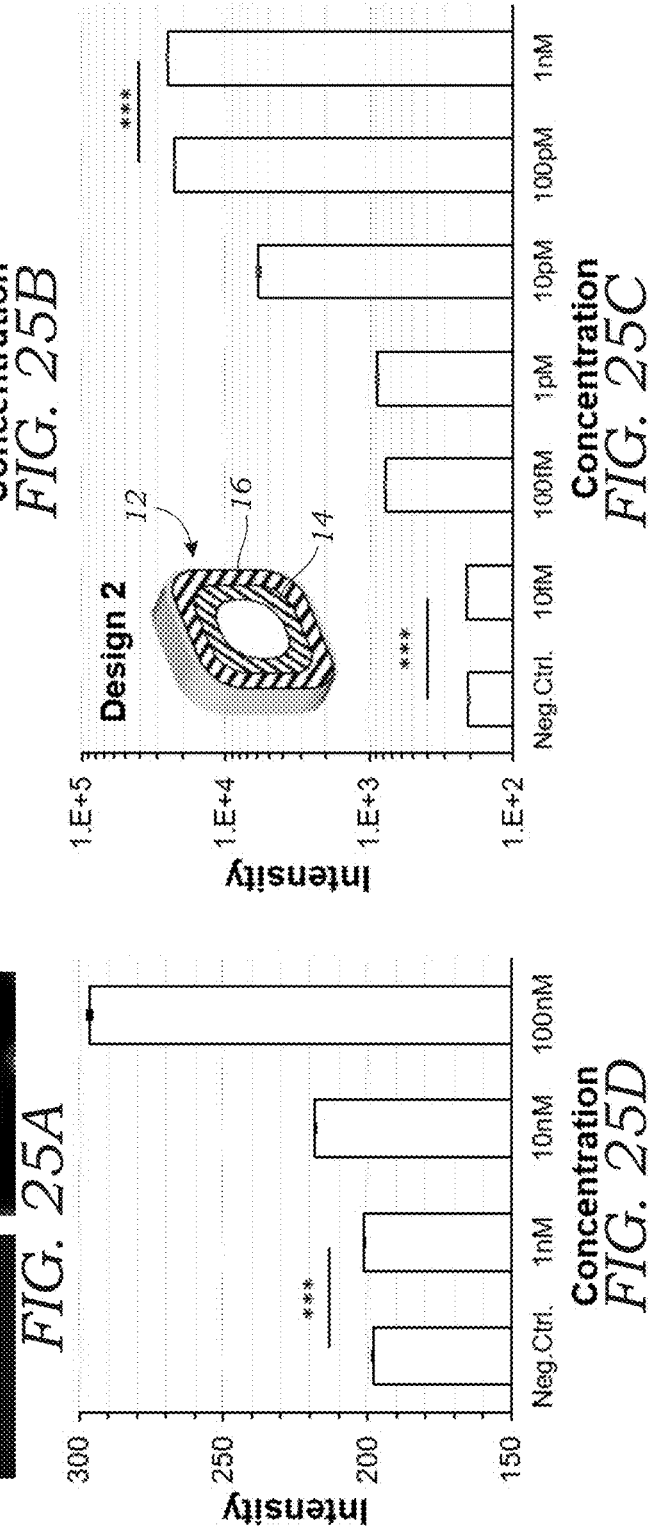
FIG. 25A
FIG. 25B
FIG. 25C
FIG. 25D

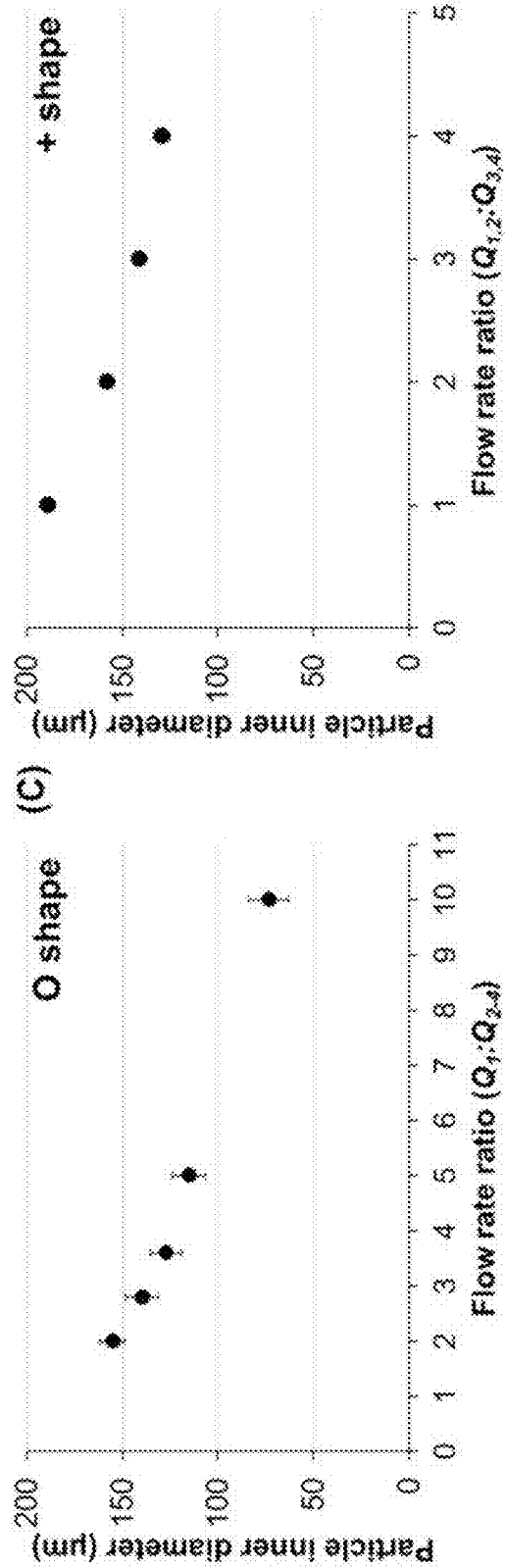
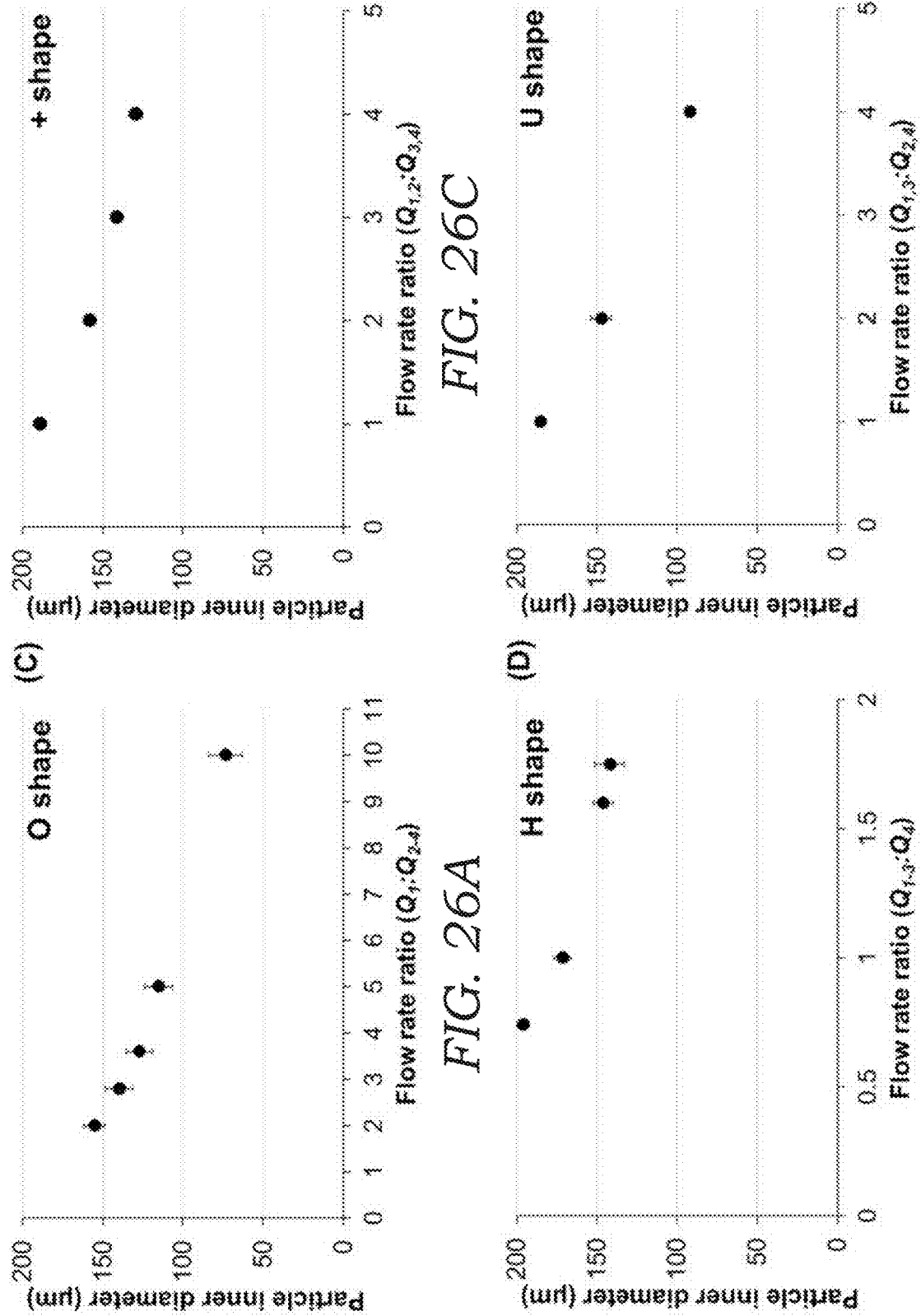
FIG. 26A  FIG. 26B  FIG. 26C  FIG. 26D

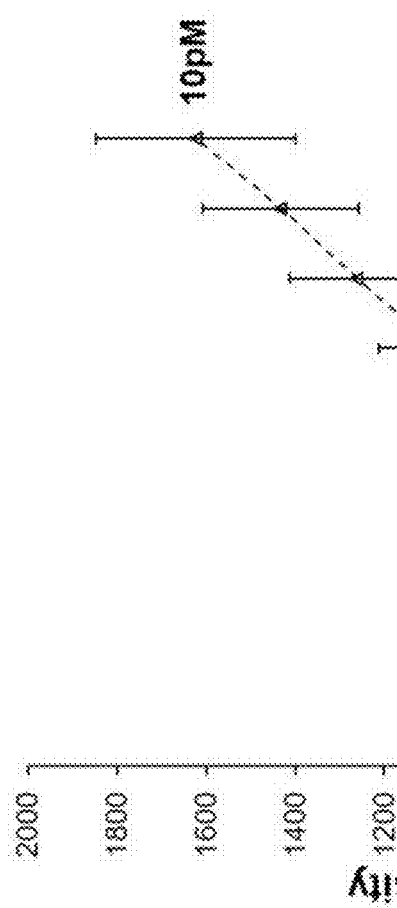
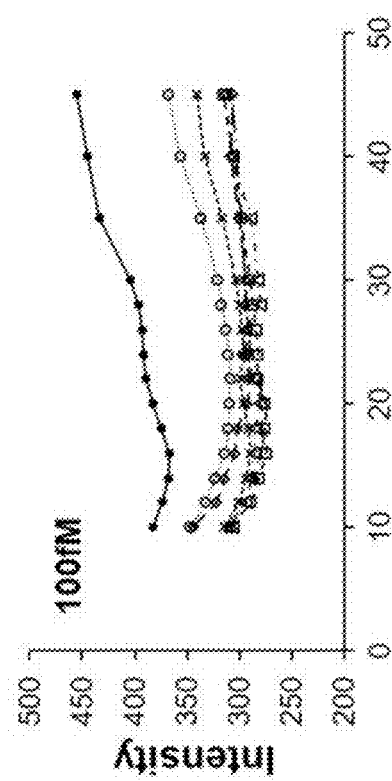
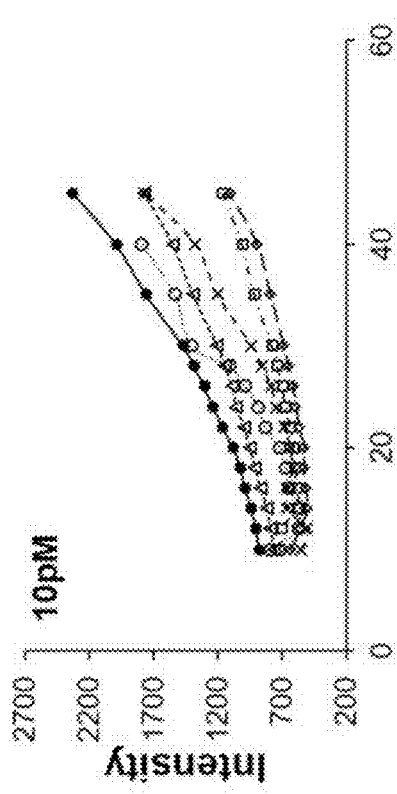
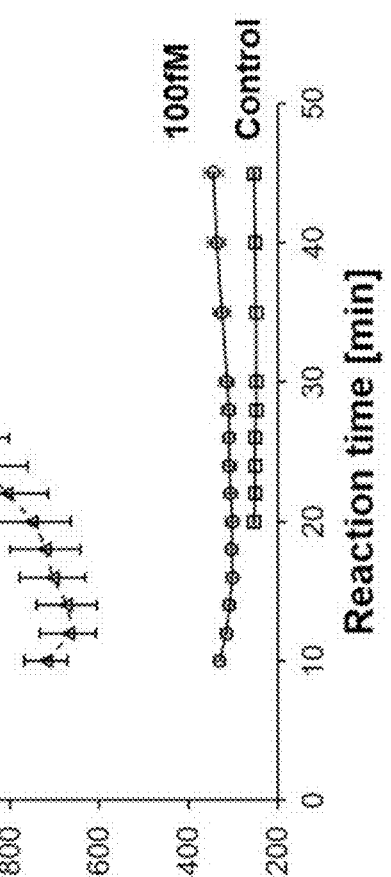
FIG. 27A
FIG. 27B
FIG. 27C

PARTICLE-DROP STRUCTURES AND METHODS FOR MAKING AND USING THE SAME

RELATED APPLICATIONS

This Application is a continuation of U.S. application Ser. No. 18/901,981 filed on Sep. 30, 2024, now allowed, which is a continuation of U.S. application Ser. No. 18/161,322 filed on Jan. 30, 2023, now allowed, which is a continuation of U.S. application Ser. No. 16/550,105 filed on Aug. 23, 2019, now issued as U.S. Pat. No. 11,590,489, which itself is a continuation-in-part of International Patent Application No. PCT/US2018/019486, filed on Feb. 23, 2018, which itself claims priority to U.S. Provisional Patent Application No. 62/463,272 filed on Feb. 24, 2017, all of which are hereby incorporated by reference in its entirety. Priority is claimed pursuant to 35 U.S.C. §§ 120, 119 and any other applicable statute.

STATEMENT REGARDING FEDERALLY SPONSORED RESEARCH AND DEVELOPMENT

This invention was made with government support under 1307550 awarded by the National Science Foundation. The government has certain rights in the invention.

TECHNICAL FIELD

The technical field generally relates to small, sub-millimeter particles with well-defined three-dimensional (3D) structure and chemical functionality. More specifically, the technical field relates to particle-drop structures that are formed from drop-carrier particles that hold a droplet of aqueous fluid therein.

BACKGROUND

Single-molecule or single-cell assays (e.g., digital PCR, digital loop-mediated isothermal amplification (LAMP), digital ELISA, Drop-Seq) require fractionating or compartmentalizing a large volume to such a level that each smaller fractionated volume contains either none (0) or a single (1) entity of interest (i.e., a digital assay). Regardless of the compartment type, it is important that each fractionated compartment is relatively uniform in volume in order to allow reactions to proceed with similar properties in each fractionated volume. Currently, the main approaches to perform this compartmentalization in a uniform manner rely on (i) arrays of wells or (ii) the creation of monodisperse emulsions of drops or droplets using microfluidic approaches. However, there are significant disadvantages to microfluidic approaches given the cost for instruments, pumps, and microfluidic chips required to produce the droplets. Also, small sample volumes can be difficult to use because of the large dead-volumes contained within microfluidic pumping systems. In addition, solid surfaces for reaction or to release reagents and unique barcodes are desired for digital ELISA and single-cell RNAseq, but these are not easy to introduce in microwell arrays or droplets, and can be limited by Poisson statistics. For example, for digital ELISA assays there is often a bead that should be introduced into each volume that provides an affinity reagent to detect a protein of interest, while for single-cell nucleic acid amplification and sequencing assays, it is often desired to include a unique molecular barcode into each droplet such that the RNA amplified from each cell can be re-assigned to the cell of origin even after combining or pooling all of the nucleic acids for a sequencing run. Therefore, there is a need to create simply operated methods of creating uniformly sized fluid compartments that also are associated with solid supports that allow reagent introduction into each compartment or volume.

SUMMARY

In one embodiment, a plurality of small, sub-millimeter scale particles are disclosed that contain well-defined three-dimensional (3D) structures and chemical properties and/or functionality. The 3D structures or particles that are described herein are referred to as drop-carrier particles. The drop-carrier particles allow the selective association of one solution (i.e., a dispersed phased) with an interior portion of each of the drop-carrier particles, while a second non-miscible solution (i.e., a continuous phase) associates with an exterior portion of each of the drop-carrier particles due to the specific chemical and/or physical properties of the interior and exterior regions of the drop-carrier particles. The combined drop-carrier particle with the dispersed phase (e.g., aqueous phase) contained therein is referred to as a particle-drop. The selective association results in compartmentalization of the dispersed phase solution into sub-microliter-sized volumes contained in or otherwise associated with the drop-carrier particles. The compartmentalized volumes can be used for single-molecule (or digital) assays as well as single-cell, and other single-entity assays. Further, each drop-carrier particle can be loaded or covalently linked to a set of barcode molecules, affinity molecules, and/or reagent molecules, such that reactions in each compartmentalized volume can be performed and identified uniquely. Advantageously, the particle-drop structures described herein create monodisperse droplet volumes that are directly associated with a solid support (i.e., the drop-carrier particle) which is compatible with standard benchtop equipment and workflows; without the need for microfluidics or other instruments.

In another embodiment, sculpted microfluidic flows are used to fabricate complex, multi-material 3D-shaped drop-carrier particles in order to create separate wetting surfaces within each drop-carrier particle. For example, in one embodiment, hydrophilic material is polymerized or cross-linked on the interior of the particle, while hydrophobic material surrounds the exterior. These types of Janus particles can be designed with 3D shapes such that they can encapsulate, support, and stabilize water droplets in the interior of the drop-carrier particles inside a cavity or void while being suspended in an oil phase to prevent coalescence of the droplets. Drop-carrier particles can be easily mixed with small volume aqueous samples without complex protocols or instruments and moved between phases and solutions using gravitational or magnetic forces (e.g., for magnetic-microparticle or nanoparticle embedded particles). Particle-drops can be incubated and reacted in oil-filled containers to perform nucleic acid amplification, enzymatic amplification, and other signal generation approaches. Reacted particle-drops can be pooled in a new aqueous solution, or read out using standard microscopy, cost-effective wide-field lensless imaging, or flow cytometry.

There are various possible embodiments of the drop-carrier particle geometry and properties to enable the formation of particle-drops. The drop-carrier particle could be shaped in one cross-section to have an interior void or annulus with a hydrophilic material and an external shell of hydrophobic material that is also annular or, in other embodiments, has protruding regions that minimize particle aggregation. The second cross-section can be planar or flat to enable sandwiching and visualization of particles located between two optically transparent substrates (e.g., glass slides). In a related embodiment the second cross-section instead also contains protrusions and protuberances to prevent the aggregation or association of particles with each other or bridging of the interior aqueous regions between particles when transferred to oil or other hydrophobic continuous phase. In some embodiments these protrusions may include tabs or flaps that can bend or flex under interfacial tension forces to further enclose the interior aqueous regions. For example, these protrusions may protect or sequester the aqueous volumes from the surrounding oil phase or collisions with other particle-drops. In some embodiments the interior hydrophilic portion of the drop-carrier particle can be a void or cavity to hold the dispersed aqueous phase. Alternatively, the interior hydrophilic portion of the drop-carrier particle could be a solid or semi-solid un-swollen or swollen hydrogel. In the case where the interior region is a hydrogel, the pores within the gel may be sized to enable rapid water and molecule transport into the gel. Instead of a hydrophilic interior and hydrophobic exterior material, a fluorophilic exterior region may be used in some embodiments instead to enable use in fluorinated oils and other fluoro-hydrocarbons as a continuous phase.

In an alternative embodiment, two or more particles can assemble to enclose a defined aqueous volume that is substantially uniform for each assembly. One particular drop-carrier particle geometry that achieves this is a crescent or C-shaped hydrophilic interior region with surrounding hydrophobic region in one cross-section. The other cross-section is shaped and sized to create a matched keyed (e.g., rounded in one embodiment) interface. Two particles with these 3D crescent shapes can then come together in an orthogonal arrangement (e.g., rotated generally 90° to one another) to enclose an aqueous droplet when transferred to an oil continuous phase.

In some embodiments, the drop-carrier particles can be loaded with magnetic microparticles or nanoparticles (e.g., iron oxide particles ~1 micron in diameter or less) to impart magnetic properties or density differences to the drop-carrier particles. The drop-carrier particles can also be labeled with fluorescent dyes, up-converting phosphors, light scattering materials, or mixtures of the same to create unique drop-carrier signatures or barcodes associated with the drop-carrier particles. The shape itself of the drop-carrier particle or surface features formed thereon or therein can also be used to create a unique barcode of the type of particle that indicates the unique molecular encoding or affinity reagent associated with that particular particle-drop.

In one embodiment, a particle-drop is disclosed that is formed from a three-dimensional drop-carrier particle having an interior region defining a three-dimensional cavity or void that is open to the external environment of the three-dimensional drop-carrier particle and exterior region, the interior region including a hydrophilic surface and the exterior region including a hydrophobic or fluorophilic material; and an aqueous droplet disposed in the cavity or void of the three-dimensional particle.

In another embodiment, a particle-drop system includes a plurality of three-dimensional drop-carrier particles, each drop-carrier particle having an interior region defining a three-dimensional cavity or void that is open to the external environment of the three-dimensional drop-carrier particle and exterior region, the interior region including a hydrophilic surface and the exterior region including a hydrophobic or fluorophilic material. An aqueous droplet is disposed in the cavity or void of the plurality of three-dimensional drop-carrier particles to form a plurality of particle-drops. The plurality of particle-drops are disposed in an oil phase and the aqueous droplets disposed in the cavity or void of the plurality of three-dimensional drop-carrier particles have substantially the same volumes.

In another embodiment, a particle-drop assembly includes a first three-dimensional drop-carrier particle having an interior region and exterior region, the interior region comprising a hydrophilic region and the exterior region comprising a hydrophobic region; a second three-dimensional drop-carrier particle having an interior region and exterior region, the interior region including a hydrophilic region and the exterior region including a hydrophobic region; and wherein the first and second three-dimensional drop-carrier particles join together to form a combined interior region and wherein an aqueous droplet is disposed in the combined interior region of the joined first and second three-dimensional drop-carrier particles.

In another embodiment, a particle-drop includes a three-dimensional drop-carrier particle having an interior region defining a three-dimensional cavity or void that is open to the external environment of the three-dimensional drop-carrier particle and exterior region, the interior region including a hydrophobic surface and the exterior region including a hydrophilic surface; and an oil-based droplet disposed in the cavity or void of the three-dimensional particle.

In another embodiment, a method of forming particle-drops includes forming a plurality of three-dimensional drop-carrier particles, each drop-carrier particle having an interior region defining a three-dimensional void or cavity that is open to the external environment of the three-dimensional drop-carrier particle and exterior region, the interior region including a hydrophilic surface and the exterior region including a hydrophobic surface; loading the cavity or void of the plurality of three-dimensional drop-carrier particles with aqueous fluid; and suspending the plurality of three-dimensional drop-carrier particles (loaded with the aqueous fluid) in an oil phase.

In another embodiment, a method of performing an assay using a plurality of three-dimensional particle-drops is disclosed. Each particle-drop is formed from a three-dimensional drop-carrier particle having an interior region defining a three-dimensional void or cavity that is open to the external environment of the three-dimensional drop-carrier particle and an exterior region, the interior region including a hydrophilic surface holding an aqueous droplet therein and the exterior region including a hydrophobic surface, wherein the interior region comprises an immobilized antibody specific to an antigen. The method includes: exposing the three-dimensional particle-drops to an aqueous solution containing an antigen specific to the antibody, wherein the antigen enters the aqueous droplet of one or more of the three-dimensional particle-drops to form an antibody-antigen complex; exposing the three-dimensional particle-drops to an aqueous solution containing a secondary antibody and enzyme reporter specific to the antibody-antigen complex; exposing the three-dimensional particle-drops to an aqueous solution containing a fluorogenic or chromogenic substrate to generate a fluorescent or chromogenic signal within one or more of the three-dimensional particle-drops; forming an emulsion of the three-dimensional particle-drops; and reading the fluorescent or color intensity of the plurality of three-dimensional particle-drops.

In one embodiment, a method of forming drop-carrier particles with a microfluidic device includes providing a microfluidic device having a plurality of microfluidic channels formed therein by additive manufacturing (e.g., three-dimensional printing). The plurality of microfluidic channels are configured in a co-axial flow configuration where various precursor solutions co-axially surround one another in custom-sculpted cross-sectional shapes. The precursor fluid is flowed through the microfluidic device and selectively exposed to polymerizing light (e.g., ultraviolet light) that crosslinks some of the fluids into solids to create amphiphilic drop-carrier particles. Different flow rates can be used to tune the dimensions and/or geometry of the created drop-carrier particles.

BRIEF DESCRIPTION OF THE DRAWINGS

FIG. 9A illustrates an end view of a drop-carrier particle according to another embodiment.

FIG. 9B illustrates a perspective view the drop-carrier particle of FIG. 9A.

FIG. 10A illustrates an end view of a drop-carrier particle according to another embodiment.

FIG. 10B illustrates a sectional view of the drop-carrier particle of FIG. 10A in order see the internal structure of the drop-carrier particle.

FIG. 11A illustrates the drop-carrier particle in the state without a fluid droplet contained in the drop-carrier particle.

FIG. 20C illustrates a schematic representation of fluid flow that is sculpted using the embodiment of FIG. 20A that is exposed to crosslinking illumination (e.g., ultraviolet light) passing through a mask. Various "slices" of this flow are thus crosslinked to generate the drop-carrier particles. Each slice results in a separate drop-carrier particle.

FIG. 20D schematically illustrates a cross-sectional view of an exemplary drop-carrier particle formed from crosslinked poly(propylene glycol) diacrylate (PPGDA) and crosslinked poly(ethylene glycol) diacrylate (PEGDA) that generate amphiphilic drop-carrier particles. The interior region is hydrophilic while the exterior region is hydrophobic.

FIG. 20E illustrates a fluorescence microscope image (TRITC) (left) and bright-field (right) image of representative experimentally fabricated drop-carrier particles. The dashed lines mark the outer boundaries of the drop-carrier particle in the fluorescence image (left). The plus-shape drop-carrier particles were incubated with resorufin dissolved in phosphate-buffered saline (PBS) buffer for ~10 min. After washing the excess resorufin away, it is observed that the resorufin has partitioned into the inner PEGDA layer only, thus indicating the presence of multiple-materials within the particle structure as PPGDA layer does not emit any florescent signal. Scale bar is 100 μm.

FIG. 20F illustrates a bright-field image of O-shaped drop-carrier particles suspended in ethanol. Scale bar is 1 mm.

FIG. 20G illustrates a magnified image of the O-shaped drop-carrier particles of FIG. 20F. Images of the drop-carrier particles suspended in ethanol shows a circular cavity within an outer square-shaped boundary of the drop-carrier particle 12. Scale bar is 500 μm.

FIG. 22A illustrates an exemplary operational workflow for the formation of aqueous drops or droplets inside the cavities of drop-carrier particles in a well plate.

FIG. 22B illustrates bright-field images (top) and fluorescence images (bottom) of different shaped particle-drops formed from different shaped drop-carrier particles (O-shaped, H-shaped, Plus (+)-shaped, and U-shaped). The bright-field images (top) show the liquid (aqueous) droplets trapped within the cavity of the solid particles, whereas, the fluorescence images (bottom) clearly show the encapsulated volume of the aqueous phase. Scale bar is 100 μm.

FIG. 22C illustrates histograms that correspond to the normalized intensity of the encapsulated fluorescent droplets which correlates with the volume of the encapsulated fluid within populations of the four differently shaped drop-carrier particles of FIG. 22B.

FIG. 24A illustrates a schematic of two different shaped drop-carrier particles that are used to demonstrate the ability of the particle-drop system to be used for duplex assays with minimal crosstalk between particles over time.

FIG. 24B illustrates a merged microscopic image of bright-field and TRITC channels at a 60 min timepoint from the reaction started using the drop-carrier particles of FIG. 24A, illustrating contrast in fluorescence signal between particle-drops formed from plus (+)-shaped drop-carrier particles (negative group, without biotin attached) and H-shaped drop-carrier particles (positive group, with biotin attached). Both drop-carrier particles were exposed to 0.1 nM streptavidin HRP. The scale bars represent 100 μm.

FIG. 24C illustrates microscopic fluorescence images of the same field of view as in FIG. 24B at three sequential timepoints, i.e., 15, 35 and 60 min from the reaction start point. The dashed lines in the images outline the boundary of particle-drops. There are positive particle-drops in which biotin-modified H-shaped drop-carrier particles are bound to streptavidin HRP and negative particle-drops in which plus (+)-shaped drop-carrier particles without biotin modification did not bind streptavidin HRP when both types were exposed to 0.1 nM streptavidin HRP. H-shaped drop-carrier particles forming particle-drops show higher distinguishable fluorescent intensity in the drops held in their cavity. The scale bars represent 100 μm.

FIG. 24D illustrates histograms based on analysis across the whole well of a population of particle-drops at 15, 35 and 60 min, respectively. The signal from the internal cavity of particle-drops from plus (+)-shaped particles (negative group) increased at a much slower rate compared to that of H-shaped particles (positive group, 0.1 nM streptavidin HRP).

FIG. 24E illustrates the average of fluorescent intensity within the internal cavity of particle-drops at three timepoints 15, 35, and 60 min for H- and Plus-shaped drop-carrier particles. The error bars represent standard deviation.

FIG. 25A illustrates microscopic images of QuantaRed™ assay results with particle-drops based on a biotin-streptavidin HRP assay using two O-shaped drop-carrier particle designs at two conditions, i.e., negative control and 1 nM streptavidin HRP. The scale bar represents 100 μm.

FIGS. 25B and 25C illustrate respective graphs of average intensity after 45 min in the aqueous phase in particle-drop voids for the negative controls and different concentrations of streptavidin HRP showing amplified assay performance using (FIG. 25B) drop-carrier particle design 1 and (FIG. 25C) drop-carrier particle design 2. Drop-carrier particle 1 exhibits a limit-of-detection (LOD) of 100 fM, and linear range from 1 pM to 1 nM. Drop-carrier particle 2 exhibits improved LOD of 10 fM, but narrower linear range from 1 pM to 100 pM. In the negative control group, drop-carrier particles were incubated with PBS only, all the other steps were kept the same as positive groups as described in FIG. 23A.

FIG. 25D illustrates a graph of intensity for the negative controls and different concentrations of streptavidin-Alexa Fluor® 568 showing assay performance without amplification using enzymes but instead using direct fluorescent labeling of streptavidin. Drop-carrier particles with design 2 were transferred to a well plate and washed in the same manner as (FIG. 25C), followed by incubation with streptavidin-Alexa Fluor® 568 for 30 min, then washed 3 times in PBS with 0.5% v/v Pluronic (PBSP). Next, particle-drops were formed in PBS with oil added. In the negative control group, particle-drops were incubated with PBS only, all the other steps were kept the same as positive groups. Fluorescence images were obtained in the same manner as the QuantaRed™ assay with 40 ms exposure time. Fluorescent (TRITC) signal remained on the surface of the drop-carrier particles and are generated from biotin-streptavidin-Alexa Fluor® 568 complex. Error bars in FIGS. 25B-25D represent standard error. *** represents p<0.001.

FIG. 26A illustrates a graph of the drop-carrier particle inner diameter (μm) as a function of flow rate ratio ($Q_1:Q_{2-4}$) for O-shaped drop-carrier particles. Measurements made for drop-carrier particles in ethanol.

FIG. 26B illustrates a graph of the drop-carrier particle inner diameter (μm) as a function of flow rate ratio ($Q^{1-3}:Q^4$) for H-shaped drop-carrier particles. Measurements made for drop-carrier particles in ethanol.

FIG. 26C illustrates a graph of the drop-carrier particle inner diameter (μm) as a function of flow rate ratio ($Q_{1,2}:Q_{3,4}$) for Plus (+)-shaped drop-carrier particles. Measurements made for drop-carrier particles in.

FIG. 26D illustrates a graph of the drop-carrier particle inner diameter (μm) as a function of flow rate ratio ($Q_{1,3}:Q_{2,4}$) for U-shaped drop-carrier particles. Measurements made for drop-carrier particles in ethanol.

FIG. 27A illustrates a graph of observed intensity of the drop-filled void region of amplified particle-drops using QuantaRed™ assay as a function of time. Amplified signal changes over time from 10 to 45 min for 10 pM and 100 fM conditions, and negative control group using particles incubated with PBS only without HRP are shown. Points indicate the average intensity with error bars indicating standard error of the mean.

FIG. 27B illustrates a graph of observed intensity of individual amplified particle-drops (100 fM conditions) using QuantaRed™ assay as a function of time.

FIG. 27C illustrates a graph of observed intensity of individual amplified particle-drops (10 pM conditions) using QuantaRed™ assay as a function of time.

DETAILED DESCRIPTION OF THE ILLUSTRATED EMBODIMENTS

Figure 1:
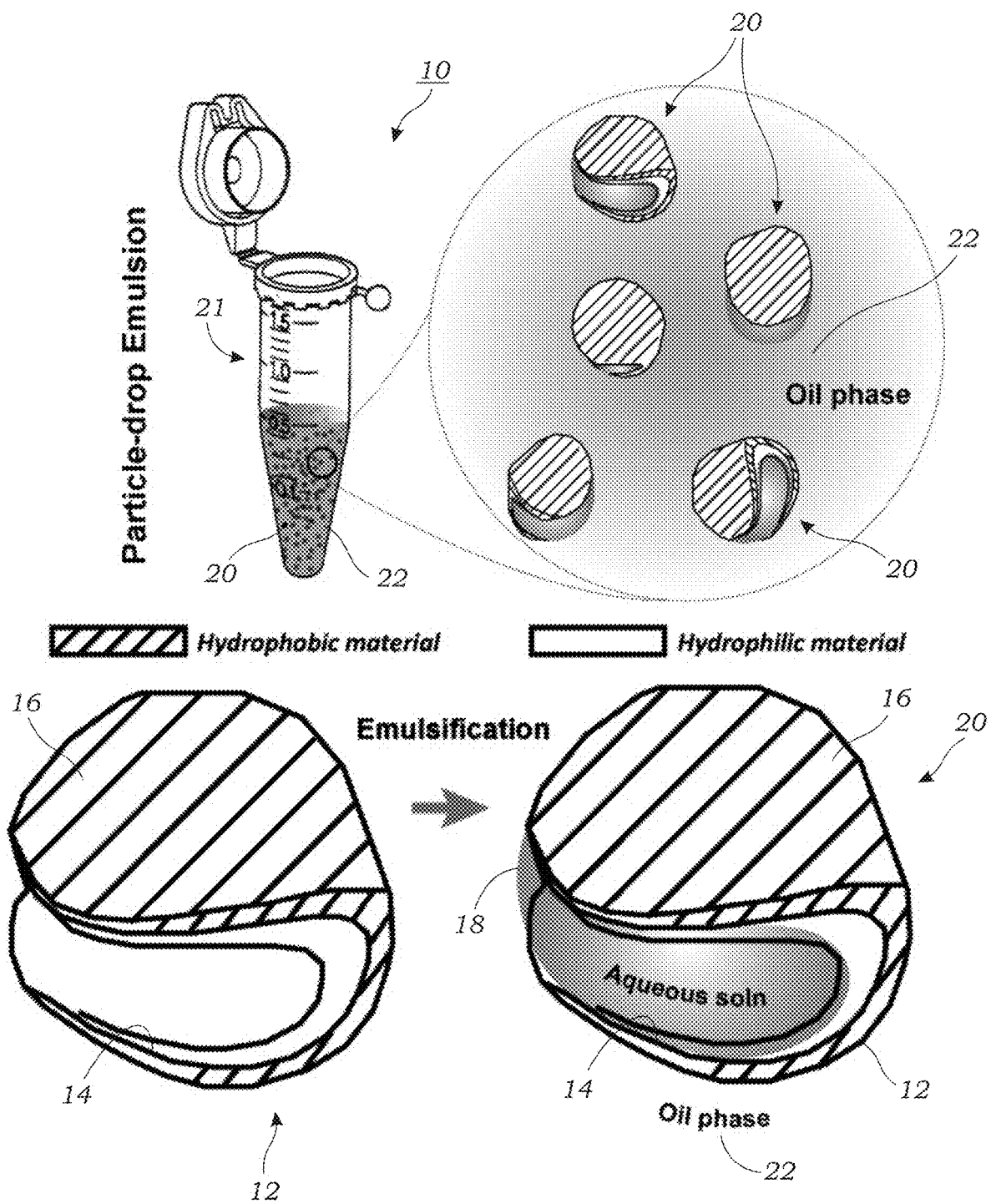
FIG. 1 illustrates one embodiment of a particle-drop system. An emulsion of particle-drops is illustrated in a vial containing an oil phase. Also illustrated is the drop-carrier particle undergoing emulsification to include an aqueous droplet contained inside the drop-carrier particle.

FIG. 1 illustrates one embodiment of a particle-drop system 10. The particle-drop system 10 includes a plurality of three-dimensional drop-carrier particles 12. The drop-carrier particles 12 are small, sub-millimeter scale solid particles that are formed having a particular geometric shape and have an interior region 14 and an exterior region 16. The interior region 14 of the drop-carrier particle 12 defines a three-dimensional volume that holds a fluid droplet 18. The fluid droplet 18 is the dispersed phase of an emulsion and, in one preferred embodiment, is an aqueous phase (e.g., formed from water). The interior region 14 of the drop-carrier particle 12 is, in one embodiment, hydrophilic. The hydrophilic nature of the interior region 14 may be achieved by the choice of material used during the manufacturing process used to make the drop-carrier particles 12 as explained herein. Alternatively, the interior region 14 may be rendered hydrophilic after formation of the drop-carrier particle 12. The exterior region 16 of the drop-carrier particle 12 is, in one embodiment, hydrophobic. In another embodiment, the exterior region 16 of the drop-carrier particle 12 is fluorophilic. The hydrophobic or fluorophilic nature of the exterior region 16 may be achieved by the choice of material used during the manufacturing process used to make the drop-carrier particles 12 as explained herein. Alternatively, the exterior region 16 may be selectively rendered hydrophobic (or fluorophilic) after formation of the drop-carrier particle 12.

With reference to FIG. 1, when the drop-carrier particle 12 is loaded with the droplet 18, the resulting construct is referred to herein as a particle-drop 20. A plurality of these particle-drops 20 form an emulsion contained in a vial 21. The particle-drop system 10 that is described herein has a plurality of particle-drops 20 that are disposed in oil 22 to form a particle-drop 20 emulsion. The oil 22 acts as the continuous phase while the aqueous-based droplet 18 acts as the dispersed phase. The oil 22 surrounds the particle-drops 20 to create a monodisperse particle-drop 20 emulsion. Monodisperse refers to the ability of the particle-drops 20 to retain substantially the same volume of fluid in each particle-drop 20.

Importantly, the monodisperse particle-drop 20 emulsions are created without the need of any complex or expensive instruments. Notably, the assembly of drop-carrier particles 12 supports a unique volume of an aqueous droplet 18, unlike droplets of multiple volumes supported by Pickering emulsions, such that a plurality of particle-drops 20 enables the formation of a monodisperse emulsion. As explained herein, drop-carrier particles 12 are formed from multiple material types into shaped particles with wetting surfaces that are strategically located, in some embodiments, on the interior of the drop-carrier particles 12. For example, hydrophilic material is polymerized or crosslinked using light exposure on the interior cavity of the drop-carrier particle 12 to form a hydrophilic surface while a separate hydrophobic material also polymerized or crosslinked using light surrounds the cavity or void 24 as is illustrated in FIG. 1 and forms a hydrophobic surface. In one preferred embodiment, the cavity or void 24 is open to the external environment of the drop-carrier particle 12 (i.e., there is one or more openings that communicate with the external environment of the drop-carrier particle 12). The drop-carrier particles 12 may be made from known polymer materials that can be polymerized or crosslinked using, for example, light-initiated polymerization as explained herein.

The drop-carrier particles 12 that are used to form the particle-drops 20 are sub-millimeter sized particles. Typically, the drop-carrier particles 12 have diameters or widths on the order of around 100-200 microns, although it should be appreciated that drop-carrier particles 12 of different sizes outside this specific range may also be used. While the embodiments described herein largely describe drop-carrier particles 12 having a hydrophilic interior region 14 and a hydrophobic exterior region 16, it should be appreciated that these regions could be reversed with the interior region 14 being hydrophobic (or fluorophilic) and the exterior region 16 being hydrophilic. In such an embodiment, the fluid droplet 18 that is carried by the drop-carrier particle 12 would be a hydrophobic fluid such as oil while the continuous phase that surrounds the particle-drops 20 would be an aqueous solution.

In some embodiments, materials that comprise the hydrophobic exterior region 16 preferably will possess an interfacial tension with the continuous phase substantially close to zero. This enables mixing of the particle-drops 20 within the continuous phase without aggregation of the particle-drops 20 at their exterior surfaces. That is, the particle-drops 20 can remain well-suspended within the continuous phase. In order to form well-defined fluid drops 18, the interfacial tension between the internal phase and interior surface or region 14 is less than interfacial tension between the internal phase and exterior surface or region 16. In some embodiments a surfactant (e.g. Pluronic®, Pico-Surf™) is used to adjust the interfacial tensions between the phases to achieve these favorable conditions. Note that in this case the drop-carrier particle 12 still controls the shape and volume of the fluid drop 18, which would vary over a much larger range with the use of a surfactant alone.

The drop-carrier particles 12 may be referred to as Janus particles because of their dual hydrophilic/hydrophobic surfaces. These Janus drop-carrier particles 12 can be designed with 3D shapes such that the drop-carrier particles 12 can encapsulate, support, and stabilize aqueous droplets 18 in the interior of the drop-carrier particles 12 while being suspended in an oil phase 22 to prevent coalescence of the droplets 18. The interior hydrophilic region 14, in some embodiments, can also be specifically functionalized to support nucleic acid barcodes or affinity capture reagents. For example, one or more biomolecules may be tethered (e.g., covalently attached to or through one or more linking moieties) to the surface of the interior region 14 of the drop-carrier particle 12. As one illustrative example, antibodies may be bound to the interior hydrophilic region 14 of the drop-carrier particle 12 which is used to detect an antigen as explained herein.

Drop-carrier particles 12 can be easily mixed with small volumes of aqueous samples without complex protocols or instruments and moved between phases and solutions using gravitational, centripetal, or magnetic forces (for magnetic particle embedded drop-carrier particles 12 as explained herein). Similar to microfluidic droplets or microwells, particle-drops 20 can be incubated and reacted in oil-filled containers to perform a variety of chemical and biological reactions. Examples include, by way of illustration and not limitation, reverse transcription of RNA, nucleic acid amplification, enzymatic amplification, and other signal generation approaches. Reacted particle-drops 20 can be pooled in a new aqueous solution, or read out using standard microscopy, cost-effective wide-field lens-less imaging, or conventional flow cytometry devices; leading to low-cost complete solutions that can democratize digital molecular and single-cell assays in all research labs, and galvanize the development of point-of-care digital diagnostics that will ultimately improve health.

Figure 2A:
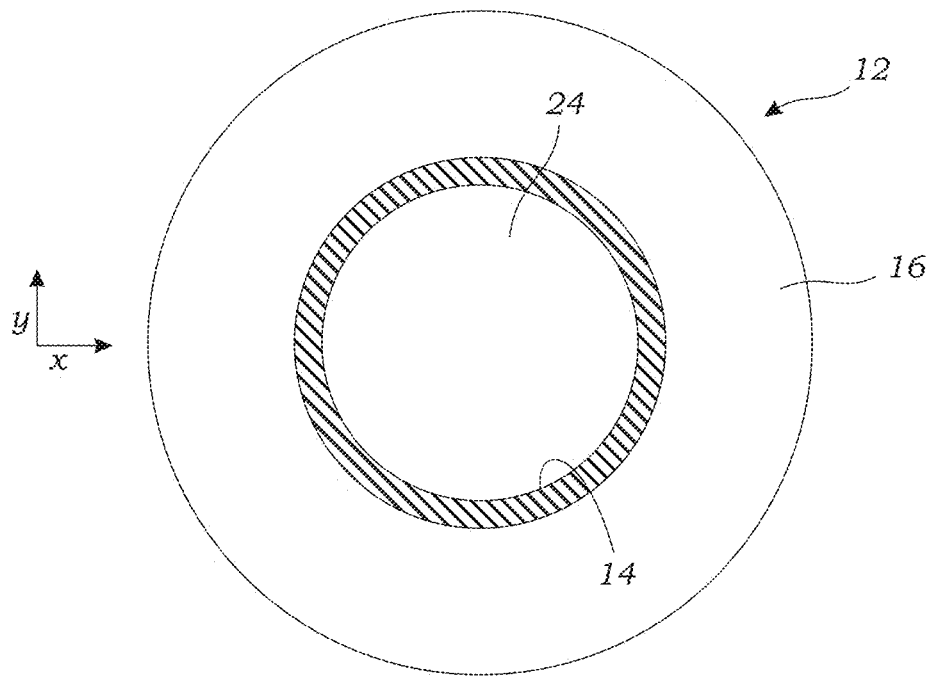
FIG. 2A illustrates a planar view of a drop-carrier particle according to one embodiment.

The hydrophilic interior region 14 of the drop-carrier particles 12 can vary in size and shape. The size of the drop-carrier particles 12 should be small enough that surface forces dominate (e.g., sub-millimeter) and control the assembly of fluid within the interior region 14 of the drop-carrier particle 12, compared to gravity, fluid inertia, etc. The interior region size should be between about 10 micrometers and about 500 micrometers in an average linear dimension, defining a cavity or void 24 with a holding volume between about 1 µL and about 125 nL. For example, a Bond Number (Bo), defined as the ratio of gravitational to surface tension forces preferably is smaller than unity (1). Here, $$Bo = \frac{\Delta \rho g L^2}{\sigma},$$

where Δp is the magnitude of the density difference between the interior and exterior liquid phases (e.g., water and oil), g is the acceleration due to gravity, L is a linear dimension of the interior hydrophilic region 14 of the drop-carrier particle 12, and σ is the interfacial tension between the interior phase and the interior region 14. The shape of the drop-carrier particle 12 should facilitate the entry of an interior liquid phase into the interior region 14 while preventing the assembly of a random number of multiple drop-carrier particles 12 around an interior liquid phase drop yielding uncontrolled and polydisperse volumes in a stabilized emulsion. The drop-carrier particle 12 shape preferably comprises an interior hydrophilic region 14 surrounded by an exterior hydrophobic region 16 over an angle of greater than 180° around at least one axis. In other embodiments the shape of the drop-carrier particle 12 defines an interior hydrophilic region 14 surrounded by an exterior hydrophobic region 16 over an angle of greater than 180° around at least one axis and an interior hydrophilic region 14 surrounded by an exterior hydrophobic region 16 over an angle of greater than 90° around a second orthogonal axis. Exemplary designs with this characteristic are shown in FIGS. 1 and 2A. In some embodiments the hydrophobic exterior region 16 surrounds the hydrophilic interior region 14 over an angle of at least 270° around at least one axis. Exemplary drop-carrier particles 12 having hydrophobic exterior regions 16 surrounding interior regions 14 with an angle of 360° around one axis are shown in FIGS. 2A, 2B, 3A, and 3B.

Figure 2B:
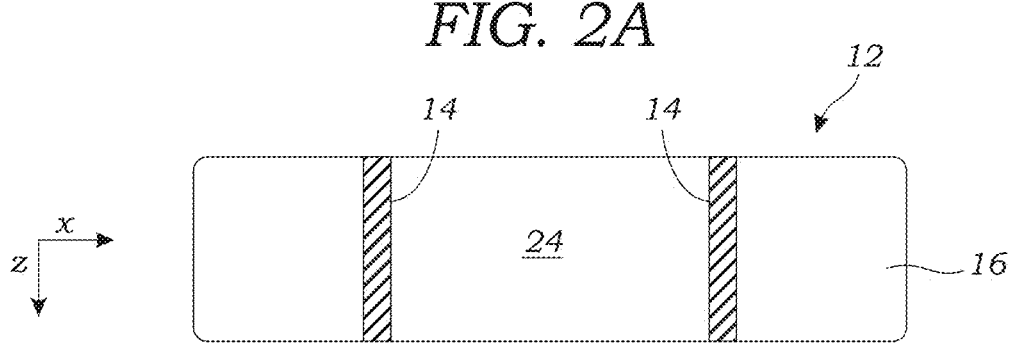
FIG. 2B illustrates a cross-sectional view of the particle of FIG. 2A taken along a diameter or major axis of the drop-carrier particle of FIG. 2A.
Figure 2C:
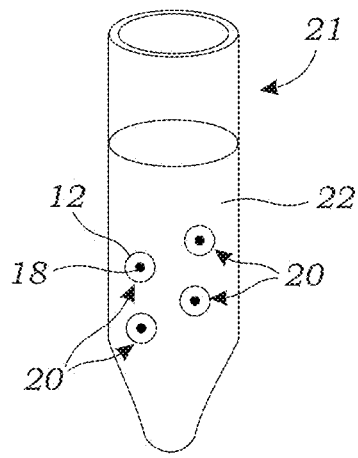
FIG. 2C illustrates a vial containing a plurality of particle-drops contained in an oil phase.

FIGS. 2A and 2B illustrate another example of a drop-carrier particle 12 that includes a central cavity or inner void 24 that is surrounded by a hydrophilic interior region 14 formed from hydrophilic material. The external or outer surface 16 of the drop-carrier particle 12 defines a hydrophobic region and is formed from a hydrophobic material. In this embodiment, the drop-carrier particle 12 is in the shape of a ring or annulus that has flat or planar top and bottom surfaces as best seen in FIG. 2B. This way, the drop-carrier particles 12 can be disposed between two optically transparent substrates (e.g., glass slides or glass slides with a hydrophobic surface coating) with the flat surfaces facing the two substrates. FIG. 2C illustrates a vial 21 containing a plurality of particle-drops 20 contained in an oil phase 22.

Figure 3A:
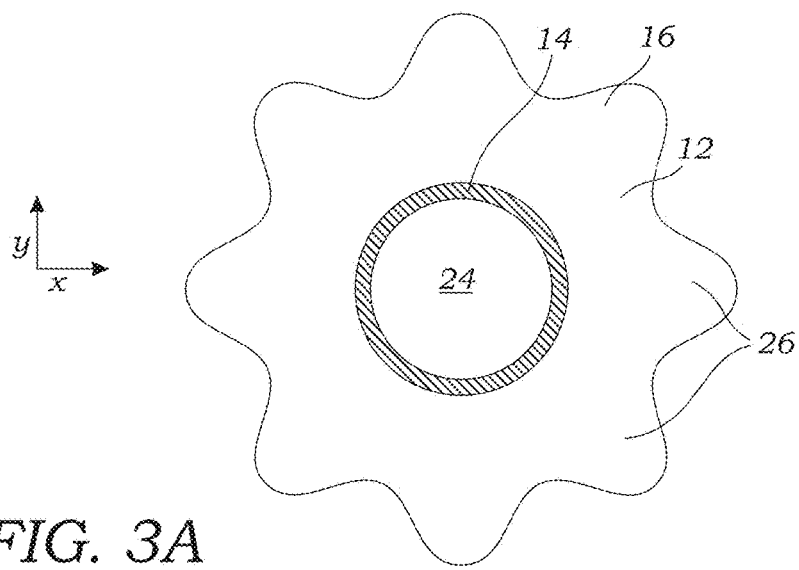
FIG. 3A illustrates a planar view of a drop-carrier particle according to one embodiment. In this embodiment, the drop-carrier particle includes a plurality of protrusions about the periphery of the drop-carrier particle.
Figure 3B:
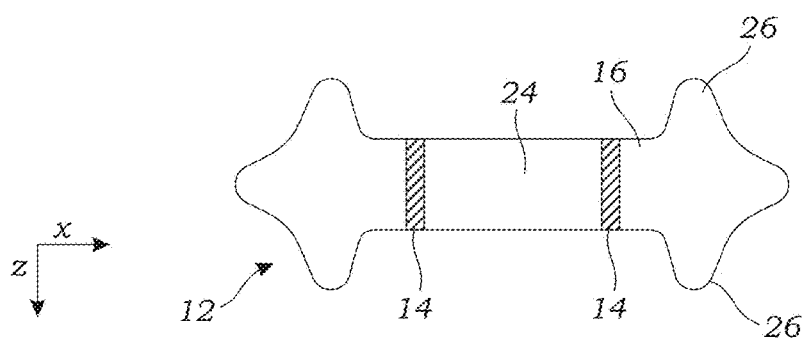
FIG. 3B illustrates a cross-sectional view of the particle of FIG. 3A taken along a diameter or major axis of the drop-carrier particle of FIG. 3A.

FIGS. 3A and 3B illustrate another example of a drop-carrier particle 12. The drop-carrier particle 12 also includes a central cavity or inner void 24 that defines a hydrophilic interior region 14. The external or outer surface 16 of the drop-carrier particle 12 defines a hydrophobic region. In this embodiment, the external or outer surface includes a plurality of protrusions 26 that minimize the surface area of contact between drop-carrier particles 12 to prevent the drop-carrier particles 12 from aggregating together.

Figures 4A, 4B, 4C:
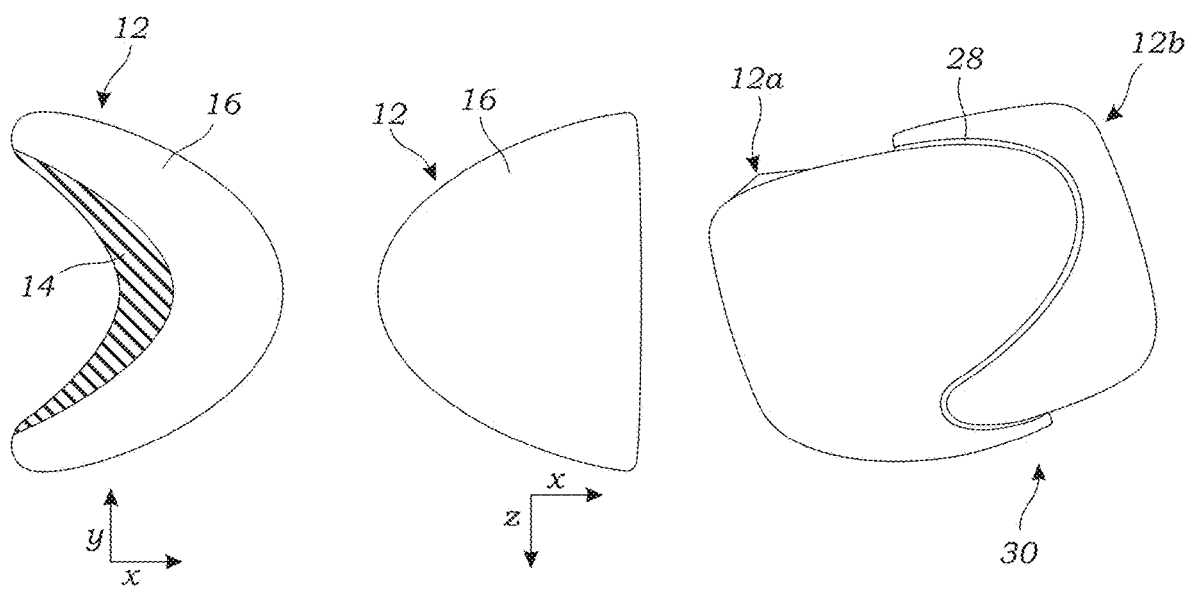
FIG. 4A illustrates a perspective view of a drop-carrier particle according to one embodiment.
FIG. 4B illustrates a planar view of the drop-carrier particle of FIG. 4A.
FIG. 4C illustrates two drop-carrier particles of the type illustrated in FIGS. 4A and 4B combining to form a single particle assembly.

FIGS. 4A-4C illustrates another embodiment of drop-carrier particles 12 that join together as illustrated in FIG. 4C to form a combined interior region 28 that is used to hold the fluid droplet 18 (not illustrated in FIG. 4C). In this embodiment, there are two crescent shaped drop-carrier particles 12a, 12b. The inner saddle-shaped surface 14 of the drop-carrier particles 12a, 12b is hydrophilic while the outer surface or region 16 is hydrophobic. Two of the crescent shaped drop-carrier particles 12a, 12b fit or nest together to form a single particle assembly 30 in which the combined hydrophilic surfaces 14 enclose a void or region 28 that holds the aqueous droplet 18. In an alternative embodiment, the two different drop-carrier particles 12 may be oriented orthogonal to one another (i.e., rotated orthogonally to one another generally) 90° to form the single particle assembly 30. Various lock-and-key fitting arrangements between drop-carrier particles 12 can be utilized.

Figure 5:
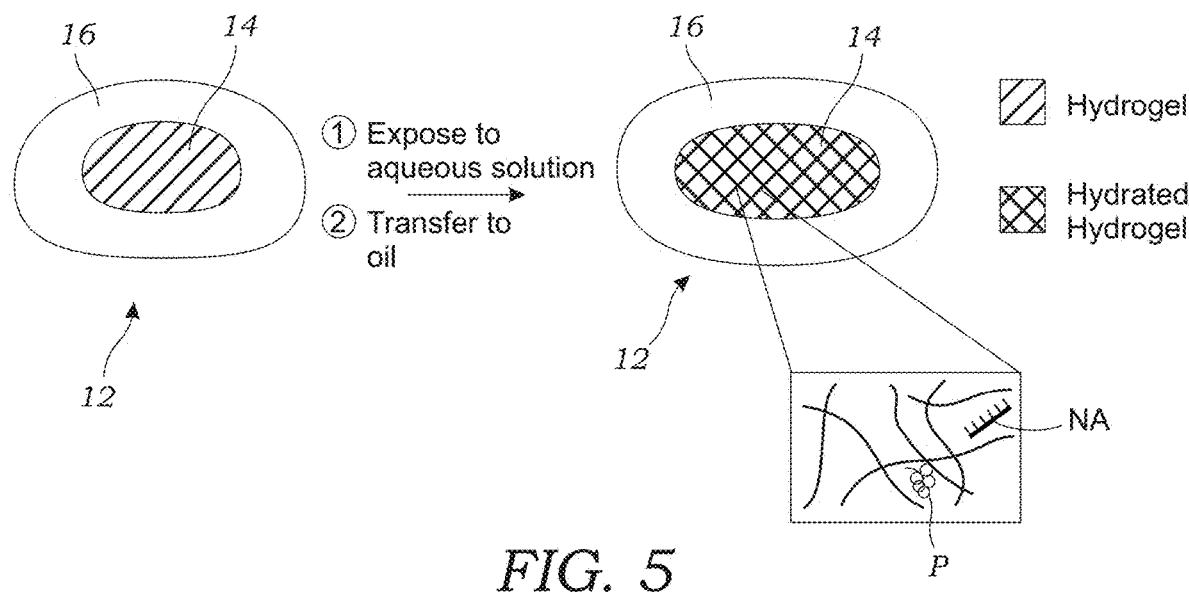
FIG. 5 illustrates another embodiment of a drop-carrier particle. In this embodiment, the drop-carrier particle contains a hydrogel in the interior portion of the drop-carrier particle.

FIG. 5 illustrates another embodiment of a drop-carrier particle 12. In this embodiment, the drop-carrier particle 12 contains a hydrogel in the interior portion 14 of the drop-carrier particle 12. Examples of hydrogel materials that can be formed in the interior portion 14 of the drop-carrier particle 12 include polyethylene glycol (PEG)-based hydrogels such as poly(ethylene glycol) diacrylate (PEGDA). The hydrogel may be dried or partially wetted hydrogel material that is then exposed to an aqueous solution, which may also contain analytes, reagents, affinity probes or reagents, and the like, which can then enter the hydrogel void spaces. The porosity of the hydrogel may be tuned to control the ingress or egress of molecular species. For example, porosity may be tuned to trap molecules within the hydrogel or prevent larger molecules from entering the hydrogel. In some embodiments, the hydrogel may be biotinylated using a biotin modified PEG precursor. The biotinylated surface may be used to bind other biomolecules on or within the hydrogel. FIG. 5 illustrates one embodiment where protein (P) or nucleic acid (NA) molecules are loaded within the hydrogel filled interior portion 14 of the drop-carrier particle 12. The hydrogel-containing particle-drops 20 can then be transferred to an oil solution to form the emulsion.

Figure 6:
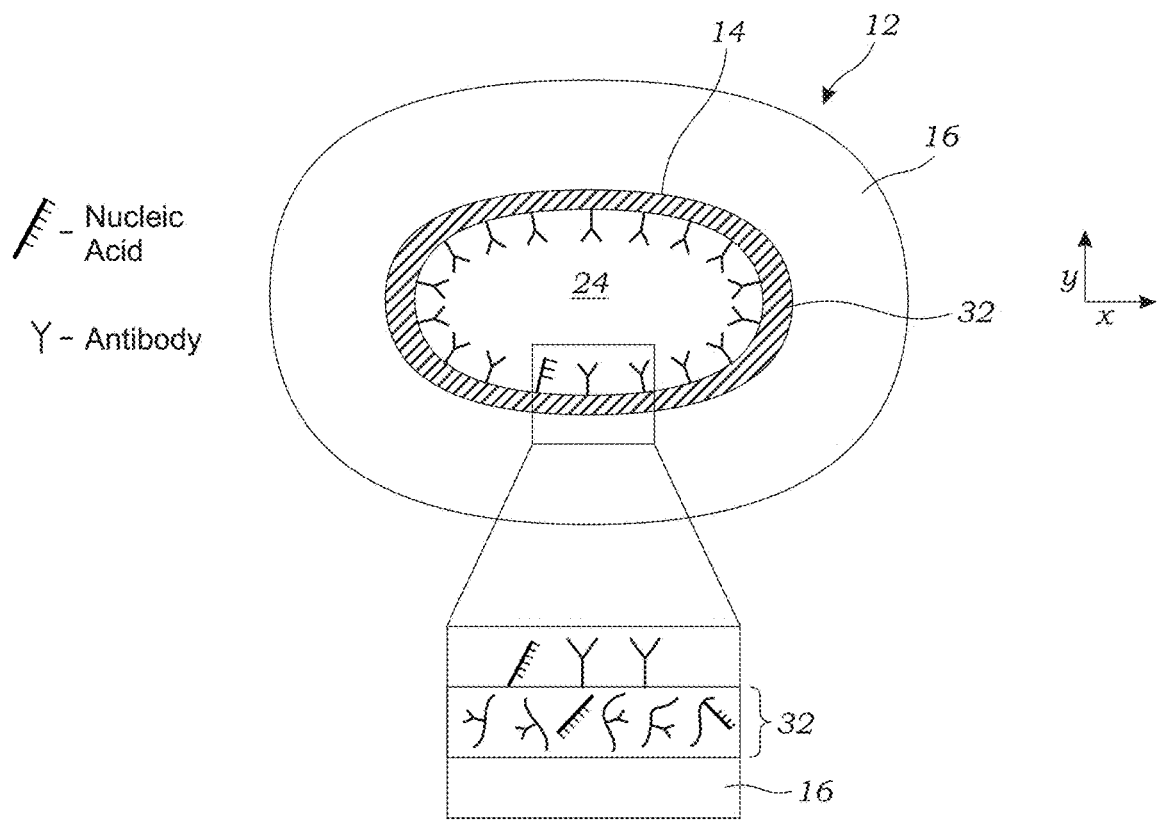
FIG. 6 illustrates another embodiment of a drop-carrier particle. In this embodiment, a hydrogel layer coats an interior portion (e.g., inner surface) of the drop-carrier particle. Biomolecules are located on or within the hydrogel layer.

FIG. 6 illustrates another embodiment of a drop-carrier particle 12. In this embodiment, a hydrogel layer 32 coats an interior portion 14 (e.g., inner surface) of the drop-carrier particle 12. In this embodiment, the hydrogel layer 32 coats an inner surface of the drop carrier particle 12 but leaves a void 24 which may accommodate a fluid droplet 18. The hydrogel layer 32 may contain various moieties or biomolecules therein. For example, as seen in FIG. 6, nucleic acids or antibodies may be contained within the inside of the hydrogel layer 32. Alternatively, or in conjunction with interior biomolecules or other moieties, surface bound nucleic acids, antibodies, or antigens may be located at the surface of the hydrogel layer 32.

Figure 7:
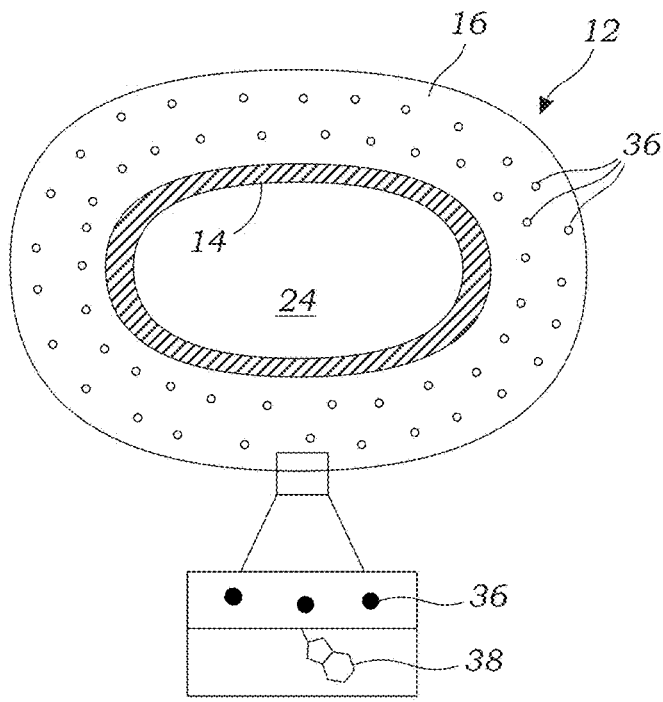
FIG. 7 illustrates another embodiment of a drop-carrier particle that contains magnetic particles therein.

FIG. 7 illustrates another embodiment of the invention. In this embodiment, the drop-carrier particle 12 includes magnetic particles 36 contained in the exterior region 16 (e.g., the outer hydrophobic layer of the drop-carrier particle 12). These magnetic particles 36 may be micro-sized (e.g., having a width or diameter of 1 µm and less than 1 mm) or nanometer-sized (e.g., having a size between 1 nm and 1 µm). The magnetic particles 36 may be made from iron oxide or other ferromagnetic materials. The magnetic particles 36 may be contained in one or more of the polymer or pre-polymer components that is flowed through the microfluidic device during the drop-carrier particle 12 formation process as explained herein. The magnetic particles 36 enable the drop-carrier particles 12 to be manipulated by an externally applied magnetic field which could be a permanent magnet or an electromagnet. For example, drop-carrier particles 12 may be pulled (or pushed) through various solutions (e.g., oil-based fluid, aqueous-based fluid, rinse fluids, wash fluids, reagent fluids, interfaces between two immiscible fluids) using an applied magnetic field. FIG. 7 illustrates a covalently linked fluorophore 38 to the outer surface of the drop-carrier particle 12.

Figure 8A:
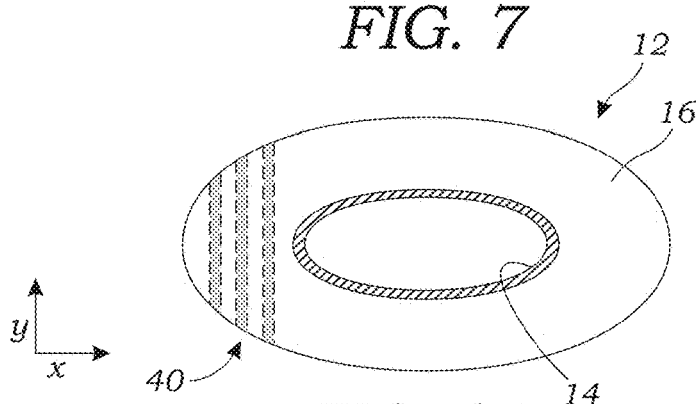
FIG. 8A illustrates another embodiment of a drop-carrier particle that includes unique indicia or barcode that uniquely identifies the particular drop-carrier particle. In the embodiment of FIG. 8A, the unique indicia or barcode is extruded through a width of the drop-carrier particle.
Figure 8B:
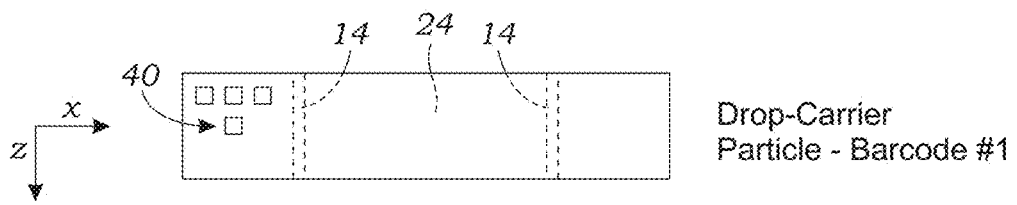
FIG. 8B illustrates a side view of a drop-carrier particle having a barcode identifying the drop-carrier particle with barcode #1.
Figure 8C:
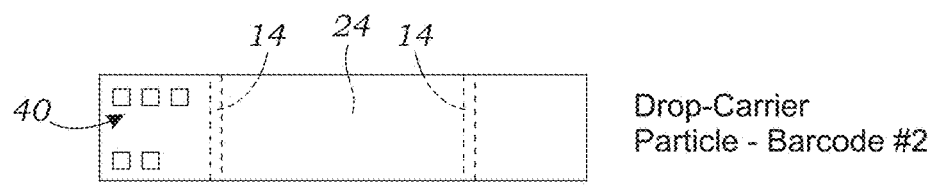
FIG. 8C illustrates a side view of a drop-carrier particle having a barcode identifying the drop-carrier particle with barcode #2.

FIGS. 8A-8C illustrate another embodiment of a drop-carrier particle 12. In this embodiment, the drop-carrier particles 12 are labelled with a unique indicia 40 that identify the particular drop-carrier particle 12. The unique indicia 40 may also be referred to as a "barcode" because it provides a unique identifier for the drop-carrier particle 12. The unique indicia 40 may be embodied in a number of different manifestations. For example, the unique indicia 40 may include holes or apertures formed in the drop-carrier particles 12, shapes, patterns, or surface features formed on or in the drop-carrier particles 12, fluorescent labels, markers, or the like. It should be appreciated that while the unique indicia 40 identifies a particular drop-carrier particle 12, multiple different drop-carrier particles 12 may, in some embodiments, share the same unique indicia 40. For example, a first plurality of drop-carrier particles 12 may contain a certain antibody bound or contained therein. All of these drop-carrier particles 12 may be labelled with the same unique indicia 40 so as to reflect that each of these drop-carrier particles 12 contains the same antibody. Of course, in other embodiments, each different drop-carrier particle 12 may contain different unique indicia 40.

FIGS. 9A and 9B illustrate another embodiment of a drop-carrier particle 12. In this embodiment, the drop-carrier particle 12 is in the shape of a cylinder with the interior region 14 being hydrophilic and an exterior region 16 being hydrophobic. As seen in FIG. 9A, a central cavity or inner void 24 is surrounded by a hydrophilic interior region 14. An aqueous solution is isolated into a fluid droplet 18 (not illustrated in FIGS. 9A, 9B) and is protected within the interior region 14 in contact with the interior hydrophilic material when contained in an oil solution. This embodiment is created through the flow of precursor materials through a series of nested cylindrical tubes to create a concentric layered flow of precursor materials (e.g. from inner to outer material in four concentric tubes, PEGDA, PEGDA+PI, PPGDA+PI, PPGDA) that can be photopolymerized downstream through a mask containing at least one rectangular opening as described herein.

FIGS. 10A and 10B illustrate another embodiment of a drop-carrier particle 12. In this embodiment, the drop-carrier particle 12 is created by consecutive deposition steps on a sacrificial spherical particle creating an object surrounding a spherical void, as described herein. The exterior region 16 is illustrated as the outer layer and forms the hydrophobic exterior region. The interior region 14 forms the interior hydrophilic region of the drop-carrier particle 12. Aqueous solution is isolated and protected within the interior region 14 in contact with the interior hydrophilic material when mixed with aqueous solution and oil. FIG. 10B illustrates a sectional view in order see the internal structure of the interior region 14 of the drop-carrier particle 12.

Figure 11A:
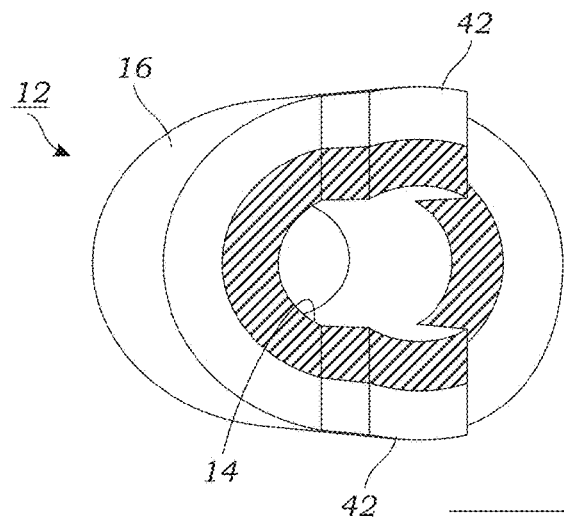
FIG. 11A illustrates a perspective view of a drop-carrier particle according to another embodiment. The drop-carrier particle contains tabs or flaps that are flexible and move in response to the presence of a liquid droplet contained inside the drop-carrier particle.
Figure 11B:
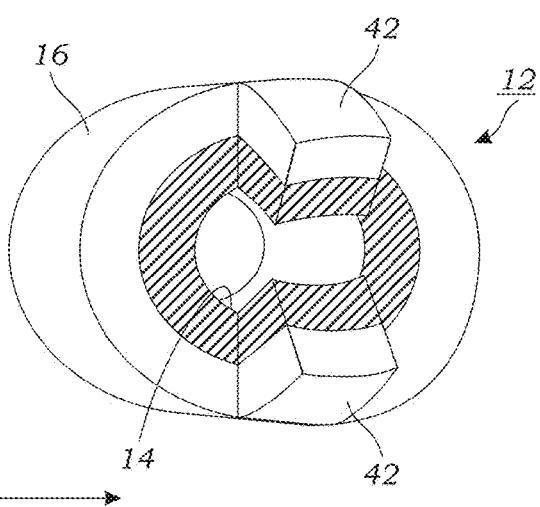
FIG. 11B illustrates a perspective view of a drop-carrier particle of FIG. 11A with the tabs or flaps shown in a flexible state after a fluid droplet has been loaded into the interior of the drop-carrier particle (the droplet is omitted for clarity purposes).

FIGS. 11A-11B illustrates another embodiment of a drop-carrier particle 12. In this embodiment, the drop-carrier particle 12 includes tabs or flaps 42. The tabs or flaps 42 are flexible and move in response to interfacial tension of the fluid droplet 18 when located in the drop-carrier particle 12 (fluid droplet not illustrated inside drop-carrier particle 12 in FIGS. 11A, 11B). The exterior region 16 forms the hydrophobic exterior region. The interior region 14 forms the interior hydrophilic region of the drop-carrier particle 12 and is where the fluid droplet 18 is held when loaded therein. In this embodiment, upon encapsulating an aqueous fluid droplet 18 within the interior region 14 of the drop-carrier particle 12, the flexible tabs or flaps 42 bends from the state of FIG. 11A to the state of FIG. 11B (in the direction of arrow A) due to the interfacial tension of the aqueous fluid droplet 18 with the exterior hydrophobic phase. The bent shape minimizes the total energy of the system including elastic and interfacial energy.

Figure 11C:
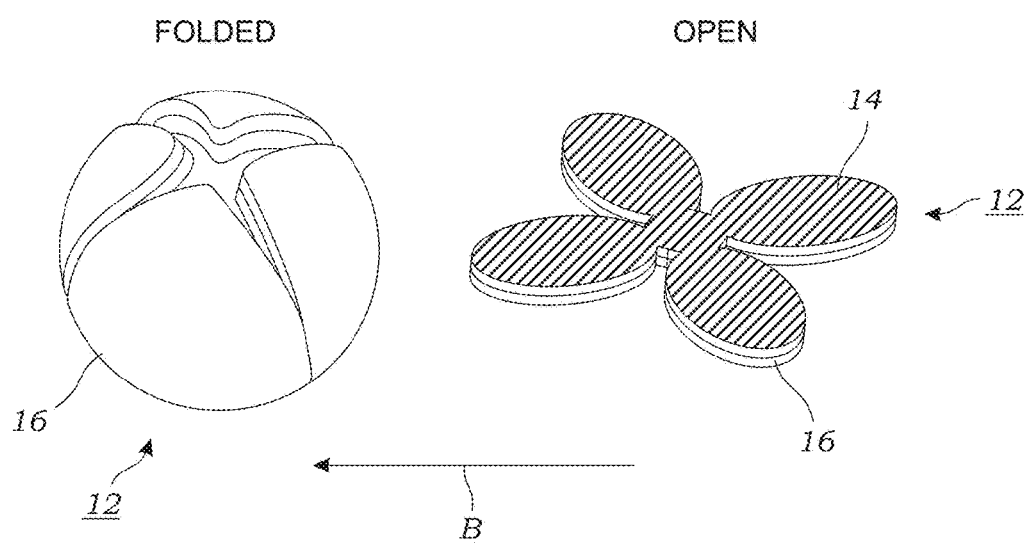
FIG. 11C illustrates a perspective view of a drop-carrier particle according to another embodiment. The drop-carrier particle is illustrated in an "open" configuration prior to encapsulation of a fluid droplet and the "folded" configuration where the tabs or flaps fold around the fluid droplet contained therein (the droplet is omitted for clarity purposes).

FIG. 11C illustrates another embodiment of a drop-carrier particle 12. In this embodiment, the drop-carrier particle 12 has a plurality of tabs or flaps 42 that resemble flower petals that fold around the fluid droplet 18 (not illustrated) when encapsulating the aqueous phase. Arrow B illustrates how the drop-carrier 12 tabs or flaps 42 that contain the hydrophilic interior region 14-fold to envelope and encapsulate the aqueous phase. The hydrophobic exterior region 16 is maintained on the outside of the drop-carrier particle 12 after folding. This embodiment can be fabricated using standard surface micromachining and photolithography processes known in the art to create multilayered 2D structures using masking with a photoresist layer. For example, a sacrificial layer is spin coated on a wafer (e.g., dextran solution) followed by evaporation of a gold layer (e.g., 100 nm) and chemical vapor deposition of a silicon dioxide layer (100 nm) (optionally including an adhesion layer between silicon dioxide and gold, e.g., titanium 10 nm). The three-layer structure is photopatterned in the 2D shape shown unfolded in FIG. 11C, and the silicon dioxide and gold layers are etched. The dextran layer is then released in water to release the 2-layer gold-silicon dioxide particle. The gold layer 16 is then coated with self-assembled monolayers to impart hydrophobic (using alkylthiol) or fluorophilic (perfluoralkylthiol) properties to the exterior layer 16. The silicon dioxide hydrophilic interior layer 14 can then interact with aqueous solutions. In addition to evaporation and chemical vapor deposition processes, spin-coating or dip-coating of polymer materials with different surface properties or reactivity can be used to create the multi-layer structure.

The drop-carrier particles 12 can be designed in a manner such that bending around one or more axes requires reduced force by including thinned regions or regions with long lever arms (e.g., tabs or flaps 42) that can bend with lower applied forces and torques. Drop-carrier particles 12 can also be designed to fold-up along more than one axis such as in origami folding to support interior aqueous droplets 18 that predominantly only interact with an interior region 14 hydrophilic phase. Drop-carrier particles 12 that bend to minimize interfacial energy have advantages in stabilizing particle-drops 20 once they are formed by undergoing this shape change which would require a higher activation energy due to thermal, mechanical or chemical means to overcome. Additionally, there is less exposed surface area of the internal aqueous phase for interaction, further stabilizing the interior droplet 18.

Figure 12A:
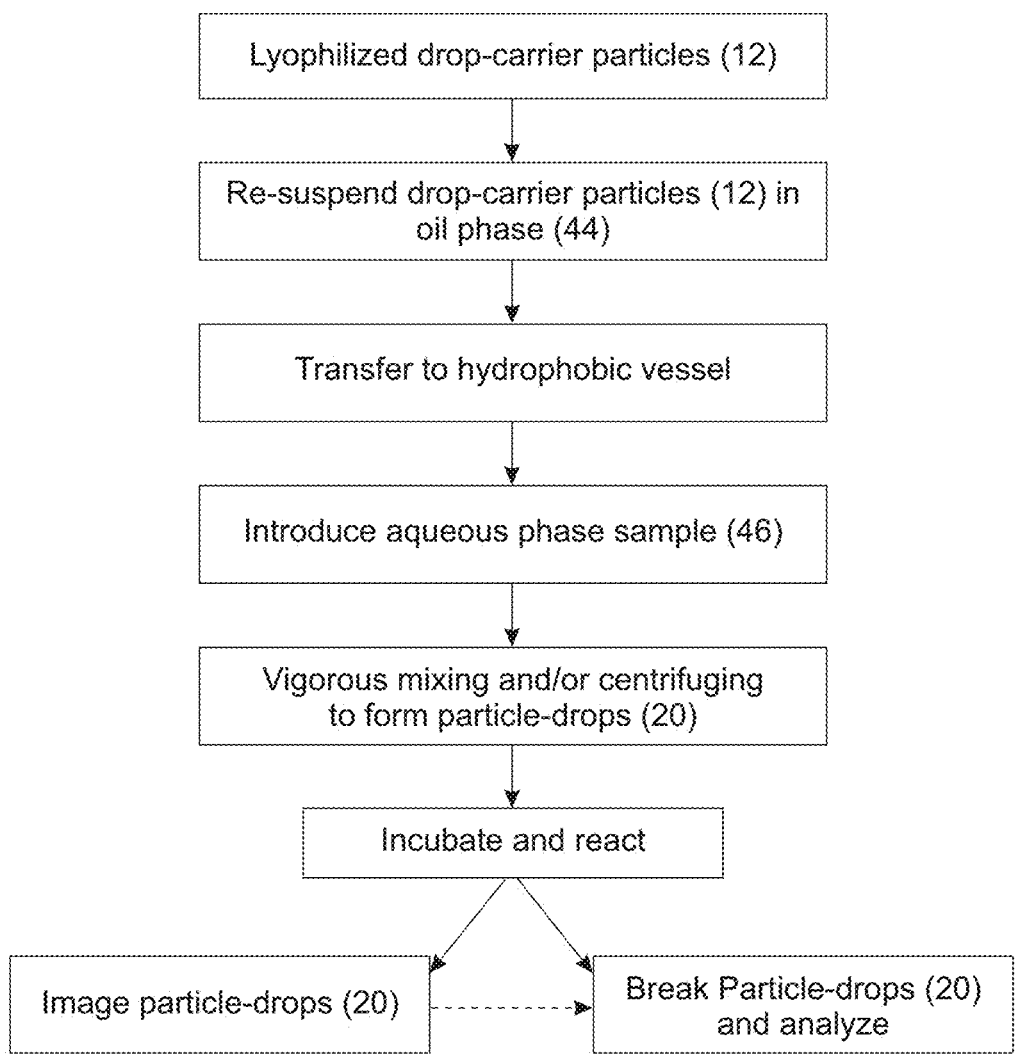
FIG. 12A illustrates an illustrative process for loading drop-carrier particles with fluid droplets to generate particle-drops. The particle-drops may then be subsequently used for reactions followed by imaging and/or analysis of the contents contained in the fluid droplets.

FIG. 12A illustrates an illustrative process for loading drop-carrier particles 12 with fluid droplets 18 to generate particle-drops 20. In this embodiment, lyophilized powder of drop-carrier particles 12 are re-suspended in an oil phase 44. This may include, by way of example, toluene, decanol, polypropylene glycol, lauryl alcohol, botanical oils, light mineral oil, heavy mineral oil, silicone oil, fluorinated oil (e.g., Fluorinert™ FC40, Novec™ 7500, Krytox™ oils). Next, the re-suspended drop-carrier particles 12 are transferred to a hydrophobic vessel (e.g., a Rain-X® coated glass vial, or low adhesion microwell plate). Next, the aqueous sample 46 is introduced. The aqueous sample 46 may contain analytes, reagents, biomolecules, stains, dyes, reporters that are to be loaded into the fluid droplet 18 volume that is loaded in the drop-carrier particle 12. As seen in FIG. 12A, the particle and aqueous suspension is then mixed and/or vortexed. The mixture is then subject to centrifugation to load the aqueous phase (i.e., fluid droplets 18) into the drop-carrier particles 12 to form particle-drops 20 suspended in the continuous oil phase. Optionally, if the particle-drop 20 is magnetic, an externally applied magnetic field can be used to mix the suspension and pull particle-drops into the continuous phase. While FIG. 12A describes the drop-carrier particles 12 first being re-suspended in an oil phase 44 prior to introduction of the aqueous sample 46, the order may be reversed. For example, the drop-carrier particles 12 may be added first to the aqueous sample 46 followed by introduction of the oil phase 44. As seen in FIG. 12A, the now formed particle-drops 20 may be used in one or more assays described herein. This may include incubation and reaction of the particle-drops 20 alone or the exchange or dilution with a new aqueous solution. Free drops of aqueous sample 46 not associated with drop-carrier particles 12 can be removed from the top of the vessel due to a difference in density or size (due to drop coalescence) compared to particle-drops 20. After reaction, the particle-drops 20 may be imaged using one or more of the imaging modalities described herein. The particle-drops 20 may also be merged into a larger aqueous solution after the reaction (or after imaging) and subject to analysis as described in detail herein.

In one illustrative embodiment, particle-drops 12 may be generated in four (4) steps. First, drop-carrier particles 12 are taken out of particle stock solution and dried to remove ethanol. Second, drop-carrier particles 12 are resuspended in a proper oil phase solution, which has significant difference in interfacial energy between hydrophilic and hydrophobic layers. There are several options of organic solutions for the oil phase, including a toluene-ethanol-mix (ratio of 20:3), decanol, and PPGDA. The particle-laden oil suspension is transferred to a 20 mL glass vial, which is treated by Rain-X® coating for two (2) days. Third, an aqueous phase (water) with a volume of the same order of magnitude as the multiplication of the drop-carrier particle 12 number and each individual cavity or void 24 volume for a drop-carrier particle 12 is injected into the oil solution. Similarly, the integrated cavity or void volumes for a plurality of drop-carrier particles 12 can also be matched to a target aqueous sample volume. The combined solution is then pipetted up and down vigorously. Fourth, the vial is centrifuged for five (5) minutes at 2000 rpm to bring the aqueous solution into the cavities of the drop-carrier particles 12, generating particle-drops 20 that settle on the bottom of the glass vial.

The particle-drops 20, in one embodiment, can then be incubated and reacted with one or more reactants. These reactants may be contained in separate aqueous solutions that the particle-drops 20 can be passed through or exposed to (e.g., to capture molecules or cells of interest with affinity reagents). Additional solutions may be exchanged that contain reagents or washes. The particle-drops 20 can then be subject to optical readout. For example, the particle-drops 20 may be on an optically transparent substrate such as glass or the like and imaged with an imaging device. The particle-drops 20 may also be loaded into wells in a microtiter plate or the like which can then be visualized. In some embodiments, the particle-drops 20 may be run through a conventional flow cytometer or fluorescence activated cell sorter (FACS) for the screening and sorting of particle-drops 20. Alternatively, the emulsions can be broken and then molecules contained therein amplified and/or analyzed using various optical or nucleic acid sequence-specific detection schemes.

Figure 12B:
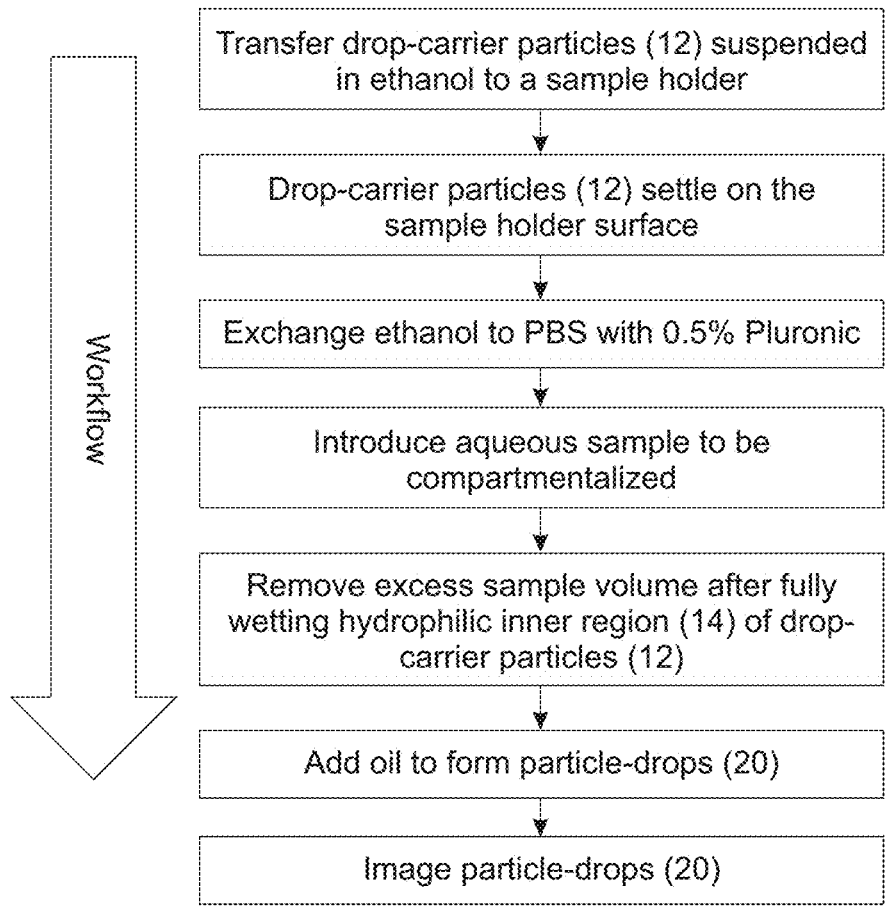
FIG. 12B illustrates another illustrative process for loading drop-carrier particles with fluid droplets to generate particle-drops. The particle-drops may then be subsequently used for reactions followed by imaging and/or analysis of the contents contained in the fluid droplets.

FIG. 12B illustrates an exemplary process for loading drop-carrier particles 12 with fluid droplets 18 to generate particle-drops 20 according to another embodiment. In this embodiment, the drop-carrier particles 12 are suspended in ethanol and transferred to one or more sample holders. This may include, for example, a tube or well of a well plate. In some instances, the sample holder may also be a substantially flat substrate (e.g., slide). The sample holder preferably has a hydrophobic surface. The drop-carrier particles 12 are allowed to naturally settle on the surface of the sample holder. The ethanol is then exchanged with PBS with 0.5% v/v Pluronic (PBSP). Next, an aqueous sample that is to be compartmentalized is introduced to the drop-carrier particles 12 (e.g., added to sample holder). Excess sample volume is then optionally removed after fully wetting the hydrophilic interior region 14 of the drop-carrier particles 12. Finally, oil is added as the continuous phase to form particle-drops 20. The particle-drops 20 may then be imaged. Note that imaging may be performed immediately after particle-drop 20 formation or, alternatively, after a period of incubation has elapsed. Imaging of the particle-drops 20 may include imaging the particle-drops 20 with a fluorescence and/or bright-field microscope.

Figure 12C:
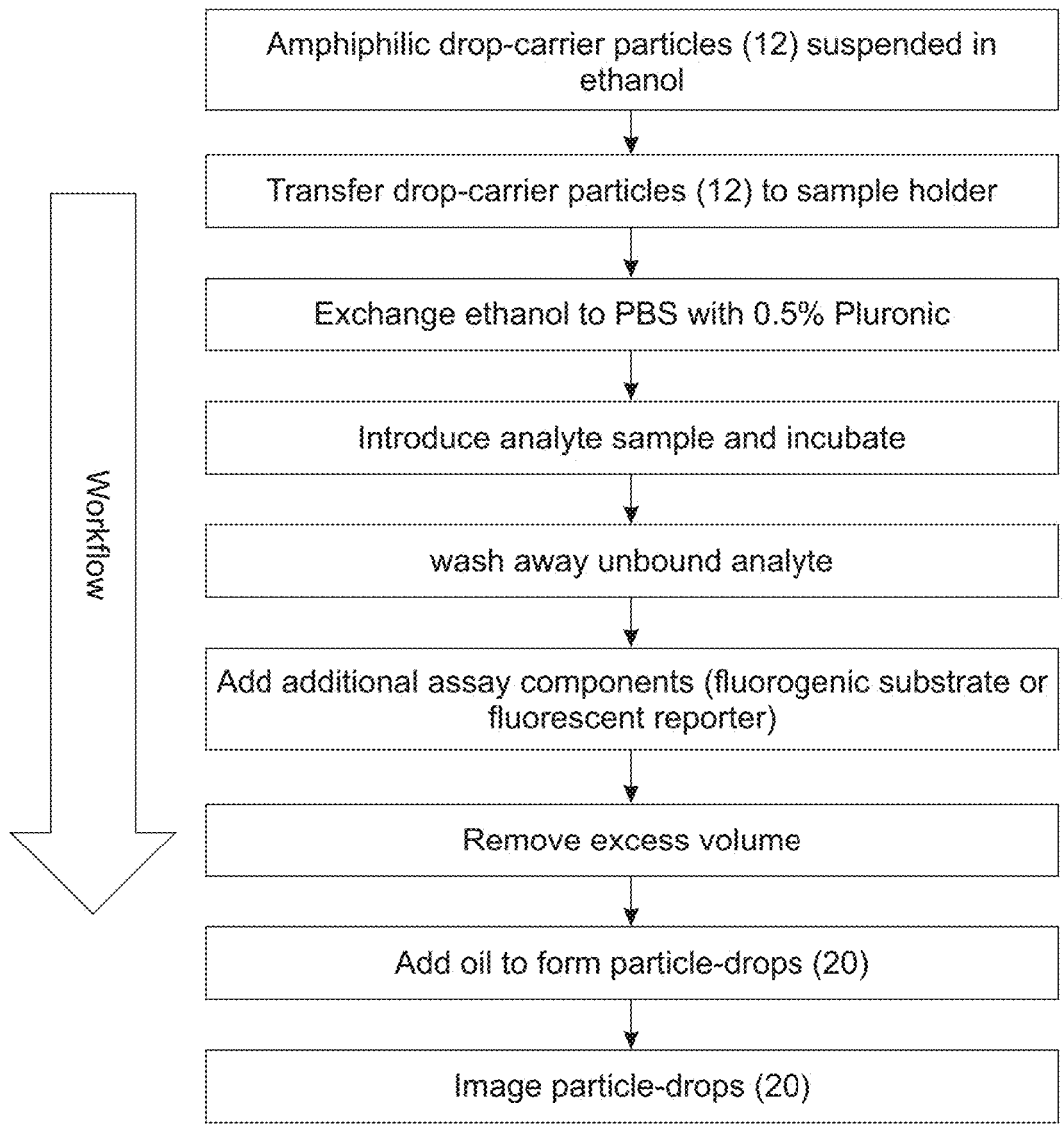
FIG. 12C illustrates another illustrative process for loading drop-carrier particles with fluid droplets to generate particle-drops. The particle-drops may then be subsequently used for reactions followed by imaging and/or analysis of the contents contained in the fluid droplets.

FIG. 12C illustrates an exemplary process for loading drop-carrier particles 12 with fluid droplets 18 to generate particle-drops 20, for example, that are used in an assay according to another embodiment. In this embodiment, the drop-carrier particles 12 are suspended in ethanol and transferred to one or more sample holders (e.g., tube, well, slide, as disclosed above in the context of FIG. 12B). This may include, for example, a tube or well of a well plate. In some instances, the sample holder may also be a substantially flat substrate (e.g., slide). The sample holder preferably has a hydrophobic surface. The drop-carrier particles 12 are allowed to naturally settle on the surface of the sample holder. The ethanol is then exchanged with PBS with 0.5% v/v Pluronic. Next, an aqueous sample that is to be compartmentalized (and contains the analyte or other assay component) is introduced to the drop-carrier particles 12 (e.g., added to sample holder) and allowed to incubate. A wash step (e.g., using a buffer or the like) is performed to wash away unbound or non-compartmentalized analyte). Additional assay components are then added. This may include, for example, a fluorogenic substrate, chromogenic substrate, or fluorescent reporter. Finally, oil is added as the continuous phase to form particle-drops 20. For example, one example of a fluorogenic substrate includes the QuantaRed™ Enhanced Chemifluorescent HRP Substrate Kit, available from ThermoFisher Scientific (Catalog Number: 15159). The particle-drops 20 may then be imaged.

There are no commercially available particles with the desired characteristics or commercially available manufacturing methods for particles in the sub-millimeter length scale. The drop-carrier particles 12 described herein can be manufactured using a novel fabrication method, called high-throughput Optical Transient Liquid Molding (OTLM). In this method, microfluidic posts, pillars, or other protuberances are formed in a microfluidic channel and used to generate complex sub-millimeter scale particles with shapes that consist of the orthogonal intersection of horizontally and vertically-extruded 2D patterns in a high-speed manner. An example of OTLM particle fabrication techniques is found in International Patent Application Publication No. WO/2017059367, which is incorporated herein by reference.

The horizontally and vertically-extruded 2D patterns are respectively determined by the cross-sectional shape of a flowstream of photo-crosslinkable polymer pre-cursor and the shape of an optical mask that is used to generate the other orthogonal cross-section. Inertial flow engineering is used to sculpt a single-phase flow stream into a complex and cross-sectional shape in a microchannel using the flow past a sequence of defined microstructures. The shape of the sculpted flow may be user-defined and programmed using software to define the microfluidic channel with the particular micropillar sequence necessary to create the final shape. For example, Wu et al., which is incorporated by reference herein, describe a software uFlow (available at http://bio-microfluidics.com/software.php) that allows for the design of 2D flow shapes with a simple graphical user interface (GUI) that can be used to predict and design particle shapes. See Wu et al., Rapid Software-Based Design and Optical Transient Liquid Molding of Microparticles, Adv. Materials, 27, pp. 7970-78 (2015).

Flowing through this microstructured channel creates a sculpted flow stream. The flow is then stopped using a pinch valve and the stream is illuminated using patterned UV light through an optical mask to achieve a complex 3D drop-carrier particle 12. Automated control and microchannel design with an elongated illumination region downstream allows for a high production rate of ~36,000 drop-carrier particles 12 per hour. Several embodiments of the drop-carrier particles 12 require concentric enclosed topologies, which can be achieved in a flow stream using recirculating secondary flows around offset pillars or posts 58. Another flow channel design which achieves recirculating secondary flows which can be used for creating the concentric enclosed topology is a curving channel in which Dean flow creates circulation. These designs allow bending of the initial main co-flow from straight co-flowing regions to 2D full or partial encapsulation patterns consisting of concentric hydrophilic and hydrophobic layers. In one embodiment, the inner region 14 that holds a liquid compartment is formed in the flow stream by deforming a precursor co-flow with hydrophilic and hydrophobic polymer precursors that are flowing side by side into a curved or encapsulated shape with concentric regions consisting of an interior void, hydrophilic, and hydrophobic layers. The orthogonal UV exposure pattern with protruding shapes is designed to avoid the aggregation of drop-carrier particles 12 or introduce physical shape-based indicia 40. This pattern is exposed through a mask 64 which contains the repeating pattern in a row along the flow direction to make many identical drop-carrier particles 12.

Designs can include protruding shapes that avoid the aggregation of drop-carrier particles 12, structured tabs, flaps, or overhangs 42 that optimize surface energy of particle-drops 20, or indicia 40 for specific sets of drop-carrier particles 12 with unique chemical properties. Following synthesis, drop-carrier particles 12 can be stored as a dried or lyophilized powder or as a suspension in oil or aqueous solution. These complex 3D shapes are not possible with approaches like stop-flow lithography, and unlike stop-flow lithography which requires an oxygen quenching layer that prevents polymerized particles from sticking to the microchannel wall, the OTLM method enables fabrication of particles without an oxygen inhibition layer or specific channel wall materials that provide such a layer because the pre-polymer solution is sculpted to occupy regions away from the channel walls.

Figure 13A:
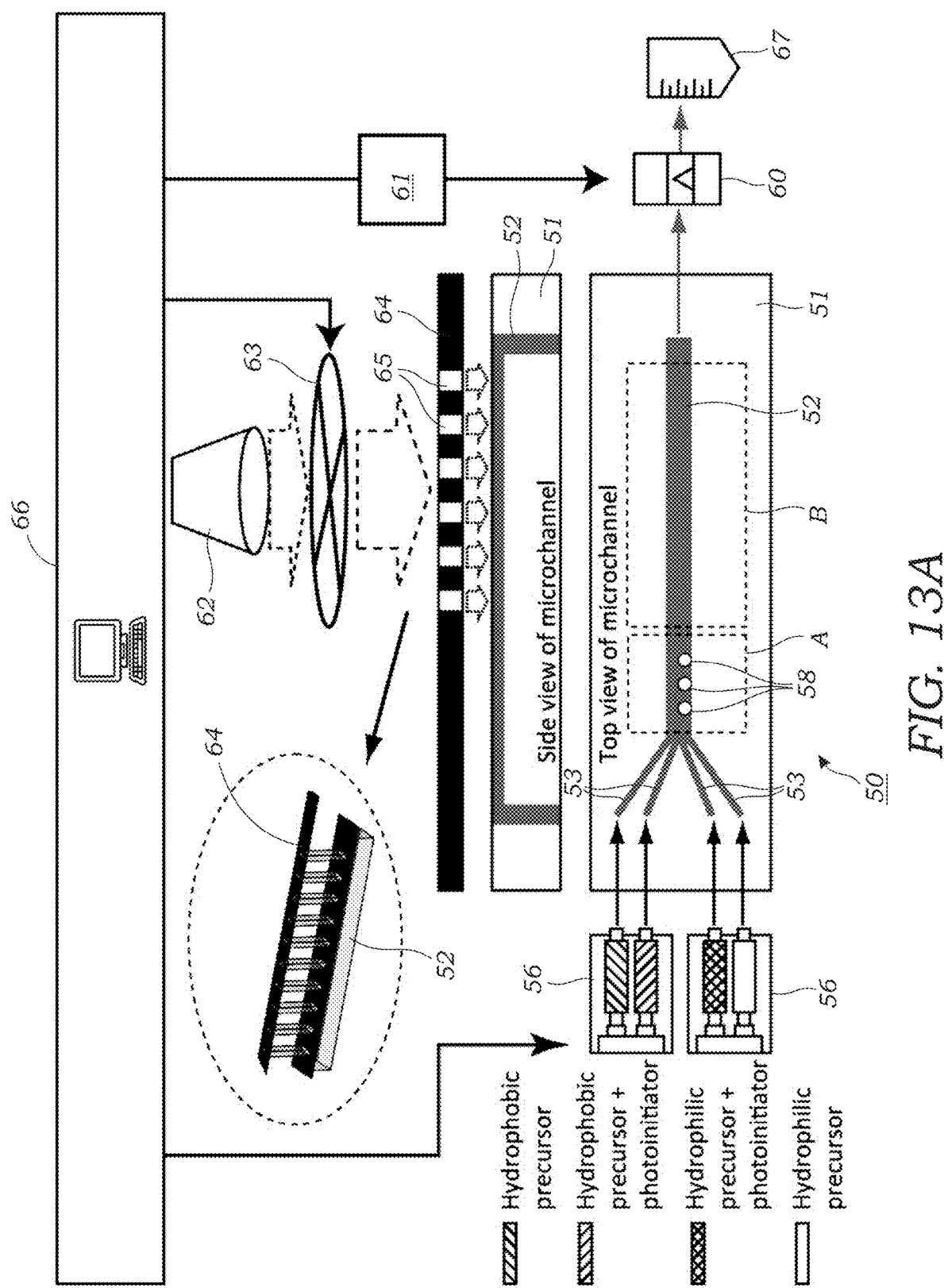
FIG. 13A illustrates a schematic or system level view of a microfluidic-based system for the Optical Transient Liquid Molding (OTLM) fabrication of drop-carrier particles according to one embodiment.

FIG. 13A illustrates a schematic or system level view of a microfluidic-based system 50 for the OTLM fabrication of drop-carrier particles 12. The system 50 includes a microfluidic device 51 that includes a microfluidic channel 52 formed therein that includes a plurality of input channels 53 that, as explained herein, are used to deliver various polymer precursor components needed to make the final drop-carrier particles 12. The precursor components include, for example, a hydrophilic precursor polymer, a hydrophobic precursor polymer, and a photoinitiator mixed with both solutions. As seen in FIG. 13A, one or more syringe pumps 56 are used to pump the pre-polymer components and photoinitiator/pre-polymer mixtures into the microfluidic channel 52. The microfluidic channel 52 includes a sequence of posts or pillars 58 located in an upstream region A of the microfluidic channel 52 that, collectively, are used to generate the sculpted flow. The downstream region B of the microfluidic channel 52 is where ultraviolet light exposure takes place to crosslink the precursor polymers to form the drop-carrier particles 12. The outlet of the microfluidic channel 52 is coupled to a pinch valve 60 operated by a microcontroller 61 that is actuated to stop flow within the microfluidic channel 52 during the light exposure step as described below. After the drop-carrier particles 12 are formed during the crosslinking process, the drop-carrier particles are collected in a collection vessel 67 (e.g., vial). An ultraviolet collimated light source 62 is provided and illuminates a mask 64 with a computer-controlled shutter 63. The mask 64 includes one or more specifically shaped holes or apertures 65 (multiple drop-carrier particles 12 can be formed from a single exposure) formed therein that is used to define the shape of the drop-carrier particle 12 along one orthogonal axis. In some embodiments, the mask 64 may be secured to a z-adjust stage to control the size of the UV light projection on the shaped flow. The microfluidic channel 52 (or microfluidic device 51 that contains the microfluidic channel 52) may include a xy-translation/rotation stage to align the microfluidic channel 52 with the UV crosslinking optical path defined by the plurality of apertures 65 in the mask 64. A computer 66 is provided with software loaded thereon (e.g., Lab VIEW™) that interfaces with and controls the syringe pump(s) 56, pinch valve 60 (via microcontroller 61), and collimated ultraviolet light source 62, shutter 63.

In one embodiment, to generate a concentric hydrophilic interior/hydrophobic exterior shape in the cross section of the polymer precursor stream, a co-flow with four (4) fluid streams, which include poly(propylene glycol) diacrylate (PPGDA, MW~800) (the hydrophobic precursor in FIG. 13A), PPGDA added with photoinitiator (PI, 2-hydroxy-2-methylpropiophenone) (the hydrophobic precursor+PI in FIG. 13A), poly(ethylene glycol) diacrylate (PEGDA, MW~575) added with PI (the hydrophilic precursor+PI in FIG. 13A), and PEGDA (the hydrophilic precursor in FIG. 13A). In this embodiment, these inputs are pumped into the microfluidic channel 52 with designed microstructures, e.g., posts or pillars 58. The microfluidic channel 52 has, in one embodiment, a width of 1200 micrometers and a height of 300 micrometers, while the microstructures consist of six (6) pillars in series each having a diameter of 600 micrometers. The microfluidic channel 52 with the posts or pillars 58 is made up entirely with the same material, which is polydimethylsiloxane (PDMS) so the wetting properties of interface between PPGDA and PEGDA is the same on top and bottom walls and the deformation of the flow stream is symmetrical in terms of the middle plane of the microfluidic channel 52.

In another embodiment, the hydrophilic precursor may include PEGDA while the hydrophobic precursor may include 1,6-Hexanediol diacrylate (HDA), (CAS No. 13048-33-4, available from Sigma-Aldrich, product number 246816). PEGDA and HDA are used with an ultraviolet crosslinked transparent thiolene-based optical adhesive, NOA89 available from Norland Products, Inc. which is also used as the photoinitiator. Thus, with reference to FIG. 13A, the order of the four (4) input streams from top to bottom includes: HDA (top syringe), NOA89 (second from top syringe), PEGDA+2-hydroxy-2-methylpropiophenone (second from bottom syringe), and PEGDA (bottom syringe).

In another embodiment, the hydrophilic precursor may include PEGDA while the hydrophobic precursor may include a mixture of HDA and lauryl acrylate (CAS No. 2156-97-0, available from Sigma-Aldrich, product number 447315) with lauryl acrylate ranging from between 0 to 60% of the mixture on a volume basis. The photoinitiator (PI) used in this embodiment is 2-hydroxy-2-methylpropiophenone (CAS No. 7473-98-5, Darocur 1173, product number 405655, Sigma-Aldrich). Thus, with reference to FIG. 13A, the order of the four (4) input streams from top to bottom includes: HDA+lauryl acrylate (top syringe), HDA+lauryl acrylate+PI (second from top syringe), PEGDA+PI (second from bottom syringe), and PEGDA (bottom syringe).

A standard soft lithography process known to those skilled in the art is utilized to make the sealed microfluidic channel 52 with a modification of the bottom material, which is a glass slide having a 1 mm thickness with a thin (e.g., less than 100 microns) layer of PDMS. The flow rate of the hydrophilic portion (PEGDA+PI) is designed to be one fourth of the hydrophobic portion (PPGDA+PI) so particle-drops 20 formed inside the cavity or void 24 can be preferentially surrounded and protected by an exterior hydrophobic layer. The PPGDA and PEGDA solutions used are diluted in ethanol to become 90 and 60 percentage of the polymer precursor respectively to match the liquid density and reduce the viscosity and the flow resistance required to drive the flow (i.e., volume fraction of PEGDA:ethanol=60:40 and PPGDA:ethanol=90:10).

To simultaneously photo-crosslink the two polymer regions, the curing time for PPGDA and PEGDA is optimized to be within one (1) second by adding 1.32 and 2.60 percentage of PI respectively. The flow rates of PPGDA, PPGDA+photoinitiator, PEGDA+photoinitiator, and PEGDA are 1.6, 1.6, 0.4, and 0.4 mL/min respectively. In addition to the design of the polymer precursor cross-section, there are an infinite degrees of freedom to design the second pattern exposed on top of the flow stream to determine the final 3D shape of the drop-carrier particles 12. The shape of the optical mask 64 for one demonstration is designed to be a rectangular slit with dimensions of 140 micrometers parallel to the flow direction and 600 micrometers perpendicular to the flow direction respectively. There are more than a hundred transparent apertures 65 (e.g., slits) designed to be in an array on a chrome mask 64. To accelerate the speed of photopolymerization of PPGDA and PEGDA, the power of UV light source 62, which is collimated by an adaptor, is designed to be ~4 W/cm$^2$ on the optical mask 64.

In one embodiment, the microfluidic channel 52 is placed on the stage upside down. The inlet and outlet are connected to syringes installed on the syringe pumps 56 and pinch valve 60, respectively. The optical mask 64 fixed with the holder is moved down using the z-translation axis to make contact with the glass of the microfluidic channel 52 with hard contact. The angle and xy location of the stage are tuned to ensure every slit is located along the same designed lateral position of the flow stream, i.e., the microfluidic channel 52. Once all static alignments are finished, the polymer liquid precursor is pumped to start dynamic particle fabrication. In one embodiment, two syringe pumps 56 are utilized to introduce the four (4) streams into the microfluidic channel 52 at total flow rate of 4 mL/min to develop a precursor stream with concentric cross section. After five (5) minutes of flow to reach steady and fully developed channel flow, the pumps 56 are stopped and within ~100 micro seconds the pinch valve 60 downstream squeezes the tubing connecting to the outlet of the microfluidic channel 52 to fully stop the flow in ~1 second. The shutter opens for one (1) second to apply a short period of UV exposure in the area of slits. Next, the pinch valve 60 is released and the pumps 56 are re-started to push the liquid again to re-develop the flow stream in the microfluidic channel 52. The operation above is repeated multiple times by an automated Lab VIEW™ program until the desired numbers of the drop-carrier particles 12 are reached.

After in-channel fabrication, all drop-carrier particles 12 are flushed out of the microfluidic channel 52 and collected together with waste of uncured precursor in a downstream vessel 67 such as a 50 mL conical tube. All drop-carrier particles 12 are purified by going through at least four (4) washes (including the time when the drop-carrier particles 12 are in the waste liquid) in ethanol. The rinse process includes centrifuging the tube to bring all drop-carrier particles 12 down to the bottom, removing the supernatant gently to avoid taking out liquid with drop-carrier particles 12, and then flushing the tube with 40~50 mL ethanol. Later, the drop-carrier particles 12 are stored in ethanol at room temperature as a particle stock solution. There is no significant degradation and loss of functionality over more than two months of storage.

The hydrophilicity/hydrophobicity of the drop-carrier particles 12 can be optimized by changing the type or concentration of the precursor monomer. There are two main design variables for the photo-crosslinkable materials in the precursor co-flow which yield tradeoffs in the fabrication system: liquid viscosity and surface tension. Pure liquid precursors have generally high viscosity which increases the pressure to drive the flow sufficiently fast to achieve inertial flow shaping. Diluting the polymer precursors in solvents can reduce viscosity but hydrophilic and hydrophobic precursors are typically immiscible to each other once diluted in appropriate solvents. Alternative approaches to shape viscous polymer precursor streams at lower flow rates using herringbone or slanted grooves in the upper or bottom walls of the microfluidic channel 52 can also be used. These structured microfluidic channels 52 can create circulating flows at lower flow rates since they do not rely on fluid inertia to shape the flow.

Figure 13B:
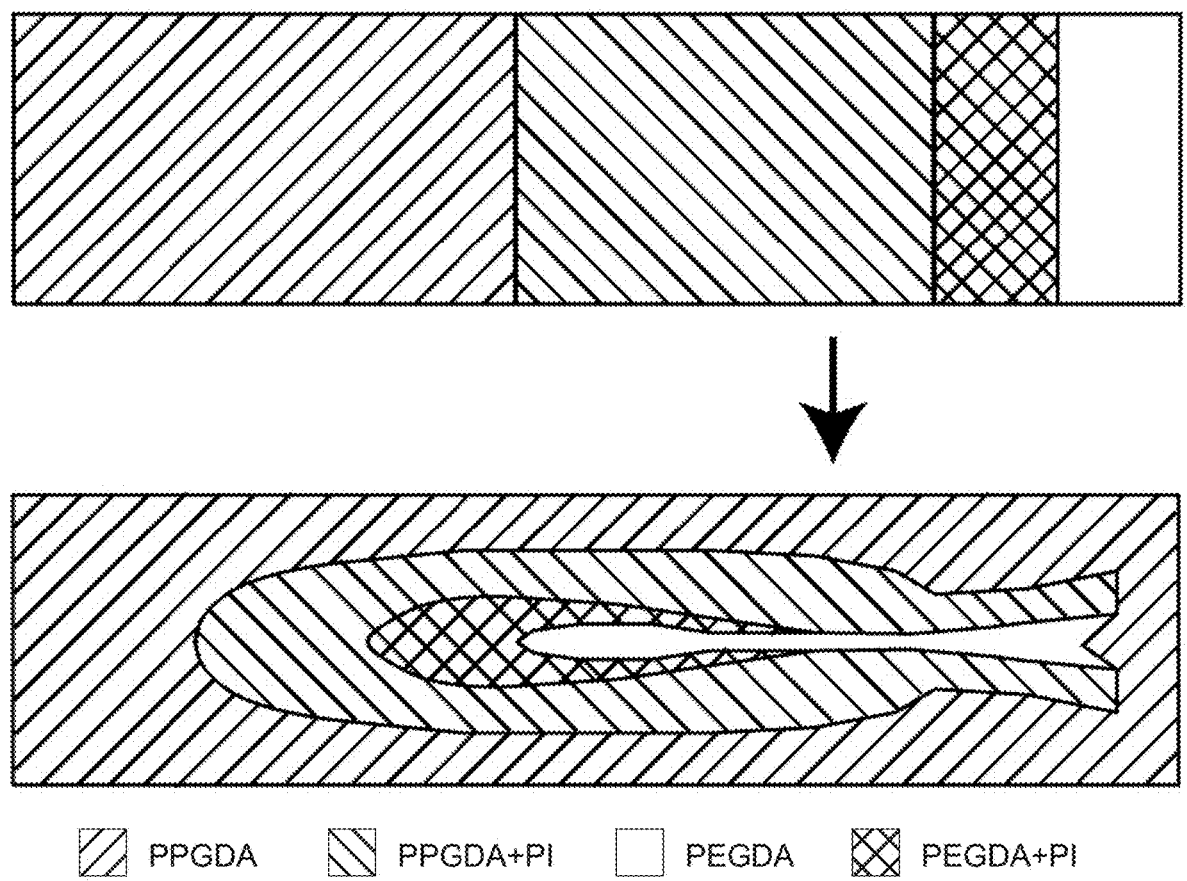
FIG. 13B illustrates the cross-sectional flow profiles for PPGDA, PPGDA+PI, PEGDA+PI, and PEGDA undergoing high-pressure co-flow in the microfluidic channel according to one embodiment.

Two solutions have been developed to design the precursor co-flow: a high-pressure flow method and a surface-energy-gradient flow method. In the high-pressure flow method, a co-flow with two miscible pure precursors (i.e. no dilution) is pumped with different hydrophilicity (e.g., poly(ethylene glycol) diacrylate/fluorinated poly(ethylene glycol) acrylate, poly(propylene glycol) diacrylate or Norland Optical Adhesive (NOA) UV adhesive) by applying higher pressure and designing a longer sequence of microstructures to provide sufficient flow deformation (a U-turn channel may be added to expand the downstream length microfluidic channel 52). FIG. 13B illustrates the cross-sectional flow profiles PPGDA, PPGDA+PI, PEGDA+PI, and PEGDA undergoing high-pressure co-flow in the microfluidic channel 52. The upper, non-shaped flow illustrates the cross-sectional profile prior to being shaped by the posts or pillars 58. The lower, shaped flow illustrates the cross-sectional profile after being shaped by the posts or pillars 58. In the surface-energy-gradient flow method, a co-flow is created with multiple flow streams where each stream is miscible or is immiscible but with a relatively low surface tension to the material streams neighboring it. The co-flow can be typically configured by merging three streams in order: diluted hydrophilic precursor, pure hydrophilic precursor (or hydrophobic precursor, miscible with each other), and diluted hydrophobic precursor.

In an alternative particle manufacturing process, if drop-carrier particles 12 cannot be manufactured using multiple materials with different hydrophobicity, or the hydrophobicity differences are not sufficient to create a stable emulsion one can use a previously demonstrated approach to create PEG particles with spatially varying chemistries and perform a second reaction after particle creation to introduce hydrophobic groups. For example, one can use PEG diacrylate co-flowed with PEG diacrylate/PEG acrylate succinimidyl carboxymethyl ester (JenKem Technology USA, Plano, TX) on the outer region. Then one can react the amine-reactive polymerized particles with long-chain amino alkanes (e.g., hexadecylamine) or amino fluoroalkanes to locally create a hydrophobic layer or shell over the outer part of the particle.

Figure 13C:
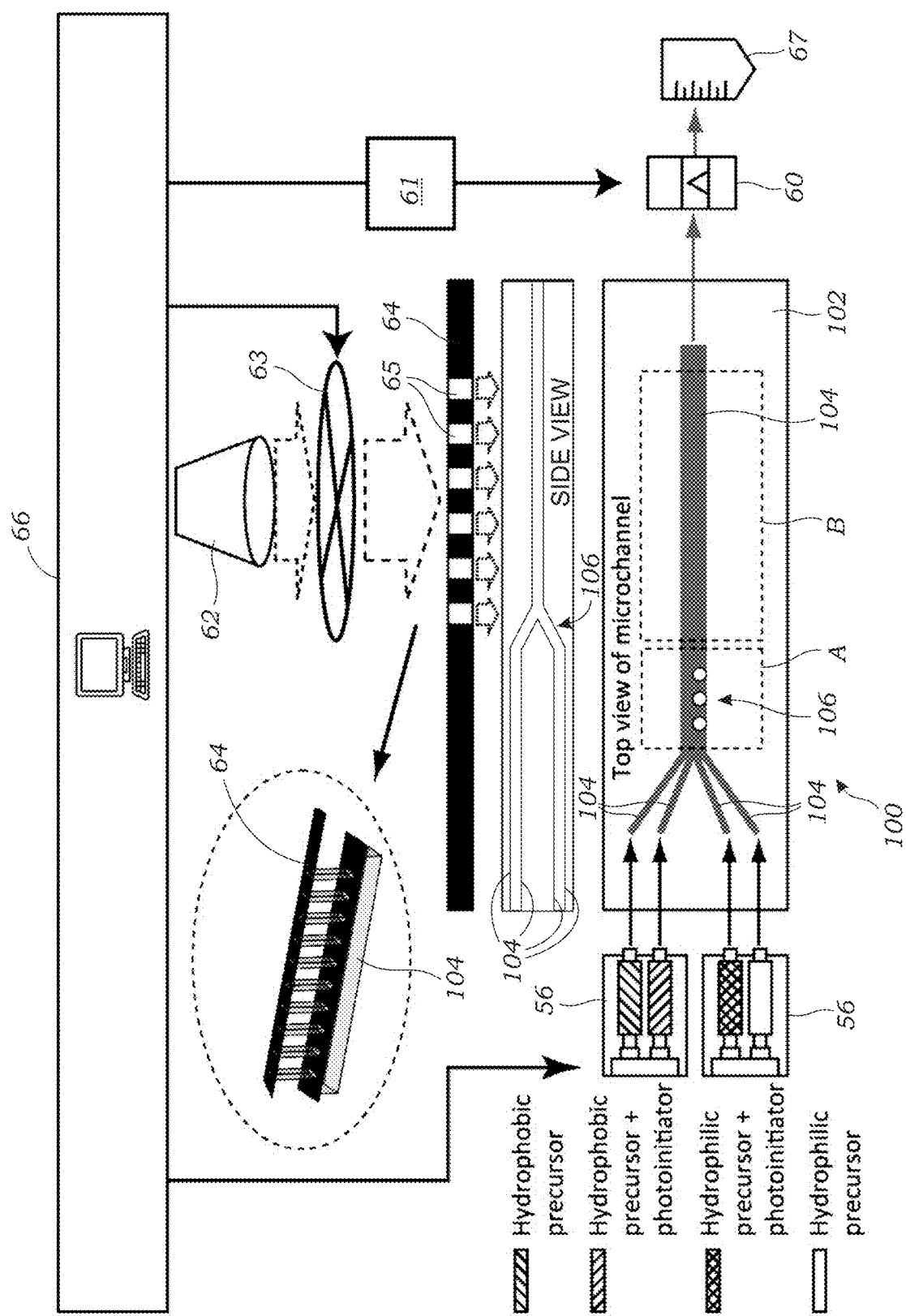
FIG. 13C illustrates a schematic or system level view of a microfluidic-based system for the fabrication of drop-carrier particles according to another embodiment. This embodiment uses a microfluidic device with non-coplanar microfluidic channels formed therein by additive manufacturing. The plurality of microfluidic channels are configured in a co-axial flow configuration where various precursor solutions co-axially surround one another in custom-sculpted cross-sectional shapes.

FIG. 13C illustrates a schematic or system level view of a microfluidic-based system 100 for the OTLM fabrication of drop-carrier particles 12. The system 100 includes a microfluidic device 102 that is fabricated using additive manufacturing techniques (e.g., three-dimensional printing) that creates non-coplanar microfluidic flow paths or channels 104 that create co-axial flow configurations 106 that allow for the creation of ring-shaped multi-material drop-carrier particles 12. The 3D-printed microfluidic device 102 may be a monolithic substrate that includes the microfluidic flow paths or channels 104 that combine to create co-axial flow configurations 106 with various cross-sectional flow profiles (see FIG. 21B) that are used to create different shapes and geometries for drop-carrier particles 12. This embodiment does not use the sequence of posts or pillars 58 found in the embodiment of FIG. 13A. Region A includes the microfluidic flow paths or channels 104 that create co-axial flow configuration(s) 106. Other than the manner of forming the sculpted flow of precursor components, this embodiment operates similarly to the embodiment of FIG. 13A as illustrated. For example, the precursor components include, for example, a hydrophilic precursor polymer, a hydrophobic precursor polymer, and a photoinitiator mixed with both solutions. Drop-carrier particles 12 are formed by stopping the flow of precursor material using a pinch valve 60 and the stream is illuminated using patterned UV light through an optical mask to crosslink the drop-carrier particle 12.

There are several benefits to the system 100 illustrated in FIG. 13C. The microfluidic device 102 can be easily manufactured using well-known additive manufacturing techniques and can easily generate ring-shaped drop-carrier particles 12. This system 100 also has significantly reduced reagent consumption by limiting the material wastage by operating at lower Reynolds number/faster refresh types. The manufacturing technique also imparts flexibility in drop-carrier 12 fabrication operation to control the size, shape, and geometric features (e.g., thicknesses, etc.) of the drop-carrier particle 12. Compared to fabrication technology utilizing a PDMS channel like that of FIG. 13A that requires clean-room facilities for the soft-lithography based fabrication, the microfluidic device 102 can be fabricated using a low viscosity liquid photopolymer (Somos® WaterShed XC 11122) for 3D printed parts that form water-resistant microfluidic flow paths or channels 104 with robust structural integrity. 3D printing technology allows for reproducible batch fabrication of the microfluidic devices 102 in a standardized manner. The need for clean-room fabrication of microfluidic channels (as required for PDMS) is eliminated thus reducing the overall cost associated with device fabrication. Moreover, the fabrication of drop-carrier particles 12 inside PDMS channels depends on oxygen permeability inside the channel which provides a polymerization inhibition layer close to the walls. However, the use of any organic solvent inside the PDMS channels swells the walls that may significantly affect the performance of the device. For the embodiment illustrated in FIG. 13C, the material (WaterShed XC 11122) used to manufacture the microfluidic devices 102 is oxygen impermeable and can be used with most fabrication materials by utilizing hydrodynamic focusing to introduce concentric inert sheath-flows 106 that provide an inhibition layer and prevents polymerization on the channel walls. The hydrodynamic focusing technique allows for on-demand control of the flow streams thus enabling size-tunable fabrication of the ring-shaped drop-carrier particles 12 without changing any additional components (e.g., the mask 64). The fabrication technique of FIG. 13A relied on inertial flows to produce 3D particle structures that required very high flow rates to run the fabrication cycles. This results in most of the reagents going to waste. However, the embodiment of FIG. 13C uses 4-fold less reagent volume for a similar throughput of the drop-carrier particles 12 per cycle. Compared to material consumption of 4 ml/min in the embodiment of FIG. 13A, the alternative fabrication method of FIG. 13C uses 1 ml/min of reagents to fabricate drop-carrier particles 12 with enhanced design flexibility in terms of the shapes and sizes of the drop-carrier particles 12. As illustrated herein, the 3D-printed microfluidic device 102 was used to generate four different shapes of drop-carrier particles 12 using four different 3D printed cross-sectional channel shapes creating concentric shaped flows 106. In addition, the size of the fabricated drop-carrier particles 12 is readily controlled by varying the inlet flow rates.

Furthermore, the flexibility of drop-carrier particle 12 design using the co-axial flow approach of FIG. 13C allows the fabrication of drop-carrier particles 12 with different outer layer/inner layer shapes and thicknesses, and tunable assay performance, such as limit-of-detection and dynamic range, for the optimal detection of target analytes. Shape-coded drop-carrier particles 12 enable signal readout using a single fluorescence channel with bright-field being used to distinguish drop-carrier particles 12 of different shapes (e.g., bright-field images may be used to better see the outer shape of the drop-carrier particle 12), without the need of multi-channel fluorescent labeling and detection, which is particularly beneficial for cost-effective assay development as well as point-of-care applications. Of course, in other embodiments, the bright-field image may be omitted and the fluorescence image being used to distinguish the shape of the drop-carrier particle 12 (e.g., the shape of the inner region 14). The development of multiplexed in vitro diagnostics of disease markers is oftentimes challenged by the detection capability over a wide range of clinical cut-offs (e.g., subpg/ml to µg/ml) using a single assay. Instead of developing a single "perfect" assay that works for all markers or concentration ranges, tunable assay performance via drop-carrier particle 12 design (e.g., larger or smaller PEG layer for trapping more or less analyte, or more or less biotinylation to change the concentration at which saturation of binding occurs) provides a simpler and more practical approach to achieve the simultaneous detection of multiple markers across a large dynamic range. Therefore, shape-coded particle-drops 20 with customizable assay performance and swarm sensing capability provide unparalleled versatility for the multiplexed detection of markers over a wide range of clinical cut-offs in a single reaction without the need for increasing the device footprint or instrumentation complexity.

The biotinylation of the interior region 14 that forms the hydrophilic contact region is demonstrated using a modified chemical composition of the precursor in which biotinylated PEG precursors may be dosed into the hydrophilic layer to allow for the attachment of affinity reagents. A biotinylation solution is made by dissolving commercially available or synthesized biotin-PEG-acrylate in ethanol with 10% (v/v) DMSO. The final precursor for in-channel fabrication is made of pure PEGDA, ethanol, and this biotinylation solution. The corresponding volume ratio depends on the degree of biotinylation for various applications but the sum of the volume of ethanol and biotinylation solution is kept to be 40% of the total volume. Alternatively, biotinylation of the drop-carrier particle 12 may occur post-fabrication.

Molecules can be added to the hydrophilic interior region 14 of the drop-carrier particles 12 through covalent linkage or electrostatic association. For example, for a polyethylene glycol based hydrophilic region, standard chemistries like NHS-esters, acrylates, vinyl-sulfones, or maleimide groups introduced into the PEG backbone can be used to covalently link DNA, proteins, fluorophores, or other molecules. Alternatively, long DNA or other molecules can be introduced during the polymerization process that remain entangled or electrostatically adsorbed to the hydrophilic polymer matrix. Similarly, drop-carrier particles 12 could be soaked into reagents to enable entry within the hydrogel matrix, prior to lyophilizing. Drop-carrier particles 12 with the same indicia 40, molecular barcodes or affinity reagents can be fabricated in a single batch and then combinations of these batches can be mixed together to obtain a mixture of drop-carrier particles 12 each with unique properties. Alternatively, molecular barcodes can be introduced into particles through split and recombine synthesis approaches to create nucleic acid barcodes.

There are several possible methods of using the particle-drops 20 to perform digital assays. Drop-carrier particles 12 starting as a lyophilized or dried powder can be added to an aqueous sample or vice versa. The quantity of drop-carrier particles 12 should be controlled such that the aqueous sample volume is approximately equal to the void volume that can be supported by the drop-carrier particles 12. This allows for the majority of the sample to be associated with the drop-carrier particles 12 without loss of sample solution (i.e., high efficiency). In some cases a smaller amount of drop-carrier particles 12 may be used if only a fraction of the sample is desired to be analyzed, or drop-carrier particles 12 include affinity reagents to capture specific molecules from the solution (e.g., proteins or antigens with antibodies or aptamers, nucleic acids with complementary sequences or poly-T sequences to capture mRNA). An oil or other hydrophobic solvent can then be added to the particle-drop 20 solution at a volume to completely surround each particle-drop 20 with the hydrophobic continuous phase solution (volume fractions of >5:1 continuous:disperse phase are best).

The sample of particle-drops 20 can then be suspended/dispersed in the continuous phase through a variety of methods. The solution could be vortexed, centrifuged, shaken or mixed. Magnetic force can be applied to pull magnetically-embedded drop-carrier particles 12 into the oil phase. If the oil phase is denser than the aqueous phase, and drop-carrier particles 12 are even more dense, they can be centrifuged to pass them into the oil phase. Suspended particle-drops 20 in the oil phase can then be reacted using reagents present in the aqueous sample solution or attached or eluting from the drop-carrier particles 12. Reactions can be initiated through thermo-cycling e.g., for digital-PCR, other temperature increases (e.g., digital LAMP), or light activation.

In some embodiments, particle-drops 20 can be passed through separate aqueous solutions to first capture molecules or cells of interest with affinity reagents and then replace solutions with reagent solutions. Particle-drops 20 can be passed between solutions using magnetic force, centrifugation, or dilution or exchange with new solutions. The reactions in particle-drops 20 can be visualized or read-out using any number of types of optical systems. The suspension of particle-drops 20 could be spread on an optically transparent slide and compressed between cover-glass to readout an optical signal from each particle-drop 20. Alternatively, the particle-drops 20 suspended in oil can be passed through a microfluidic channel and analyzed/and or sorted using flow cytometry optical setups and sorting approaches known in the art. Particle-drops 20 sized appropriately (e.g., <100 micrometers in a long dimension) can be exchanged back into an aqueous solution (with or without the addition of surfactant) to pass through standard flow cytometer systems in a related embodiment. Particle-drops 20 may also be collected in wells of a microtiter plate. Fluorescent signal for nucleic acid amplification within particle-drops 20 can be accomplished using intercalator dyes or specific molecular affinity probes with quencher/fluorophore pairs. For protein recognition, an antibody-conjugated with an enzyme that turns over a fluorogenic or chromogenic substrate can be used. Other optical readout approaches known in the art for digital assays can be used in a similar manner for Particle-drops 20. In the event that drop-carrier particles 12 coalesce, small amounts of surfactant (e.g., 0.1-1% Pluronic) can be added following formation of the particle-drop emulsion 20 to further stabilize the separate aqueous compartments.

As one alternative manufacturing method to create drop-carrier particles 12, spherical particle templates may be used to create particles of the type illustrated in FIGS. 10A and 10B. In this method, spherical particle templates are arranged on a substrate (e.g., a silicon wafer) to pack in a regular array. For example, polystyrene particles of 5 micrometers in diameter create a close packed layer on a silicon wafer substrate. A first layer of silicon dioxide is deposited using low pressure chemical vapor deposition to a thickness of 100 nm. A layer of gold (20 nm) is then evaporated on top of the silicon dioxide. The polystyrene particles are then dissolved away using a solvent (e.g., toluene) to leave a radially symmetric concentric shell structure with an internal silicon dioxide region and external gold region. The gold region or silicon dioxide region can then be selectively functionalized to impart hydrophilicity/hydrophobicity. For example, coating with a long-chain alkanethiol (10 to 16 carbon length) forms a self-assembled monolayer on the gold layer which increases hydrophobicity, while the silicon dioxide remains hydrophilic creating a drop-carrier particle 12 with amphiphilic structure that can support a droplet of aqueous fluid 18 in the internal region 14, and can be suspended in an oil phase.

Figure 14:
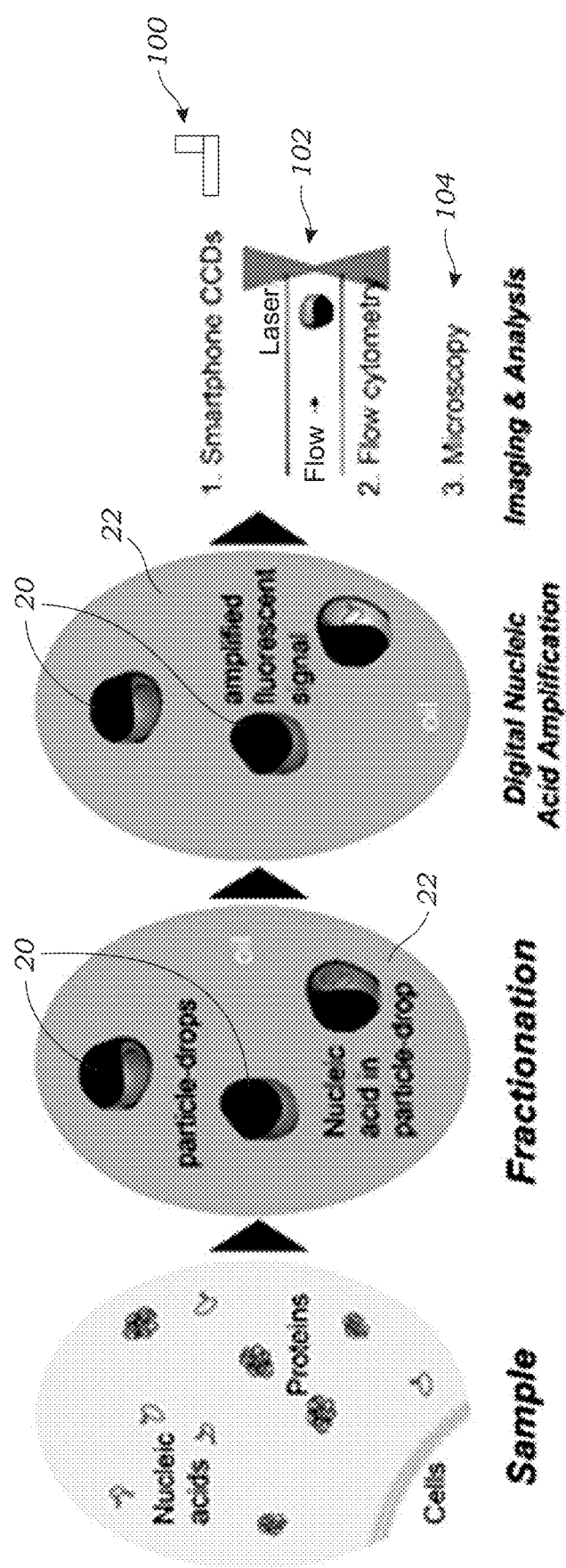
FIG. 14 illustrates one exemplary use of particle-drops for rapid digital assays of a sample. Imaging and analysis may be performed using a Smartphone-based fluorescence imager, flow cytometers, or a microscope.

FIG. 14 illustrates the use of particle-drops 20 for rapid digital assays using a sample. The sample may include cells, proteins, nucleic acids, and the like. Following rapid fractionation and exposure to the sample solution, solutions containing particle-drops 20 can be heated to perform amplification (e.g., nucleic acid amplification) and generate an optical signal (e.g., intercalator fluorescence). These signals can be read-out using low cost Smartphone-based fluorescence imagers 100 such as that disclosed in U.S. Pat. No. 9,057,702, which is incorporated by reference, traditional flow cytometers 102, or other microscope-based devices 104. For example, in one exemplary workflow, a volume-calibrated number of drop-carrier particles 12 are introduced to a reaction mix with purified nucleic acids in a tube or other sample holder. Oil is added to the tube/sample holder and emulsified by gentle mixing. The reaction is then performed in the particle-drop 20 emulsion. The particle-drops 20 can then be spread on an optically transparent substrate (e.g., slide) and imaged using, for example, a mobile-phone based fluorescence imaging device.

In some cases, e.g., single-cell barcoded RNA-seq, following nucleic acid binding it is desirable to break the emulsion and exchange solutions to perform reverse transcription and amplification of the resultant cDNA. The pool all of the barcoded products can then be used to perform a single sequencing run at low cost. Breaking of a particle-drop 20 emulsion is possible through a variety of approaches. Using photodegradable crosslinkers during the fabrication of the drop-carrier particles 12 can allow photo-induced degradation of the drop-carrier particles 12 and merging of the aqueous solutions. Alternatively, magnetic or dense drop-carrier particles 12 can be transferred into a neighboring aqueous solution within a centrifuge or micro-fuge tube using magnetic force or centrifugation. Surfactants can also be introduced to the suspension that adsorb onto the hydrophobic exterior regions 16 of the drop-carrier particles 12 to make them more hydrophilic and break the particle-drop 20 suspension.

Figure 15:
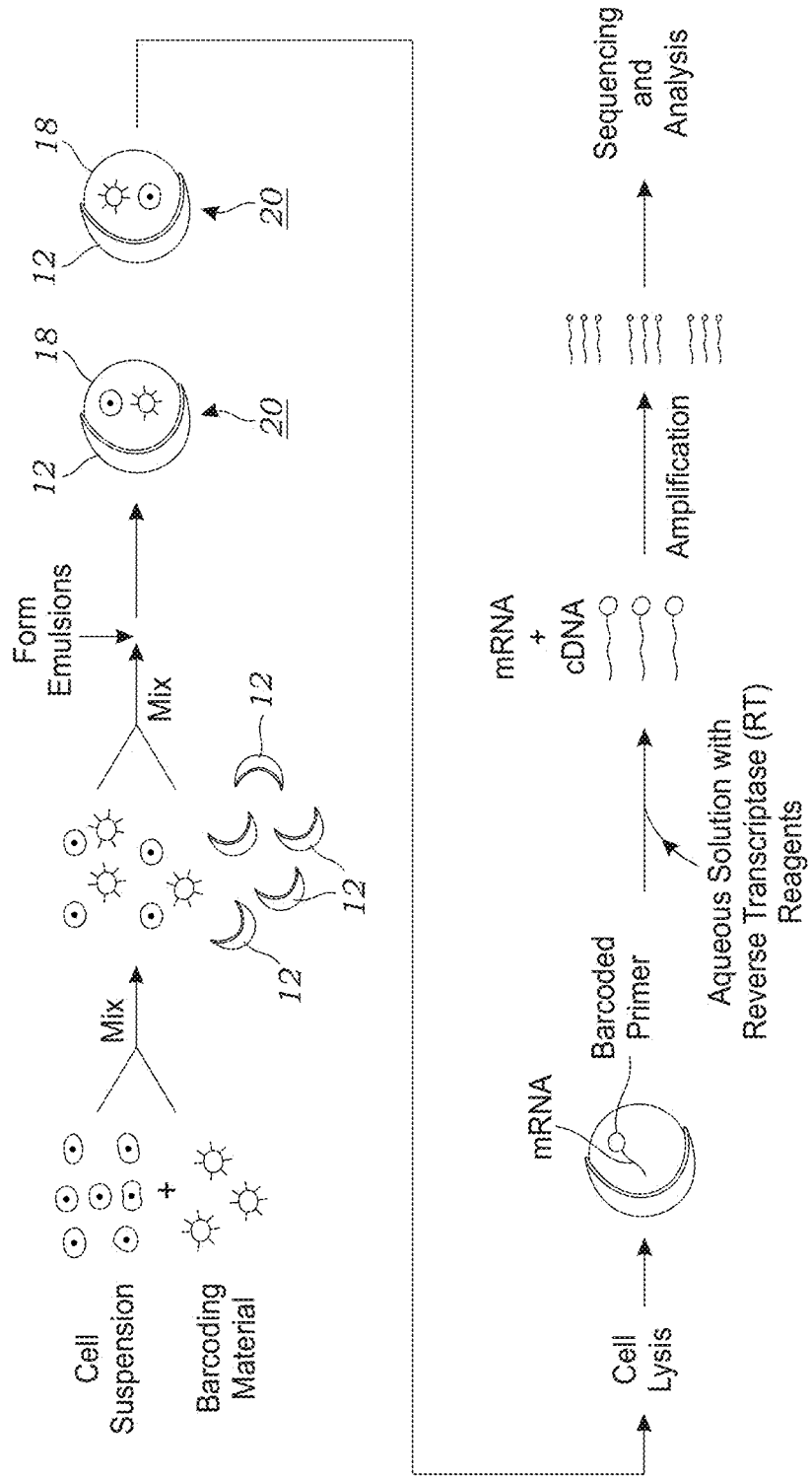
FIG. 15 illustrates a first protocol or method used to achieve single-cell RNA-sequencing using the particle-drop system described herein.

FIG. 15 illustrates a first protocol or method used to achieve single-cell RNA-sequencing using the particle-drop system described herein. The method uses the following operations: (1) prepare a single-cell suspension solution with a known cellular concentration; (2) mix the single-cell suspension solution and a solution of separate microspheres or microbeads with barcoded primers (or hydrogel microparticles with photocleavable barcoded primers) (i.e., a barcoding material); (3) add a dried drop-carrier particle 12 powder into the mixed solution and vortex it completely; (4) pour the mixed solution with particles into carrier oil (e.g., fluorinated fluid), or add oil into the mixed solution; (5) apply gravitational, centrifugal, or magnetic force to transport drop-carrier particles 12 from the mixed solution to the carrier oil to isolate a fraction of particle-drops 20 carrying a single cell and a barcoded microsphere/microbead (or hydrogel microparticle) inside each of the fluid droplets 18 of the drop-carrier particles 12; (6) lyse the single cell in each droplet 18 physically, e.g., temperature increase, sonication and freeze-thaw, or chemically, e.g., adding lysis-buffer droplet suspensions (or another set of lysis-buffer-drop-carrier particles 12 with particle shape complimentary to the particles for cell suspension) in the carrier oil; (7) capture mRNAs of the single cell on its companion microsphere (or the primer photocleaved from the hydrogel microparticle after lysis); (8) transfer the drop-carrier particles 12 from the carrier oil back to an aqueous solution by adding large amount of the solution with reverse transcription (RT) reagents, which allows simultaneous production of cDNA with barcoded nucleic acid sequences; (9) conduct PCR (or other reduced biased amplification procedure to amplify all cDNA) and perform sequencing. The cDNA are sequenced and sourced back to the cell of origins by the barcode of the primer.

Figure 16:
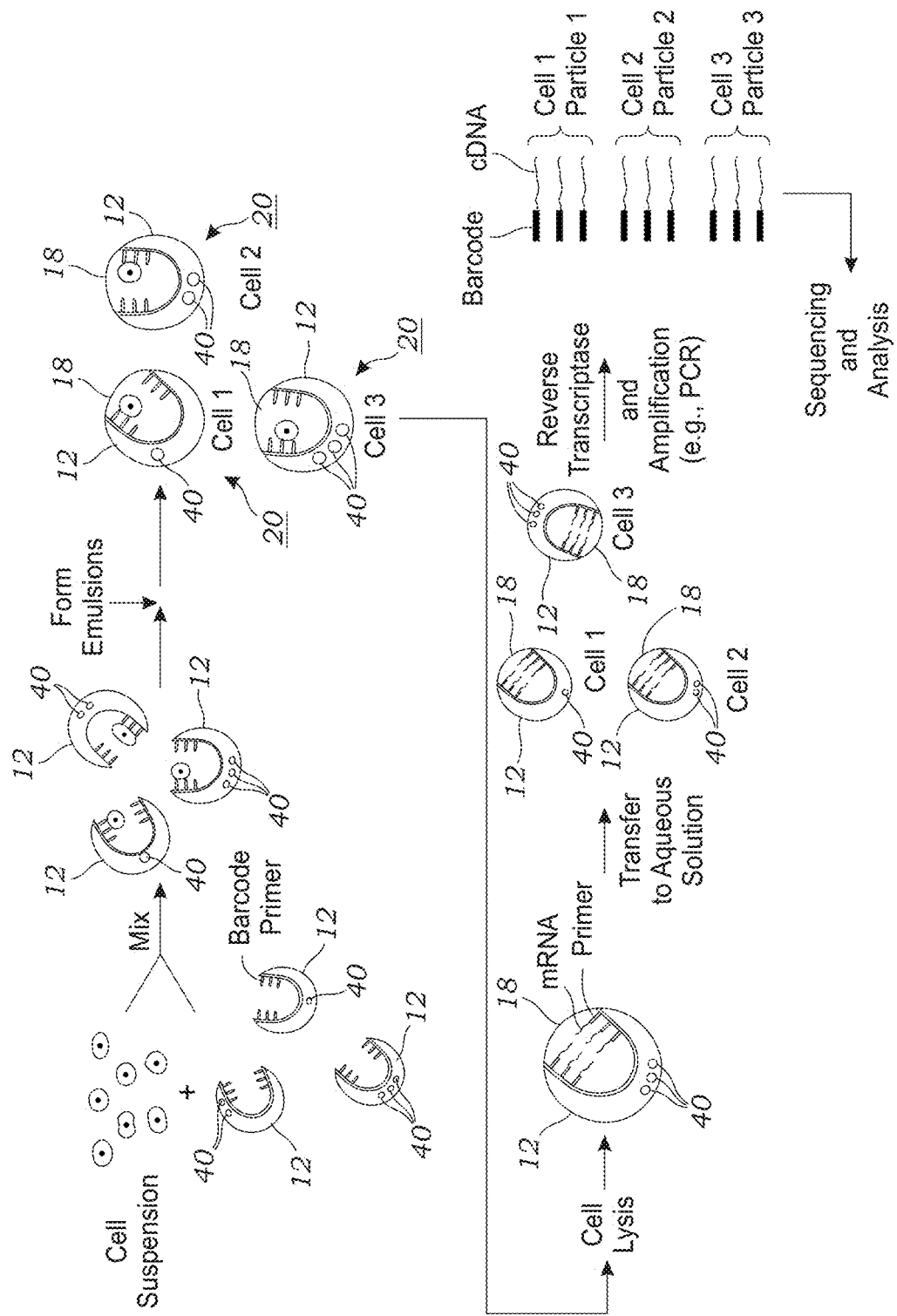
FIG. 16 illustrates a second protocol or method used to achieve single-cell RNA-sequencing using the particle-drop system described herein.

FIG. 16 illustrates a second protocol or method used to achieve single-cell RNA-sequencing using the particle-drop system described herein. The method uses the following operations: (1) prepare a single-cell suspension solution with a known cellular concentration; (2) add a quantity of dried powder of drop-carrier particles 12 that optionally have particle identifying indicia 40 or shapes with linked barcoded primers into the solution and vortex it completely (the volume supported by the drop-carrier particles should be matched to the volume of the solution); (4) pour the mixed solution into carrier oil or oil into the mixed solution;

(5) apply mixing, centrifugal or magnetic force to aid in transporting drop-carrier particles 12 from the aqueous solution into the carrier oil and isolate particle-drops 20 carrying zero or one cell in each; (6) lyse the single cells in each droplet 18 physically or chemically (e.g., as described above using monodisperse lysis buffer droplets or particle-drops 20 containing lysis buffer in the fluid droplet 18); (7) hybridize single-cell released mRNAs to the primers on the interior surface of each drop-carrier particle; (8) transfer particle-drops 20 back to an aqueous solution with reverse transcriptase and perform reverse transcription to create barcoded cDNA; use template switching to link synthesized cDNA with a PCR handle; (9) utilize the cDNA product for PCR or other non-biased amplification and then sequencing. The mRNA transcripts are sequenced and sourced back to the cell of origins by the barcode of the primer.

There are a number of applications for particle-drops 20 with unique benefits because a set of solid-phases is associated with fluid drops 18 of substantially uniform volume. Many of these applications are enabled by isolating single entities (e.g., single-molecules or single-cells). Single-cell secretion analysis is an area that significantly benefits from an associated solid-phase to capture secreted molecules from cells within the aqueous phase internal to the particle-drop 20 but prevent cross-talk between neighboring cells in neighboring particle-drops 20. For example, a secretion capture moiety may be present on the drop-carrier particle 12 with affinity which depends on the application. A secondary reporter molecule (e.g., antibody, aptamer, or enzyme) may also be present that binds to the secreted molecule at a different site. The secondary reporter molecule may have an attached fluorophore such that the accumulation of the secreted molecule and accumulation of the secondary reporter molecule leads to a local increase in fluorescence signal intensity which can be observed and quantified.

Particle-drops 20 can be used to enable the sorting and measurement based on secreted molecules. A drop-carrier particle 12 can be fabricated to include one or more molecular capture regions on the interior hydrophilic region 14 of the drop-carrier particle 12. For example, a biotinylated polyethylene glycol precursor can be used to create a biotinylated region on the drop-carrier particle 12, bind streptavidin and then a biotinylated antibody. An exemplary application is in detecting cytokine secretions by leukocytes. In this case, the antibody would have affinity to the cytokine of interest. Multiple capture antibodies can also be used to cover the capture surface and have affinity for a variety of cytokines (e.g., IL-2, IL-7, IL-9, TNF-alpha, IFN-gamma). In this case, the binding of secreted molecules is distinguished by the fluorophore spectrum and intensity of the reporter molecules. The limitation of number of different secreted products that can be detected is based on spectral overlap between the reporter fluorophores (which limits to ~5 separate fluorophores in the visible range). One can also create a plurality of molecular capture regions with spatial heterogeneity in location in the hydrophilic interior region 14 of the drop-carrier particle 12 to expand the number of secreted molecules that can be sensed. In this case biotin alone cannot be used and maintain selectivity and polymer precursor streams containing oligonucleotide capture regions with unique sequences can be used for each distinct capture location. The complementary oligonucleotide for each capture location can then be conjugated to antibodies or other capture agents to link them specifically to the desired spatial locations. In some embodiments the interior hydrophilic region 14 also contains a region with capture antibodies specific to cell-surface proteins (e.g., EpCAM, CD4, CD3, or CD8), enabling selective enrichment of cells with high level of expression of specific cell-surface proteins (e.g., epithelial cells, or CD4 T Cells) within the particle-drops 12.

The process of measuring or sorting cells based on secretions using particle-drops 20 begins with creating an emulsion supported by the drop-carrier particles 12 with cells. Drop-carrier particles 12 are mixed with an aqueous solution of suspended and thoroughly washed cells, and added to a hydrophobic continuous phase and mixed as described to create the particle-drop 20 emulsion. Thorough washing is necessary to remove background secreted molecules. Reporter antibodies conjugated to fluorophores can be added to this washed cell solution, or can be added through a solution exchange operation as described herein. A suspension of particle-drops 12 containing single-cells in the fluid droplet 18 that is carried therein is then incubated at about 37° C. for 30 min to 2 hours to accumulate the secretions of cells and allow binding to the functionalized particle-drop 20 surfaces. The reporter molecule then binds to the secretions localized to the particle-drop 20 surface creating a localized fluorescent signal. This localized fluorescent signal and the presence of the cell (through nuclear intercalating dyes, cell-surface stains or viability dyes) can be analyzed by imaging approaches in the suspended state. For example, automated microscopy can be used to identify particle-drops 20 containing single-cells with profiles of secretion that are desired based on the intensity and/or wavelength levels of fluorescent signals corresponding to secreted molecules. An analysis can be performed based on the distribution of single-cells with different classes of secretion profiles to create a diagnostic readout, for example in autoimmune disorders, sepsis, or transplant rejection. Besides use in diagnostics, cells with specific secretion profiles (e.g., antibody secretion with high titer and high affinity to antigen) can be selected using this approach for evolving high-secreting clones for antibody production for example.

Drop-particles 20 are also an excellent platform to capture the diversity of nucleic acids in a sample using an approach similar to beads, emulsions, amplification and magnetics (BEAMing). In this approach a pre-amplification step is performed on a sample to generate tag nucleic acid regions on a diverse set of amplified nucleic acids. These nucleic acids are captured onto the interior region 14 of the drop-carrier particles 12 based on hybridization to the tag region which is linked to the drop-carrier particle 12. Linking of the tag region can be achieved using biotin-streptavidin linkages after covalently linking biotin into the interior hydrophilic region 14 of the drop-carrier particle 12. Particle-drops 20 containing the nucleic acids are generated by adding an external oil phase. Unlike with BEAMing, using particle-drops 20 limits the number of solid phase particles per fluid compartment and amplification reaction. In addition, each fluid droplet 18 has a more uniform volume and amount of reagents in the particle-drop approach. Combined, this yields better quantitative accuracy in the abundance of particular nucleic acids within a sample, instead of over counting based on multiple beads being encapsulated into a single droplet. Amplification is then performed within the drop-carrier particle 12 to amplify the signal from the enclosed nucleic acids within a particular particle-drop 20 that are immobilized on the drop-carrier particle 12. Following amplification and immobilization, the emulsion is broken to bring the drop-carrier particles 12 back into aqueous solution. These drop-carrier particles 12 can be reacted to hybridize with various nucleic acid sequence-specific probes with attached fluorophores and read and sorted using flow cytometry or fluorescence-activated cell sorting.

A modification of the BEAMing protocol achieves a digital PCR-based solution using particle-drop technology. For digital PCR the pre-amplification step is not necessary and an overhanging tag region is introduced into primers that are specific to a particular target sequence. This tag sequence is also attached to the hydrophilic interior surface 14 of the drop-carrier particle 12. For particle-drops 20 that contain the single nucleic acid sequence that is amplified, copies of the sequence are covalently linked to the drop-carrier particle 12 by incorporation of the immobilized tag sequence on the surface of the drop-carrier particle 12. Following amplification and breaking the emulsion, specifically amplified and linked nucleic acids can be labeled with intercalating dyes or sequence specific probes and then analyzed by flow cytometry. A one-pot multiplexed digital nucleic acid amplification reaction and analysis can be performed using this approach. In this case no pre-amplification is performed and drop-carrier particles 12 are encoded to have primer tag sequences which are immobilized and have a universal region and specific region unique to target nucleic acid sequences. Amplification is performed in the particle-drop 20 which leads to amplification and attachment of nucleic acid sequences to the surface of the drop-carrier particle 12 in cases where one or more target nucleic acids was initially present. Once nucleic acids are attached, drop-carrier particles 12 can be transferred into an aqueous suspension where target specific probes are added or intercalator dyes are added to generate sequence-specific or double stranded DNA-specific fluorescent signal for amplified drops. Drop-carrier particles 12 can then be analyzed on a flow cytometer and the number of positive particles with intensity above a threshold can be counted in order to generate a measure of concentration of a specific nucleic acid. The system can be multiplexed using separate fluorophores conjugated to probes targeted different target nucleic acid sequences, or mixtures of two or more probes targeting a sequence with different ratios for each different target sequence to give even further increases in multiplexing capability. This assay can also be multiplexed at the level of different drop-carrier particles 12 mixed together that use separate fluorescent colors of the barcoded drop-carrier particles 12 or scatter signatures induced by different shape of drop-carrier particles 12 to distinguish different assays.

For this application, drop-carrier particles 12 with embedded magnetic particles 36 can be used in order to enable easy separation and washing or drop-carrier particles 12 can be non-magnetic and transfer steps can be performed by centrifugation.

In a similar process to digital PCR and BEAMing, reduced bias whole genome amplification can be achieved by using particle-drops 20. Whole genome amplification using approaches like multiple displacement amplification (MDA) can lead to bias since during exponential amplification small differences in kinetics can lead to several fold changes in amplification efficiency of different regions of DNA. This can lead to less reads in particular genes and reduced accuracy. Amplification of cDNA from a transcriptome can also benefit from reduced bias whole transcriptome amplification. First the fragmented DNA in an aqueous solution is mixed with drop-carrier particles 12, following mixing, oil is added and mixing further disperses and forms uniform sized particle-drops 20. Using the small particle-drop 20 compartments and amplification of only a single gene fragment in each compartment surrounded by an oil external phase allows for uniform amplification that can be run to completion in each compartment (i.e., fluid droplet 18). Because the reaction amount depends on compartment volume, particle-drops 20 are advantageous because they create uniform sized compartments. Following amplification, the particle-drops 20 can be brought back into an aqueous solution and the amplified regions are retrieved into a bulk solution for further downstream sequencing or other analysis.

Particle-drops 20 can also provide a uniform emulsion for new techniques like DropSynth such as that described in C. Plesa et al., Science 10.1126/science.aao5167 (2018), which is incorporated therein by reference. In the DropSynth technique large genes, which would be difficult to synthesize using current techniques, are assembled in a massively parallel process by first having barcoded beads with tag nucleic acid sequences that will hybridize to the many oligonucleotide pieces that make up the larger gene. The beads are then prepared into an emulsion, the oligonucleotide pieces are digested to be cleaved from the beads and released into the droplet, and then assembled using enzymatic ligation. The interior solid phase of a drop-particle 20 can act to both template the initial oligonucleotide collection that will be incorporated in the reaction as well as create the emulsion with uniform droplet 18 size which allows for more uniform downstream reactions for gene assembly in the droplet 18. The emulsion can then be broken to collect the synthesized genes or sorted based on barcoding of the drop-carrier particles 12.

Besides digital nucleic acid amplification tests, digital immunoassays can be uniquely enabled by particle-drop technology. Digital versions of the enzyme-linked immunosorbent assay traditionally require a solid phase bead that has a capture antibody for a target biomolecule of interest (e.g., antigen), following capture of zero or one molecules per bead, remaining sample solution is washed away and a secondary antibody solution is introduced and secondary antibodies (polyclonal or monoclonal to a different site) bind to form a sandwich with the captured target. The secondary antibody or other recognition element is conjugated to an enzyme like HRP to generate amplified signal from fluorescent reporters. In the digital assay, the bead is confined in a fluid compartment (e.g., well or drop) so that fluorescent signal is contained within the small volume drop and is amplified to a high concentration from the initial single molecule. Challenges with the traditional digital assays include maintaining only a single bead per compartment and complex readout instruments that are limited to a certain field for microwell arrays.

Figure 17:
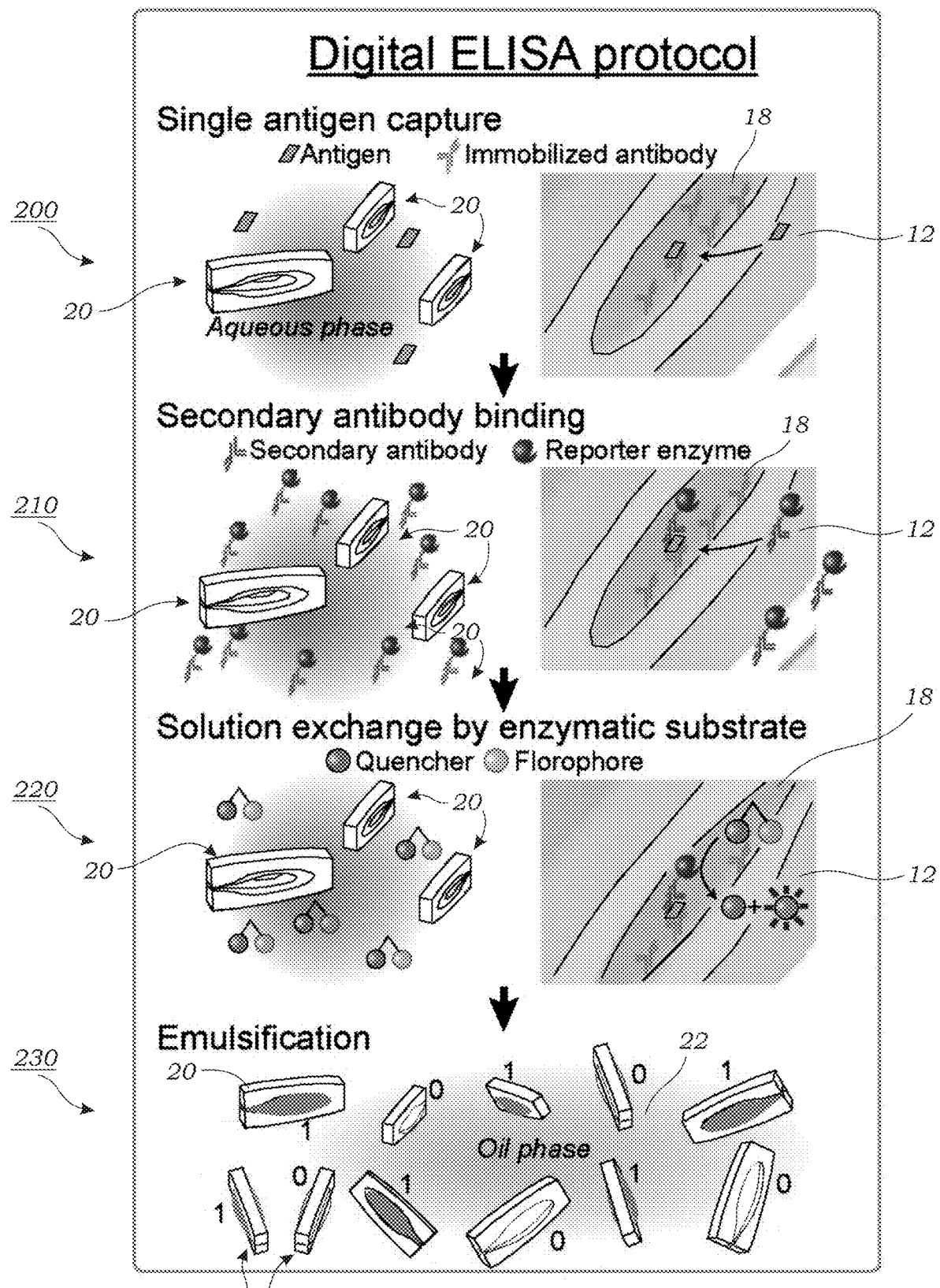
FIG. 17 illustrates a sequence of operations used to perform a digital enzyme-linked immunosorbent assay (ELISA) according to one embodiment.

Particle-drops 20 can provide significant advantages for digital ELISA assays. FIG. 17 illustrates a sequence of operations used to perform a digital ELISA assay. Implementing digital ELISA in particle-drops 20 first requires immobilizing capture antibodies on the interior hydrophilic region 14 of the drop-carrier particles 12. This is accomplished as described herein using biotin-avidin binding interactions to biotinylated PEG hydrogel as the interior region 14 of the drop-carrier particles 12, for example. Drop-carrier particles 12 with attached antibody are mixed with an aqueous solution of sample (containing an antigen) and allowed to bind with gentle mixing for 10-15 minutes. FIG. 17 illustrates in operation 200 an antigen-containing aqueous sample solution that is exposed to the drop-carrier particles 12 with attached antibody.

The sample is then centrifuged or magnetic drop-carrier particles 12 are collected to the bottom of a tube and washed a plurality of times (e.g., three times) to remove unbound sample. Then secondary antibody solution which contains the secondary antibody and a reporting enzyme is introduced as seen in operation 210 of FIG. 17 and washed 3-5 times to remove the unbound secondary antibody. Next, as seen in operation 220 of FIG. 17 the substrate of the enzyme linked to the secondary antibody is introduced. This may include, for example, a fluorogenic substrate or quencher/fluorophore pair. In operation 230 of FIG. 17, the sample is then emulsified by mixing with an oil phase. Signal then accumulates in the particle-drops 20 which can be read for fluorescence intensity using microscopy of other fluorescence imaging technique to count the number of particle-drops 20 with intensity above a threshold that were considered positive which yields the target's concentration in the sample. FIG. 17 illustrates the resulting particle-drops 20 being labelled as negative ("0") or positive ("1"). In the case that the reaction is desired to be read out in a flow cytometer the particle-drops 20 need to be first transferred back to an aqueous solution. This transfer would lead to loss of accumulated fluorescent signal as the oil phase no longer maintains a barrier. In order to capture the amplified signal on the drop-carrier particle 12 tyramide signal amplification or catalyzed reporter deposition (CARD) techniques can be used. For example, tyramide biotin (or tyramide Alexa Fluor® 488) can be covalently linked to neighboring tyrosine residues within peptides or proteins attached to the interior hydrophilic hydrogel matrix of the drop-carrier particle 12. This covalent linkage is catalyzed by the presence of horse radish peroxidase attached to the secondary antibody. Following reaction and high efficiency linkage to the drop-carrier particle 12 while emulsified to localize signal, these drop-carrier particles 12 can be transferred to an aqueous phase for readout by flow cytometry for example, or reacted with streptavidin-conjugated to fluorophore and then run through a flow cytometer. The amount of particles with signal above threshold can be counted by gating on the flow cytometer to determine the concentration in the sample. Multiplexing can be conducted of multiple biomolecules by simultaneously mixing particles with different barcoding schemes as discussed herein that include separate capture antibodies targeting the set of biomolecules of interest. This multiplexed assay can use fluorescent colors of the barcoded drop-carrier particles 12 or scatter signatures to distinguish different assays. These other drop-carrier particles 12 with off-target antibodies can also serve as negative controls within a run.

The particle-drops 20 also provide advantages for single-cell RNA sequencing workflows. Current workflows encapsulate cells in droplets, merge these droplets with other droplets that contain spherical beads with mRNA capture moieties (e.g., an oligonucleotide containing a poly T region, a unique molecular identifier tag (UMI), and a uniform bead-specific tag) and cell lysis buffer. Following lysis, mRNA from a single cell is released and captured on the bead encapsulated in the same droplet. Once mRNA is captured, the emulsion is broken and the beads are washed and exchanged into solution with reverse transcriptase in order to generate cDNA that contains the captured sequence information, the UMI, and the bead-specific barcode sequence. This type of Drop-Seq barcoding technique is described, for example, in Macosko et al., Highly Parallel Genome-wide Expression Profiling of Individual Cells Using Nanoliter Droplets, Cell, 161, 1202-1214 (2015), which is incorporated herein by reference (including all Supplemental Information).

This cDNA can be further amplified and run through standard next-generation sequencing instruments (such as from Illumina, Inc.). Using drop-carrier particles 12 a single-cell and "bead" (e.g., the drop-carrier particle 12 in this embodiment) are automatically brought together without the challenges of Poisson loading of droplets with beads. Cells can also be specifically captured on the drop-carrier particle 12 based on surface antigens targeting a particular cell type while in an aqueous phase prior to suspension in a surrounding oil phase. This also improves the cell loading in the particle-drops 20 beyond the current limitations of Poisson statistics which leads to large numbers of empty drops and waste of reagents in the current Drop-Seq single-cell protocols such as that described in Macosko et al. Cell lysis can be performed by transferring a lysis solution into the particle-drop 20 following the initial formation of particle-drops 20.

When no surfactant is used when mixing drop-carrier particles 12, aqueous cell solution, and oil together particle-drops 20 form. For particle-drops 20 without surfactant coating of their free surfaces, the addition of new solution can lead to exchange of this solution into the particle-drop 20 without disrupting the particle-drop size. For example, one protocol for single-cell RNA-seq using drop-carrier particles in which the interior hydrophilic region contains barcoded capture oligonucleotides and cell capture antibodies includes the following steps. First, dehydrated drop-carrier particles 12 are mixed with cells in an aqueous solution to capture cells within drop-carrier particles 12. Second, an oil phase is introduced and mixed to form suspended particle-drops 20 containing adhered cells within the fluid droplet 18. Third, a lysis solution is introduced and rapidly mixing to enable entry into the particle-drops 20. Fourth, the mixture is allowed to incubate in a quiescent state to allow cell lysis and capture of mRNA onto the interior surface of the drop-carrier particles 12. Fifth, the drop-carrier particles 12 are brought back into an aqueous solution for downstream cDNA generation and sequencing. An example formulation for Cell lysis buffer that can be used is described by Macosko et al. (Drop-Seq Lysis Buffer-DLB, 200 mM Tris pH 7.5, 6% Ficoll PM-400, 0.2% Sarkosyl, 20 mM EDTA). In a similar manner to single-cell RNA analysis, protein-based barcoding for downstream single-cell analysis using sequencing can be achieved by including capture antibodies for proteins on the surface of the hydrophilic interior region 14 of the drop-carrier particles 12. A secondary antibody sandwich can then include oligonucleotide barcodes that can be read and associated with a specific cell when pooled using nucleic acid sequencing as a final step. Such an approach for converting protein signal to nucleic acid signal is disclosed in Peterson et al., Multiplexed quantification of proteins and transcripts in single cells, Nature Biotechnology, Vol. 35, No. 10, (2017), which is incorporated by reference herein.

There are two main readout approaches for the products of particles-drops 20. Optical readout of a fluorescent signal is a first approach that can be conducted using fluorescence microscopy, wide-field computational microscopy, flow cytometry, or imaging flow cytometry. Optical microscopy can be performed both while particle-drops 20 are surrounded in an oil phase or following transfer into an aqueous phase, especially if the generated signal is attached to the surface of the drop-carrier particle 12. When transferring to an aqueous solution adhesion between particles along hydrophobic exterior surfaces can be mitigated to enable improved readout by addition of an optional surfactant that interacts with the hydrophobic exterior phase of the drop-carrier particle 12 (e.g. Pluronic®, Pico-Surf™ etc.), and allows for lower interfacial energy with the new surrounding aqueous phase. In other embodiments, the readout of single-cell RNA seq, single-cell DNA sequencing, or bias-free whole genome application includes further nucleic acid amplification and gene sequencing using standard commercial instruments such as those sold by Illumina, Inc.

In flow cytometry-based readout, particle-drops 20 are first transferred back to an aqueous phase. Fluorophores yielding a fluorescent signal are maintained attached to the drop-carrier particle 12 following transfer to an aqueous external phase due to affinity with a capture reagent on the interior region 14 of the drop-carrier particle 12. In some embodiments, cells are also adhered or captured in the drop-carrier particle 12 where they can be stained in an aqueous phase with nuclear dyes or antibody-conjugated dyes to specific proteins and analyzed by flow cytometry. Once in an aqueous phase, suspensions of drop-carrier particles 12 (with molecular and/or cellular attached signals) are introduced into the flow cytometer for particles to be analyzed by forward and side scatter signals as well as attached fluorescence signals (from molecular binding events, presence of nucleic acids, or cells present). Drop-carrier particles 12 that are used in flow cytometry analysis should be relatively neutrally buoyant in the suspending medium to avoid drop-carrier particles 12 from settling, and sized to prevent clogging of commercial flow cytometer flow cells (e.g. <70 micrometers in diameter for most flow cytometers from BD or Beckman Coulter, or <500 micrometers in diameter for the Biosorter from Union Biometrica). Drop-carrier particles 12 can also be shaped or sized to elicit unique scattering signals from forward or side scatter. This is advantageous since multiple species of drop-carrier particles 12 that are specific to different target molecules or cells can be mixed together for analyzing a sample and can be distinguished by a scatter-based barcode or signature. For example, drop-carrier particles 12 without sharp edges vs. particles containing more edges will yield different scatter signals, with the number of sharp edges correlating with the amount of scatter signal. Preferably an asymmetric shape of the drop-carrier particle 12 along at least two axes will yield alignment in the squeezing asymmetric sheath flow of a flow cytometer such that the scatter signal is more uniform between drop-carrier particles 12.

Drop-carrier particles 12 with more or less holes, notches, or other surface features will yield unique side-scatter signatures. Drop-carrier particles 12 with 1-6 holes or notches in a 2×3 array yielding six (6) unique scatter signals can provide barcoding for six (6) separate reactions or molecules. The notches can be made in the surrounding hydrophobic external region 16 of the drop-carrier particle 12 or in the interior hydrophilic region 14 of the drop-carrier particle 12. In addition to or instead of a scatter-based barcode, drop-carrier particle 12 may also possess a fluorescence "barcode" that consists of fluorophores or fluorescent particles embedded into or attached to the drop-carrier particle 12. The barcode can include multiple fluorophores or a single fluorophore of multiple well-defined concentrations that when excited elicit well-defined intensities, or a combination of fluorophores and intensities in various permutations to yield a large number of individual barcode signatures (e.g., two (2) fluorophores and five (5) intensities yields twenty-five (25) unique barcodes). Fluorophores used for barcoding of drop-carrier particles 12 will preferably not overlap in emission spectra with fluorophores used in sensing on the drop-carrier particles 12. In addition to analysis, sorting can be performed based on a combination of a barcode signal and molecular or cellular signal. Unique populations of barcoded drop-carrier particle 12 can be gated for sorting using standard gating tools in fluorescence activated cell sorters. In addition, unique populations of drop-carrier particle 12 with attached cell populations can be gated and sorted based on fluorescence signal intensity or combinations of fluorescence signals.

Drop-carrier particles 12 in an aqueous solution can also be read using commercial imaging flow cytometers (e.g., for these instruments, drop-carrier particle 12 size should be preferably between 5 micrometers and 70 micrometers in size). The imaging flow cytometer can characterize fluorescence intensity of the drop-carrier particle 12 associated with the signal from a target molecule or cell attached to the drop-carrier particle 12, image an attached cell, or image a shape barcode of the drop-carrier particle 12 itself. The shape barcode can include changes in the overall morphology of the drop-carrier particle 12 envelope if extruded in 2D through the particle, or may include embedded notches, holes, or surface features that are included on a surface of the drop-carrier particle 12 in a 2D or linear array. The unique shape barcode can be associated with a unique molecular targeting agent on the surface of the drop-carrier particle 12 that would otherwise not be visible, and therefore allow distinguishing between different classes of drop-carrier particles 12 specific to different biomarkers. This would enable extreme multiplexing for detection of up to thousands of protein biomarkers for example.

In one embodiment, drop-particles 20 do not contain a cavity or void 24 for an internal aqueous phase, but instead contain a hydrogel matrix that an aqueous solution can swell internal to an exterior region of the particle that remains hydrophobic. An example of this embodiment is illustrated in FIG. 5. The mesh size and pore structure of this hydrogel matrix is important to control to enable molecular binding and enzymatic reactions within the material. For example, Xu et al. show that nucleic acid amplification reactions can be performed within PEG hydrogel gels. Xu et al., Virtual microfluidics for digital quantification and single-cell sequencing, Nature Methods, Vol. 13, No. 9, pp. 759-764 (2016), which is incorporated by reference. For example, the mesh size of PEG-based hydrogels formed using four-arm PEG crosslinkers is about 25 nm at 10% (w/v), which allows diffusion of small molecules, oligonucleotides and enzymes but immobilizes cells and high-molecular-weight nucleic acids. Therefore, digital nucleic acid amplification reactions may be performed in the hydrogel matrix of the particle-drop 20 once encapsulated in an external oil phase. In addition, this pore size is sufficiently large for antigen-antibody or antigen-aptamer binding reactions within the hydrogel matrix, as well as secondary antibody binding and signal generation from enzymes such as horse radish peroxidase or beta-galactosidase conjugated to secondary recognition elements (e.g., antibodies or aptamers).

In an alternative embodiment, the PEG gels can be functionalized to allow immobilization of low-molecular-weight species by attachment to the gel matrix. For example, acrydite modification on 5' end of one of the primers in a polymerase chain reaction can be used to covalently link the amplified DNA to the hydrogel matrix. See e.g., Mitra et al., In Situ localized amplification and contact replication of many individual DNA molecules, Nucleic Acids Research, Vol. 27, No. 24 (1999), which is incorporated by reference herein. Alternatively, the primers can be linked to the hydrogel matrix using biotinylated primers that bind specifically to streptavidin immobilized within the hydrogel matrix. The amplified DNA linked to the matrix can then be assayed using intercalating dyes within the solution surrounded by an oil phase or once transferred to an aqueous phase. Other readout approaches that are sequence specific can also be incorporated, such as by hybridizing complementary fluorophore labeled nucleic acid probes to the immobilized and amplified nucleic acids. In other nucleic acid amplification reactions, e.g. loop-mediated isothermal amplification (LAMP) or rolling circle amplification, the nucleic acids produced are much longer and can be physically entrapped in the hydrogel matrix without the ability to leave, however, still allow exchange of other reagents and dyes (e.g., intercalator dyes such as EvaGreen® or SYBR® Green, or molecular beacons or other fluorophore labeled complementary sequences) upon transferring back to an aqueous external phase. Protein targets can be covalently linked to the gel matrix with the addition of a crosslinking agent and upon exposure to a crosslinking reaction. For example, as discussed in the work of Herr et el., which is incorporated herein by reference, N-(3-((4-benzoylphenyl) formamido) propyl) methacrylamide can be used along with photo-activation to covalently link proteins to the hydrogel matrix. See Kang et al., Single cell-resolution western blotting, Nature Protocols, Vol. 11, No. 8, pp. 1508-1530 (2016). A UV light source capable of providing 350-360 nm~1.8 J/cm$^2$ of light can be used to link proteins on particle-drops 20. This process can be performed while particle-drops 20 are in an oil suspension to covalently link protein targets to the interior region 14 of the drop-carrier particle 12. The drop-carrier particles 12 can then be transferred back to an aqueous solution for further immune-labeling of protein biomarkers and analysis in aqueous solution.

An alternative embodiment to entrap molecular or cellular targets within a particle-drop 20 includes polymerizing a pre-polymer solution that acts as the internal aqueous phase 18 of the particle drop 20 following capture of cells, molecules, or other products of amplification reactions within the particle-drop 20. The internal polymerization reaction also covalently links the target molecules or amplification products into the hydrogel or physically entraps cells or larger molecules within the hydrogel. Polymerization and covalent linkage or entrapment can be initiated with exposure to light (UV, white light) with the appropriate photoinitiator (e.g., Irgacure, Eosin Y), exposure to heat, or exposure to a pH change. For example, the LAMP reaction can proceed within 4% 4-arm PEG vinylsulfone, PEG dithiol precursor. Following this polymerization process, the drop-carrier particles 12 can be exchanged into an aqueous solution for downstream reactions, labeling, and flow cytometric or other readout processes.

Figure 18:
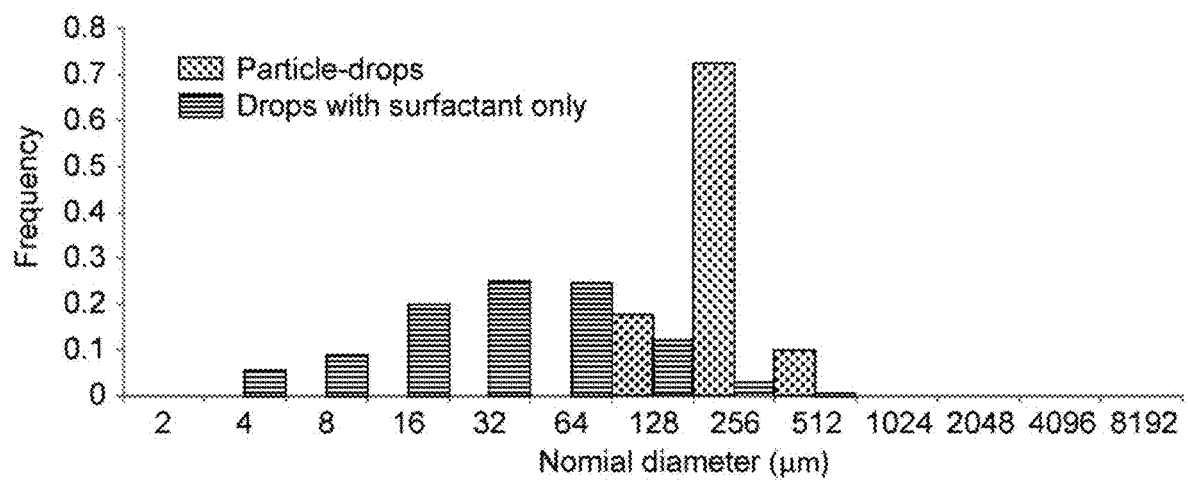
FIG. 18 illustrates a frequency graph of the nominal diameter of the fluid droplets contained in particle-drops and droplets formed with surfactant only.

As explained previously, the drop-carrier particles 12 enable the formation of monodisperse particle-drops 20 without the need of any complex or expensive instruments. FIG. 18 illustrates a graph of the nominal diameter of the fluid droplets 18 contained in particle-drops 20 compared to droplets formed with surfactant only. The latter was generated by following the same protocol except that no drop-carrier particles 12 were suspended in the oil phase and 1% (w/v) surfactant (Pluronic®) was dissolved in the aqueous phase. The size of particle-drops 20 distributes narrowly in the range of 256 microns nominal diameter while the size of the droplets in the surfactant case spans widely. The particle-drops 20 thus can be used as small volume bioreactors having nearly identical volumes.

Figure 19:
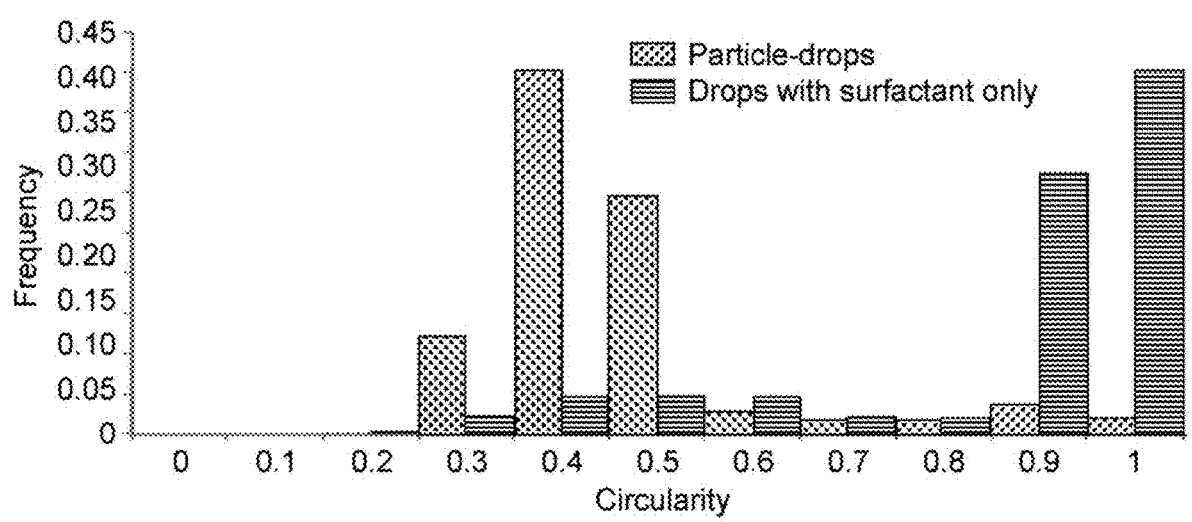
FIG. 19 illustrates a frequency graph of the circularity of the fluid droplets for particle-drops and drops with surfactant only.

FIG. 19 also illustrates the ability of particle-drops 20 to create fluid droplets 18 with non-circular cross-sections. FIG. 19 illustrates the circularity of the fluid droplets 18 for particle-drops 20 and drops with surfactant only. As seen in FIG. 19, a significant departure from circularity is seen for the particle-drops with the circularity concentrated around 0.4. This is in contrast with drops formed with surfactant only which show a circularity of around unity. This shows the ability of the particle-drops 20 to generate non-circular fluid droplets 18.

In some embodiments, molecules or other species may be able to transport between fluid droplets 18 contained in different particle-drops 20. This transport of molecules or other species takes place without the breaking or merging of the fluid droplets 18 of the particle-drops 20. For example, molecules or species may diffuse out of the fluid droplets 18 and be transported inside another fluid droplet 18 contained in a different particle-drop 20. This may take place without the presence of any surfactant. Indeed, the presence of a surfactant may inhibit the transport of molecules or species between different particle-drops 20.

Figure 20A:
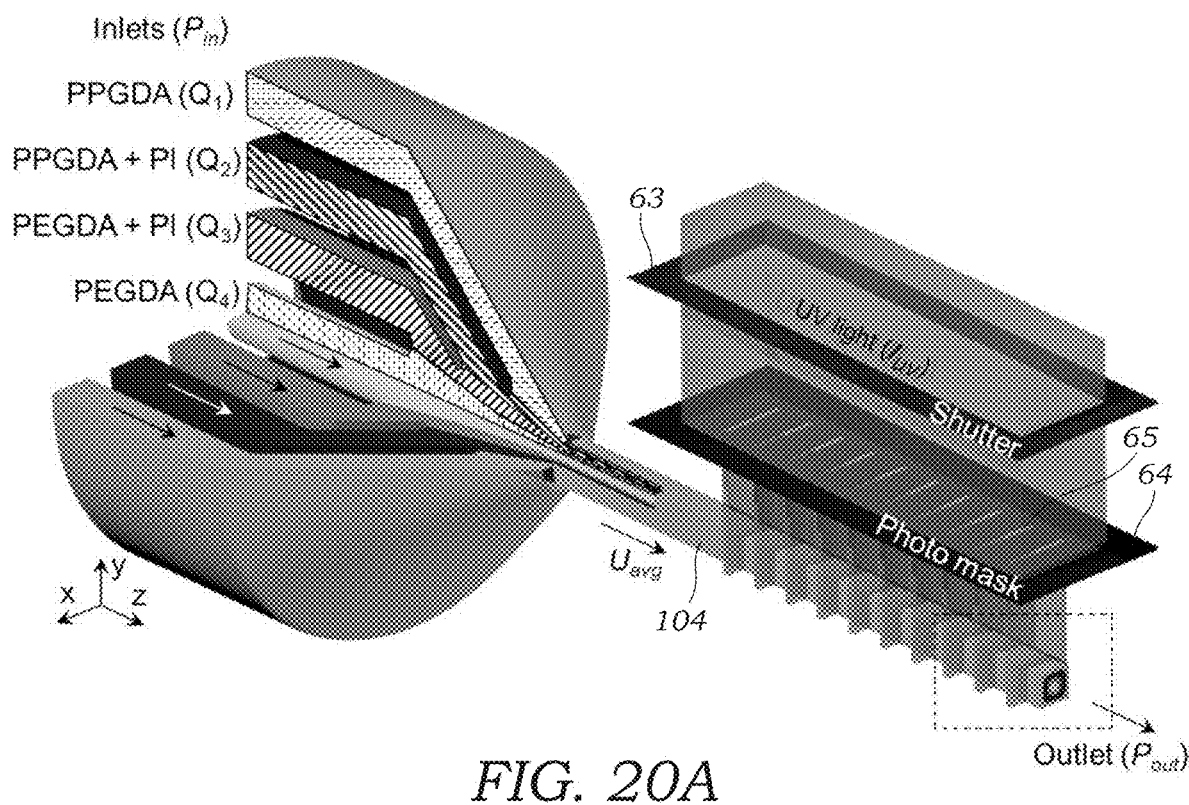
FIG. 20A illustrates another embodiment of a method of manufacturing drop-carrier particles. In this embodiment, multiple streams of density matched fluids (some of which are crosslinkable after exposure to light) are passed through a microfluidic device having non-coplanar channels formed therein by additive manufacturing techniques (e.g., three-dimensional printing). The various channels can be designed with varying co-axial flow cross-sections to yield different shaped final co-flowing streams (e.g., annular) and once photo-crosslinked, final polymerized drop-carrier particles with tuned shapes (e.g. concentric ring-shaped).

FIG. 20A illustrates another embodiment of a method of manufacturing drop-carrier particles 12. In this embodiment, multiple streams of density matched fluids (some of which are crosslinkable after exposure to light) are passed through a microfluidic device 100 such as that illustrated in FIG. 13C having non-coplanar microfluidic channels 104 formed therein by additive manufacturing techniques (e.g., three-dimensional printing). The various microfluidic channels 104 (e.g., four channels 104 in this embodiment) can be designed with varying co-axial flow configurations 106 which yield different shaped (e.g., ring-shaped) drop-carrier particles 12. FIG. 20A illustrates an embodiment with four (4) different streams of density matched fluids, poly(propylene glycol) diacrylate (PPGDA), PPGDA and photo-initiator (PI), poly(ethylene glycol) diacrylate (PEGDA) and PI, and PEGDA are pumped through inlets 1-4 at flow rates $Q_1$ to $Q_4$, respectively, by maintaining a constant inlet pressure of $P_{in}$. The densities of the PPGDA (1.01 g/cm³) and PEGDA (1.12 g/cm³) solutions are matched (0.987 g/cm³) by adding 10% and 40% volume (v/v) ethanol (0.789 g/cm³) in the mixtures, respectively. The PI in this embodiment is 2-hydroxy-2-methylpropiophenone, Darocur 1173, 405655, Sigma-Aldrich (5% by volume).

The PI concentration for channels 2 and 3 is maintained at 5% of the total volume of the PPGDA (90%)+ethanol (10%) and PEGDA (60%)+ethanol (40%) mixtures, respectively. The internal structure of the microfluidic device 100 ensures that the flow stream from channel 4 should meet first with the flow stream from channel 3, which is subsequently followed by combining of flow streams from channel 2 and 1, respectively. Upon exiting the tapered region of the microfluidic device 100, the net flow rate reaches an average velocity of $U_{avg}$ within the downstream square microfluidic channel 104 of the microfluidic device 100 (see FIG. 13C). A pinch valve 60 at the outlet (FIG. 13C) is used to stop the flow entirely ($U_{avg}$=0) by maintaining an outlet pressure of $P_{out}$ (=$P_{in}$) and simultaneously turning the syringe pumps 56 off to cut the flow through the inlets. Therefore, the overall pressure throughout the microfluidic device 100 stays constant. Once the flow has stopped, the shutter 63 is opened after a short delay time ($\tau_d$) to expose the flow streams to UV light source with intensity $I_{UV}$ through a photomask 64 for an even smaller exposure time ($\tau_{exp}$). At this point, the pinch valve 60 is opened ($P_{out}$=0) and the syringe pumps 56 are turned back on to reach an average flow velocity of $U_{avg}$ within a flow stabilization time ($\tau_s$).

Figure 20B:
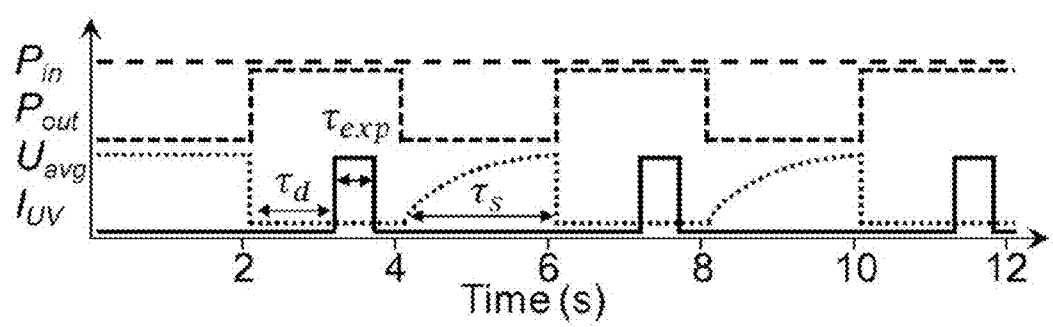
FIG. 20B illustrates an illustrative time sequence of events used to create drop-carrier particles. Illustrated are pressure at the inlet ($P_{in}$), pressure at the outlet ($P_{out}$), average flow velocity through the microfluidic device ($U_{avg}$), and ultraviolet (UV) light Intensity ($I_{UV}$) which is shown as being either on or off. $\tau_d$ refers to delay time, $\tau_{exp}$ refers to exposure time, and $\tau_s$ refers to flow stabilization time.

FIG. 20B illustrates an illustrative time sequence of events used to create drop-carrier particles. Illustrated are pressure at the inlet ($P_{in}$), pressure at the outlet ($P_{out}$), average flow rate through the microfluidic device ($U_{avg}$), and ultraviolet (UV) light Intensity ($I_{UV}$) which is shown as being either on or off. $\tau_d$ refers to delay time, $\tau_{exp}$ refers to exposure time, and $\tau_s$ refers to flow stabilization time.

The plot of FIG. 20B summarizes the whole process of flow stoppage, UV exposure and flow stabilization in a cyclic manner. One fabrication cycle is completed within ~5 s for most experimental conditions. An automated experimental setup integrated through a LabView GUI using well-known software operations allows for rapid and on-demand control of the parameters ($\tau_d$, $\tau_{exp}$, $\tau_s$, and $U_{avg}$) illustrated in the plot. The average flow velocity is controlled by adjusting the flow rate conditions for the four inlets $Q_{1-4}$.

Figure 21A:
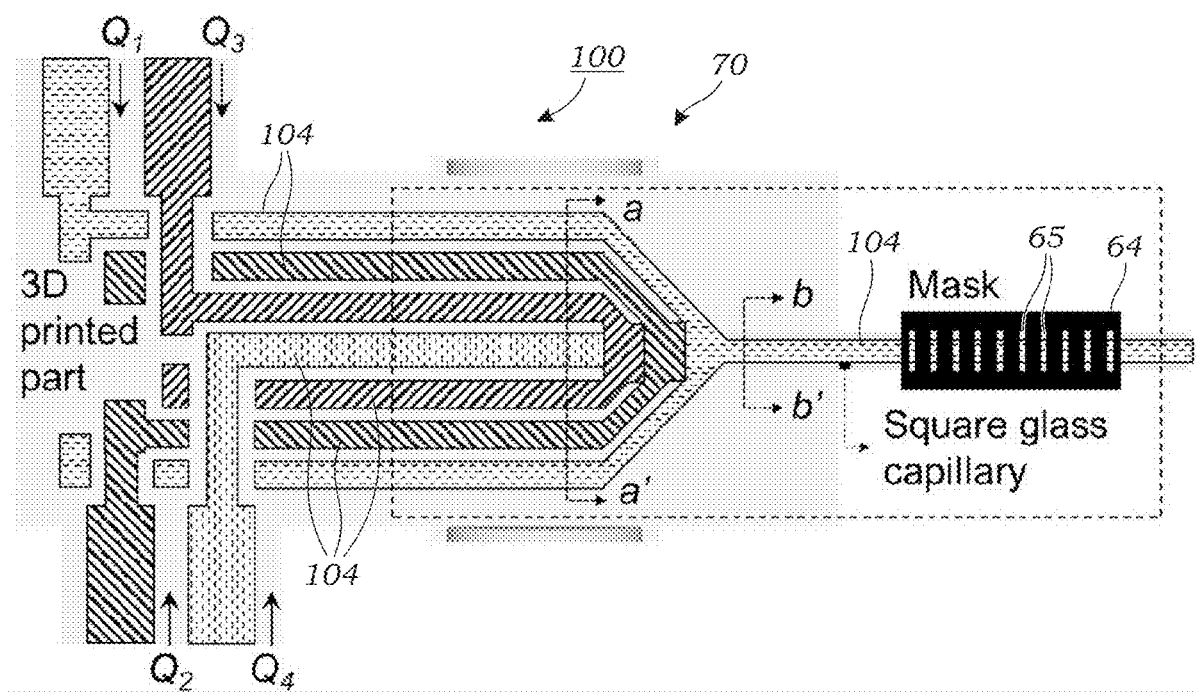
FIG. 21A schematically illustrates one embodiment of a microfluidic device having non-coplanar channels formed therein by additive manufacturing techniques that is used to generate different varying co-axial flow cross-sections which yield different shaped drop-carrier particles. Four (4) separate channels are used to create four different co-axial flows with a square glass capillary attached to the outlet. Note the region of the square glass capillary may be integrated into the microfluidic device. The mask where the flow is illuminated is illustrated above the glass capillary (or microfluidic channel if formed in the microfluidic device).
Figures 21B, 21C, 21D:
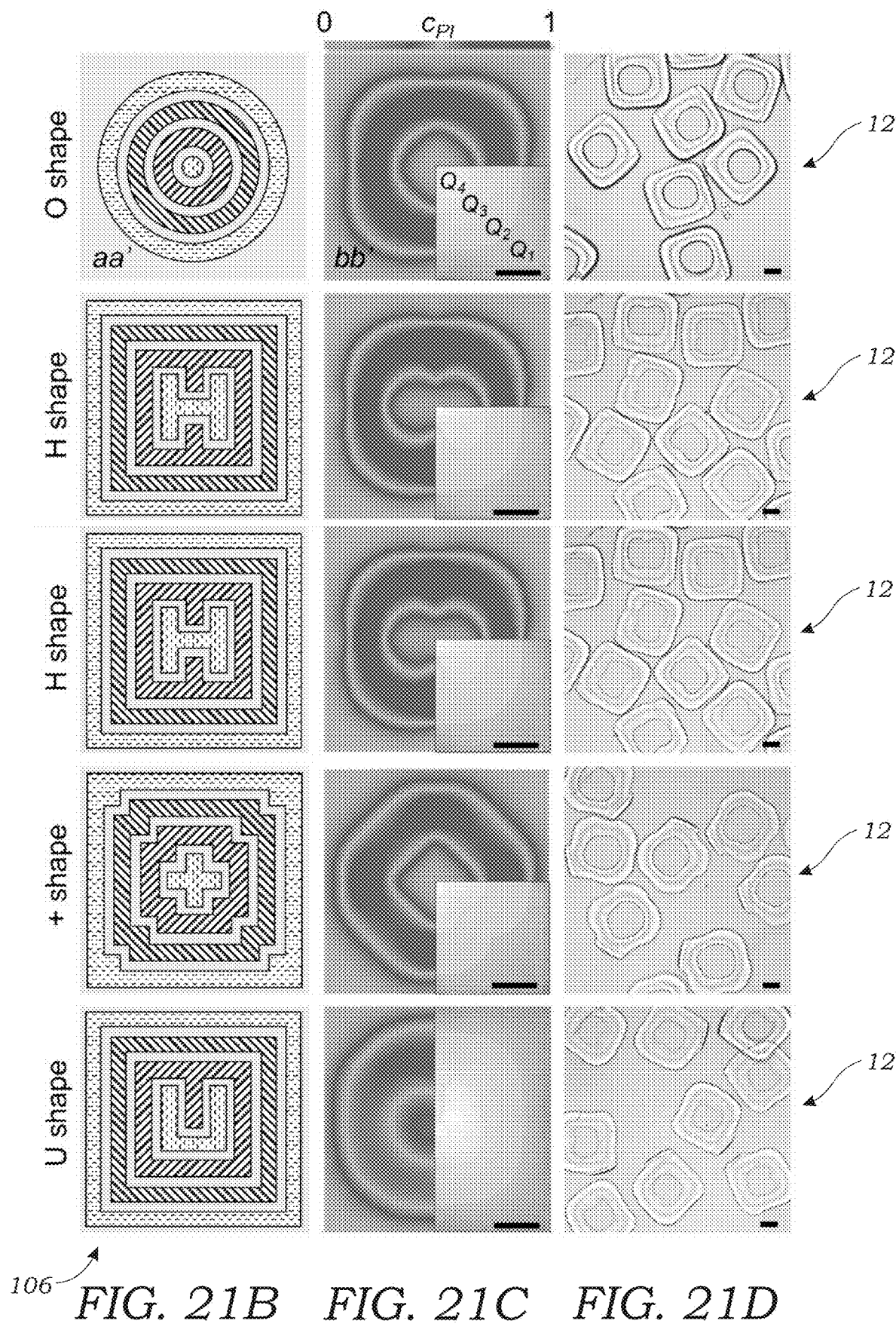
FIG. 21B illustrates different co-axial flow channel cross-sections taken along the line a-a' of FIG. 21A. These include O-shaped (top row), H-shaped (second row), plus (+)-shaped (third row), and U-shaped (bottom row) cross-sections.
FIG. 21C illustrates the heat map results of simulated concentrations of photoinitiator ($C_{PI}$) for flows using COMSOL Multiphysics passing through the correspondingly shaped co-axial channel flow cross-sections (to the left of each image) taken along the downstream line b-b' of FIG. 21A. Laminar fluid flow originates from inlets 1-4 (corresponding to flow Q1-Q4 as shown in FIG. 21A) and diffusion of the photoinitiator (PI) molecules from streams corresponding to Q2 and Q3 to streams Q1 and Q4 predict the shapes of the particles to be fabricated.
FIG. 21D illustrates bright-field microscope images of experimentally fabricated drop-carrier particles corresponding to O-shaped, H-shaped, plus (+)-shaped and U-shaped channel designs. Scale bar is 100 μm.
Figure 21E:
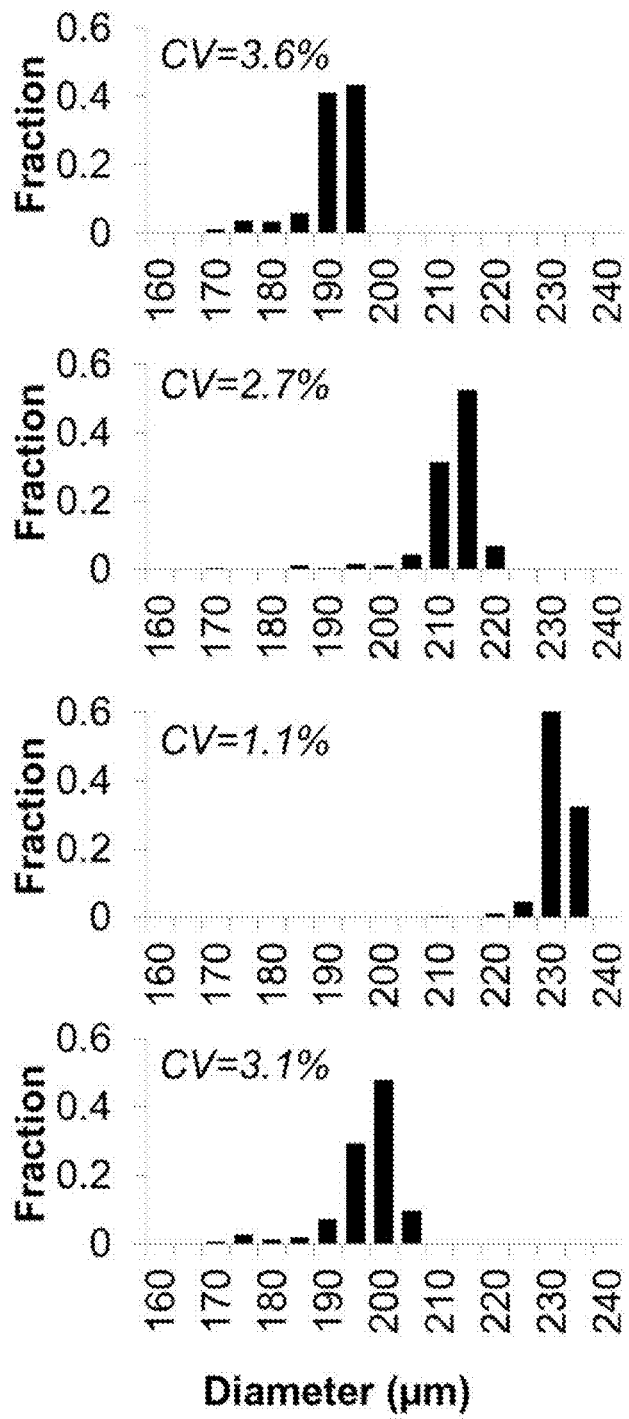
FIG. 21E illustrates histogram plots of the diameter of the inner cavities for each of the drop-carrier particles of FIG. 21D. The histogram plots show uniformity across the drop-carrier particle designs with a CV value of less than 4%.
Figure 21F:
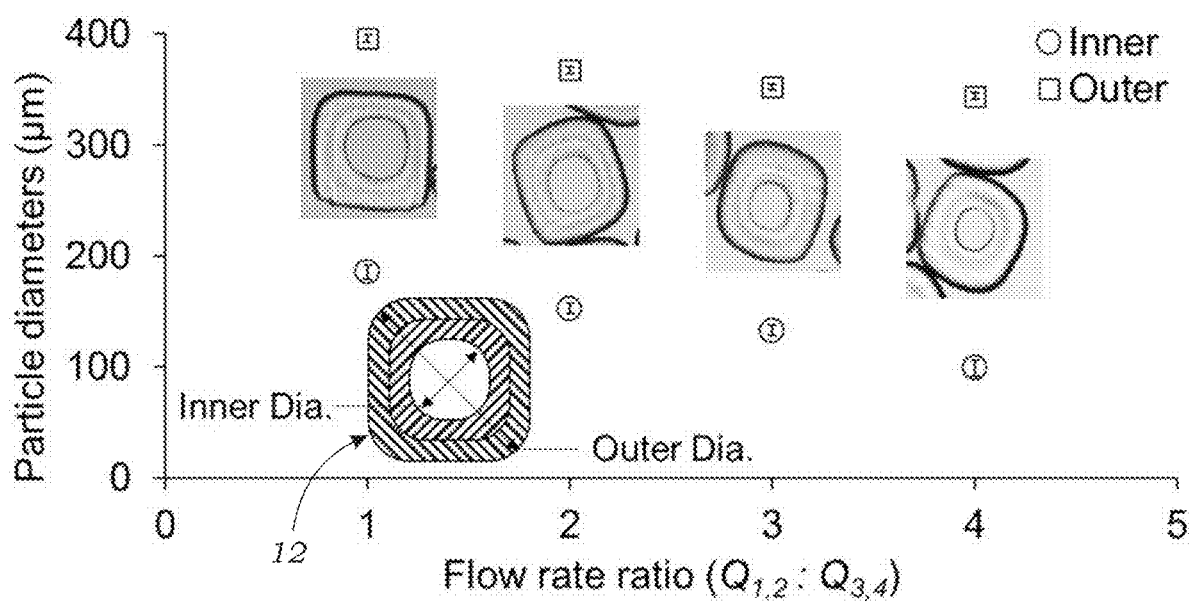
FIG. 21F illustrates inner diameters (circle data point) and outer diameters (square data point) of the O-shapes drop-carrier particles plotted against flow rate ratio ($Q_{1,2}:Q_{3,4}$).

FIG. 20C illustrates a schematic representation of fluid flow that is sculpted using the embodiment of FIG. 20A and FIG. 21A that is exposed to crosslinking illumination (e.g., ultraviolet light) passing through a mask. Various "slices" of this flow is thus crosslinked to generate the drop-carrier particles. A zoomed-in view of the exposure region shows that the co-axial flow streams are exposed to rectangular-shaped UV beams defined by the slit feature 65 size (width 100 μm×length 1,000 μm) in the photo mask 64. The 100 μm width of the UV beam defines the thickness of the polymerized region, whereas the 1000 μm length of the UV beam is enough to cover the whole cross section of the microfluidic channel 104 (e.g., in an experimental embodiment a square glass capillary with the inner and outer dimensions of 500 μm and 700 μm, respectively).

FIG. 20D illustrates a cross-sectional view of an exemplary drop-carrier particle 12 formed from crosslinked poly (propylene glycol) diacrylate (PPGDA) and crosslinked poly(ethylene glycol) diacrylate (PEGDA) that generate amphiphilic drop-carrier particles 12. The flow streams originating from microfluidic channels 2 and 3 are polymerized in the form of a ring-shaped amphiphilic drop-carrier particle 12 with hydrophobic outer region 16 made of PPGDA and hydrophilic inner region 14 made of PEGDA.

FIG. 20E illustrates a fluorescence microscope image (TRITC) (left) and bright-field (right) image of representative experimentally fabricated drop-carrier particles 12. The dashed lines mark the outer boundaries of the drop-carrier particle 12 in the fluorescence microscopy image (left). The plus-shaped drop-carrier particles 12 were incubated with resorufin dissolved in phosphate-buffered saline (PBS) buffer for ~10 min. After washing the excess resorufin away, it is observed that the resorufin has partitioned into the inner PEGDA layer only, thus indicating the presence of multiple-materials within the particle structure as PPGDA layer does not emit any florescent signal. Scale bar is 100 μm.

FIGS. 20F and 20G illustrates a bright-field image of O-shaped drop-carrier particles 12 suspended in ethanol. The batch of fabricated O-shape drop-carrier particles 12 suspended in ethanol shows a high uniformity in the particle size as well as the inner cavity or void 24. Although most of the drop-carrier particles 12 are sitting on the surface facing upward, some of the drop-carrier particles 12 are sitting on their sides that shows uniformity in their thickness as well. The drop-carrier particles 12 collected directly from the microfluidic device 100 after a complete fabrication cycle are initially suspended in a mixture of uncured PEGDA and PPGDA in ethanol. Additional ethanol is added to reduce the overall density of the solution so much so that the drop-carrier particles 12 becomes heavier than the media and are settled on the bottom of the conical sample collection tube. After removing the supernatant, the drop-carrier particles 12 are washed with pure ethanol three times and are stored in ethanol for later experiments. Scale bar is 1 mm mm in FIG. 20F, and 500 μm in FIG. 20G.

FIG. 22A illustrates an exemplary operational workflow for the formation of aqueous droplets 18 inside the cavities or inner voids 24 of drop-carrier particles 12. The drop-carrier particles 12 are initially suspended (and stored) in ethanol as illustrated in operation (1). Next, the drop-carrier particles 12 are transferred to a sample holder (e.g., well plate) where the medium is exchanged to PBS after three washing steps as seen in operation (2). The medium exchange results in swelling of the PEGDA layer (interior region 14) thus reducing the size of the cavity or inner void 24 to some extent. Fluorescein isothiocyanate-biotin (FITC) dissolved in PBS is added to the particles with concentration of 20 μg/ml as seen in operation (3). Once the FITC molecules have been fully dispersed around and inside the cavity or inner void 24 by wetting the hydrophilic inner surface, the excess liquid is removed as seen in operation (4). This leaves a small volume of aqueous phase fluid 18 (e.g., droplet) trapped within the cavity or inner void 24. Poly(dimethylsiloxane-co-diphenylsiloxane) (PSDS) oil 22 is added on top of the drop-carrier particles 12 to secure the encapsulation and compartmentalization of the aqueous phase fluid 18 within the drop-carrier particles 12 by pushing the remaining aqueous phase outside of the drop-carrier particles 12 away from them as seen in operation (5). This completes the formation of the particle-drops 20 where substantially all of the particle-drops 20 include an aqueous drop 18 associated with a single drop-carrier particle 12 surrounded by the oil phase 22 which prevents molecular cross-talk between particle-drops 20. After the oil phase 22 is added, the drop-carrier particles 12 gradually recover back to their original shape.

FIG. 22B illustrates bright-field images (top) and fluorescence images (bottom) of different shaped particle-drops 20 formed from different shaped drop-carrier particles 12 (O-shaped, H-shaped, Plus (+)-shaped, and U-shaped). The bright-field images (top) show the liquid (aqueous) droplets 18 trapped within the cavity or inner void 24 of the solid drop-carrier particles 12, whereas, the fluorescence images (bottom) clearly show the encapsulated volume of fluid 18 of the aqueous phase. Scale bar is 100 μm. FIG. 22C illustrates corresponding histograms of normalized intensity of the encapsulated fluorescent droplets 18 correlated with the volume of the encapsulated fluid 18 within the four differently shaped drop-carrier particles 12 (O-shaped, H-shaped, Plus (+)-shaped, and U-shaped).

Figure 23A:
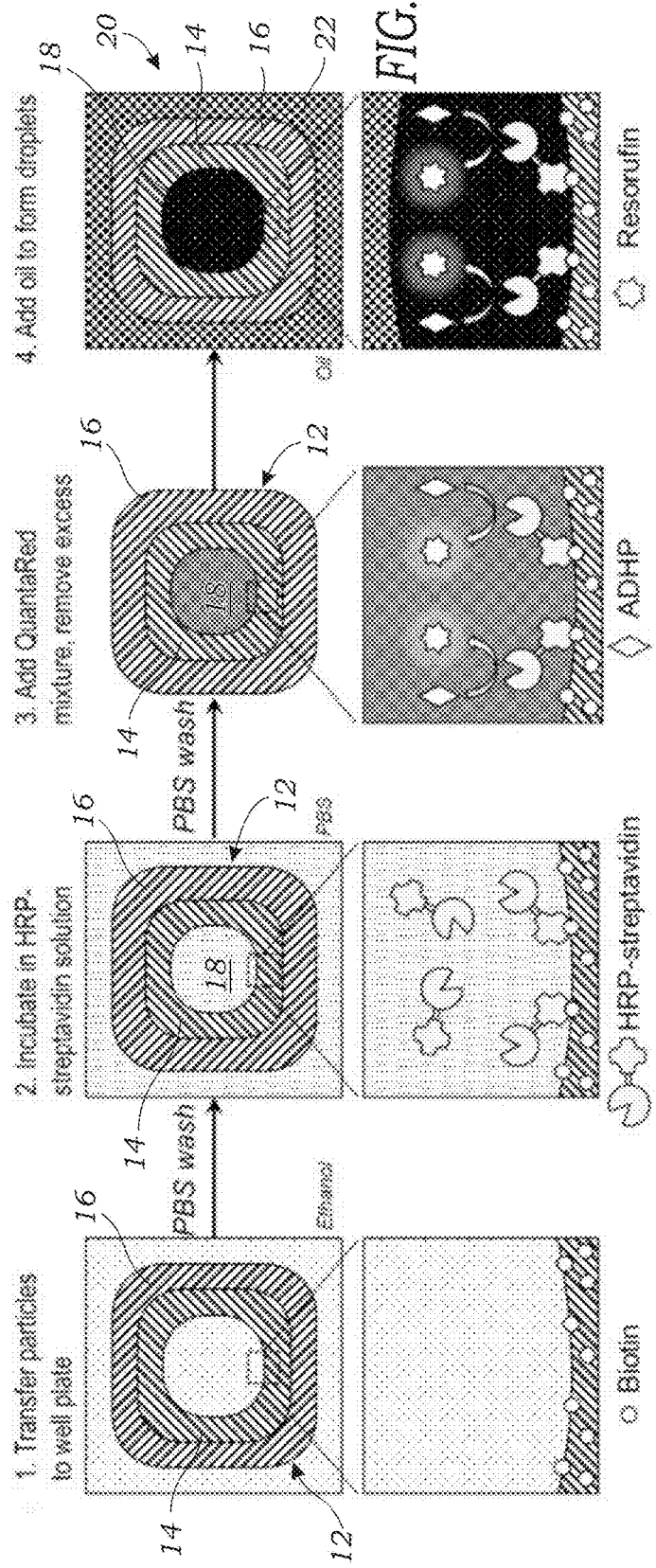
FIG. 23A illustrates an exemplary operational workflow for the use of the particle-drop system for an amplified bioassay in a well plate.
Figure 23B:
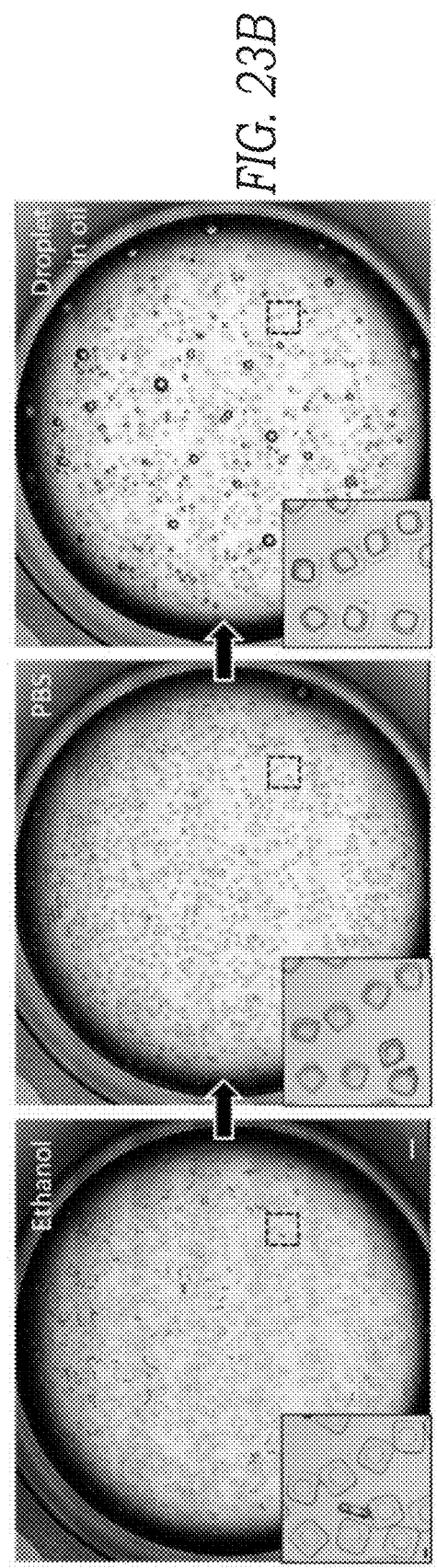
FIG. 23B illustrates bright-field microscopic images of a single well of a well plate at different steps of the assay workflow (FIG. 23A). Images are captured when particles are in ethanol (step 1 of FIG. 23A), PBS (step 2 of FIG. 23A), and PSDS oil (step 4 of FIG. 23A) with particle-drops formed. Inset images demonstrate the particle morphology change by swelling or shrinking in the same field-of-view. The scale bar for the whole well image represents 1 mm, and the scale bar for the inset images represents 100 μm.

FIG. 23A illustrates an exemplary operational workflow for the use of the particle-drop system 10 for an amplified affinity bioassay in a well plate or other sample holder. Drop-carrier particles 12 with biotin incorporated in the inner hydrophilic layer 14 are first added to the well plate suspended in ethanol as seen in operation (1). Once the drop-carrier particles 12 are settled down at the bottom of the well, which has a hydrophobic surface, the drop-carrier particles 12 are washed with PBS with 0.5% Pluronic (PBSP) for three times. Then, 300 μl of HRP-streptavidin solution is added and incubated for 30 min to allow binding of HRP-streptavidin to the biotin in the hydrophilic layer 14 (operation (2) of FIG. 23A), which is followed by washing with PBSP. Next, 500 μl QuantaRed™ solution was mixed and added to the well with excess removed immediately as seen in operation (3). Lastly, 500 μl oil (PSDS) was added to form particle-drops 20, where the ADHP in the QuantaRed™ solution reacts with HRP to produce resorufin, which is a soluble and highly fluorescent reaction product with excitation/emission maxima at ~570/585 nm. For quantification of the assay results, fluorescence and bright-field images of the particle-droplets 20 in oil 22 are obtained using a fluorescence microscope with exposure time of 40 ms. Imaging of the whole well allows the simultaneous monitoring of a few hundreds of independent reactions in compartmentalized particle-drops 20 without cross-talk (e.g. diffusive or other transport of reagents or reaction products) between individual particle-drops 20. FIG. 23B illustrates microscopic images of a single well of a well plate at different steps of the assay workflow (FIG. 23A). Images are captured when particles are in ethanol (step 1 of FIG. 23A), PBS (step 2 of FIG. 23A), and oil (step 4 of FIG. 23A) with particle-droplets 20 formed. Inset images demonstrate the drop-carrier particle 12 morphology change by swelling or shrinking in the same field-of-view.

FIG. 24A illustrates a schematic of two different shaped particles that are used to demonstrate the ability of the particle-drop system 10 to be used for duplex assays with minimal crosstalk between drop-carrier particles 12 over time. Drop-carrier particles 12 that are plus (+)-shaped without biotin in the PEGDA layer 14 are used as a negative control population; H-shaped drop-carrier particles 12 with biotin in PEGDA layer 14 are used as a positive population. These two drop-carrier particles 12 have different shapes of the outer PPGDA layer 16 and inner PEGDA layer 14, therefore shape-coded in both bright-field and fluorescence channels. Both types of drop-carrier particles 12 are mixed with a 1:1 ratio in ethanol and transferred to the same well, washed with PBSP for three times, and incubated in 0.1 nM HRP-streptavidin solution for 30 min. The same QuantaRed™ assay protocol was performed as described in FIG. 23A to quantify the bound HRP-streptavidin.

FIG. 24B illustrates a merged microscopic image of bright-field and TRITC channels at a 60 min timepoint after the reaction started using the drop-carrier particles 12 of FIG. 24A, illustrating contrast in fluorescent signal within the internal aqueous drop 18 of the particle-drops 20 between plus (+)-shaped drop-carrier particles 12 (negative group) and H-shaped drop-carrier particles 12 (positive group), respectively. FIG. 24C illustrates microscopic fluorescence images of the same field of view as in FIG. 24B at three sequential timepoints, i.e., 15, 35 and 60 min following the start of the reaction. FIG. 24D illustrates histograms of fluorescent intensities within the aqueous drop 18 of the particle-drops 20 for a population of particle-drops 20 within a wall at 15, 35 and 60 min, respectively, showing that the signal from plus (+)-shaped drop-carrier particles 12 (negative group) increased at a much slower rate compared to that of H-shaped drop-carrier particles 12 (positive group). FIG. 24E illustrates the average of fluorescent intensity at three timepoints 15, 35, and 60 min for H-shaped drop-carrier particles 12 and plus (+)-shaped drop-carrier particles 12.

FIG. 25A illustrates microscopic images of QuantaRed™ assay results using two O-shaped drop-carrier particle 12 designs at two conditions, i.e., negative control and 1 nM streptavidin HRP. The experimental conditions for fabrication of drop-carrier particles 12 used in these experiment were as follows: (design 1) PI (2-hydroxy-2-methylpropiophenone) concentration of 5%, $\tau_{exp}$=0.3 s, $\tau_s$=4 s, $\tau_d$=1 s, $Q_t$=1 ml/min ($Q_{1,2}$:$Q_{3,4}$=1), particle's thickness defined by the mask width t=200 μm; (design 2) PI concentration of 5%, $\tau_{exp}$=0.3 s, $\tau_s$=2 s, $\tau_d$=1.75 s, $Q_t$=2 ml/min ($Q_{1,2}$: $Q_{3,4}$=1), t=100 μm.

FIGS. 25B and 25C illustrate respective graphs of mean intensity within the aqueous volume 18 within a population of particle-drops 20 after the QuantaRed™ assay. Results are shown for negative controls and different concentrations of streptavidin HRP showing amplified assay performance using biotin-modified drop-carrier particle 12 design 1 (FIG. 25B) and drop-carrier particle 12 design 2 (FIG. 25C). The particle-drop 20 that used drop-carrier particle design 1 exhibits a limit-of-detection (LOD) of 100 fM, and linear range from 1 pM to 1 nM. The particle-drop 20 that used drop-carrier particle design 2 exhibits improved LOD of 10 fM, but narrower linear range from 1 pM to 100 pM. In the negative control group, drop-carrier particles 12 were incubated with PBS only, all the other steps were kept the same as positive groups as described in FIG. 23A.

FIG. 25D illustrates a graph of intensity for the negative controls and different concentrations of streptavidin-Alexa Fluor® 568 showing assay performance without amplification using direct fluorescent labeling of streptavidin. Drop-carrier particles 12 with design 2 were transferred to well plate and washed in the same manner as (FIG. 25C), followed by incubation with streptavidin-Alexa Fluor® 568 for 30 min, then washed 3 times in PBSP. Next, particle-drops 20 were formed in PBS with oil 22 added. In the negative control group, drop-carrier particles 12 were incubated with PBS only, all the other steps were kept the same as positive groups. Fluorescence images were obtained in the same manner as QuantaRed™ assay with 40 ms exposure time. Fluorescent (TRITC) signal remained in the particle-drops 20 based on the formation of biotin-streptavidin-Alexa Fluor® 568 complexes on the surface of the drop-carrier particles 12. These results show that signals generated in particle-drops 20 using fluorescent labeling without amplification are much weaker (requires at least 1 nM streptavidin) compared to amplified cases using the same particles (10 fM streptavidin), which is equivalent to 5 orders of magnitude improvement. This comparison (between FIGS. 25C and 25D) highlights the significance of including the amplification operation(s) in compartmentalized nanoliter fluid volume 18 contained within the particle-drops 20 for enhanced assay performance.

FIGS. 26A-26D illustrate how the size of the interior region 14 of drop-carrier particles 12 (and the volume of the cavity or inner void 24) can be adjusted or tuned with changing flow rate conditions during their formation. With reference to FIG. 26A, the size of the cavity or void 24 in the O-shaped drop-carrier particle 12 decreased gradually as the flow rate ratio ($Q_1$:$Q_{2-4}$) increased from 2 to 10. The experimental conditions were as follows: PI concentration of 2-hydroxy-2-methylpropiophenone 5%, $\tau_{exp}$=0.3 s, $\tau_s$=5 s, $\tau_d$=1 s, and $Q_t$=1.25, 1.45, 1.65, 1.6, 1.3 ml/min corresponding to each data point in the plot. With reference to FIG. 26B, the size of the cavity or void 24 in the H-shaped drop-carrier particle 12 decreased gradually as the flow rate ratio ($Q_{1-3}$:$Q_4$) increased from 0.74 to 1.75. The experimental conditions were as follows: PI (same as above) concentration of 5%, $\tau_{exp}$=0.5 s, $\tau_s$=4 s, $\tau_d$=2.25 s, and $Q_t$=1 ml/min for all the measurements. With reference to FIG. 26C, the size of the cavity or void 24 in the plus (+)-shaped drop-carrier particle 12 decreased gradually as the flow rate ratio ($Q_{1,2}$:$Q_{3,4}$) increased from 1 to 4. The experimental conditions were as follows: PI (same as above) concentration of 5%, $\tau_{exp}$=0.3 s, $\tau_s$=4 s, $\tau_d$=1, 1.25, 1.5, 1.75 s, and $Q_t$=0.6, 0.9, 1.2, 1.5 ml/min, respectively, for the corresponding measurements. With reference to FIG. 26D, the size of the cavity or void 24 in the U-shaped drop-carrier particle 12 decreased gradually as the flow rate ratio ($Q_{1,3}$: $Q_{2,4}$) increased from 1 to 4. The experimental conditions were as follows: PI concentration of 2 and 4% 2-hydroxy-2-methylpropiophenone in PPGDA and PEGDA, respectively, $\tau_{exp}$=0.5 s, $\tau_s$=5 s, $\tau_d$=1 s, and $Q_t$=1.2, 1.4, 1.6 ml/min, for the corresponding measurements. Thus, varying flow rate conditions of the precursor materials may be used to control the dimensions of the drop-carrier particles 12 including the volume size of the cavity or inner void 24.

FIGS. 27A-27C illustrates results for the intensity changes within the aqueous volume 18 of particle-drops 20 over time when conducting the assay as illustrated in FIG. 23A following the addition of QuantaRed™ reagents and encapsulation in oil 22 to form particle-drops 20. FIG. 27A shows the mean intensity changes over time for a population of particle-drops 20 with error bars representing standard error of the mean. Results for streptavidin HRP concentrations of 10 pM, 100 fM, and a control group using particle-drops 20 incubated with PBS only without HRP are shown. FIG. 27B and FIG. 27C show corresponding intensity changes present within the aqueous volume 18 of individual particle-drops 20 for streptavidin HRP concentrations of 100 fM (FIG. 27B) and 10 pM (FIG. 27C). The aggregated signal of multiple particle-drops 20 leads to a less noisy and more accurate readout of concentration compared to a single reaction within a single particle-drop 20. The time for signal recording starts at 10 minutes following the addition of QuantaRed™ reagents, since the oil phase 22 is added and focusing is performed using a microscope for imaging. An initial dip in intensity can be attributed to the change in shape of the drop-carrier particle 12 upon the change of reagents (e.g., aqueous phase and oil 22) during the process of forming particle-drops 20 as shown in FIG. 23B.

Figure 28:
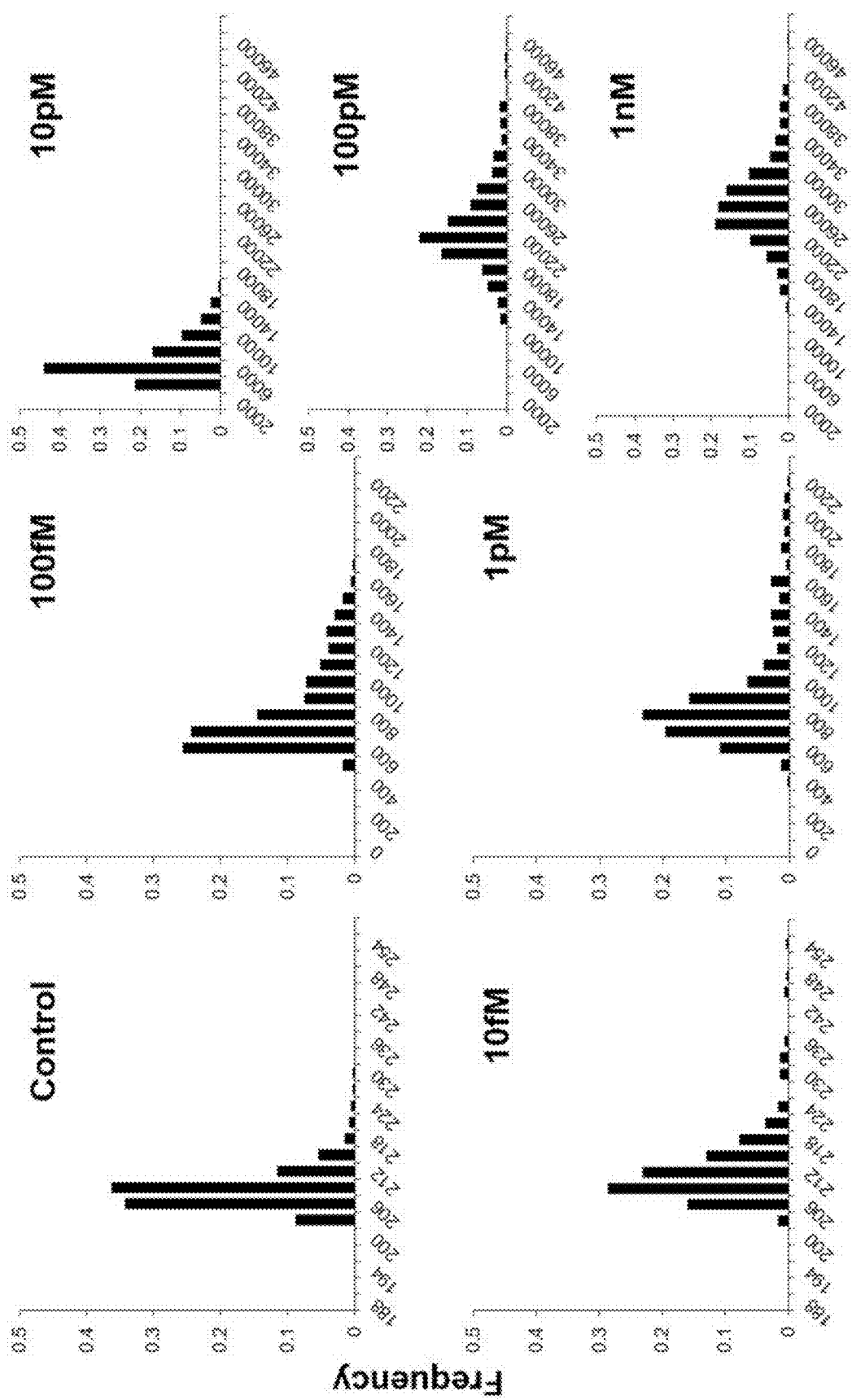
FIG. 28 illustrates histograms of intensity after 45 min within the aqueous volumes in the voids of particle-drops as a function of streptavidin HRP concentration for the amplified assay using QuantaRed™ according to the assay workflow in FIG. 23A. The results are shown for O-shaped drop-carrier particle design 2, which correlates with the results reported as mean intensity in FIG. 25C.

FIG. 28 illustrates histograms of fluorescence intensity within the aqueous volume 18 of a population of particle-drops 20 when performing the assay as illustrated in FIG. 23A using O-shaped drop-carrier particles 12. Different concentrations streptavidin-HRP are illustrated which correlates with the results from FIG. 25C. The results demonstrate that the assay protocol using the particle-drop system 10 provides ease of implementation with existing amplified assay workflows, enabling hundreds to thousands of parallel reactions. Compiling a readout from a "swarm" of large numbers of these particle-drops 20 by imaging reduces random error due to increased sample size (i.e., number of particle-drops 20), therefore enhances the accuracy of the detection without jeopardizing detection practicality.

Figure 29:
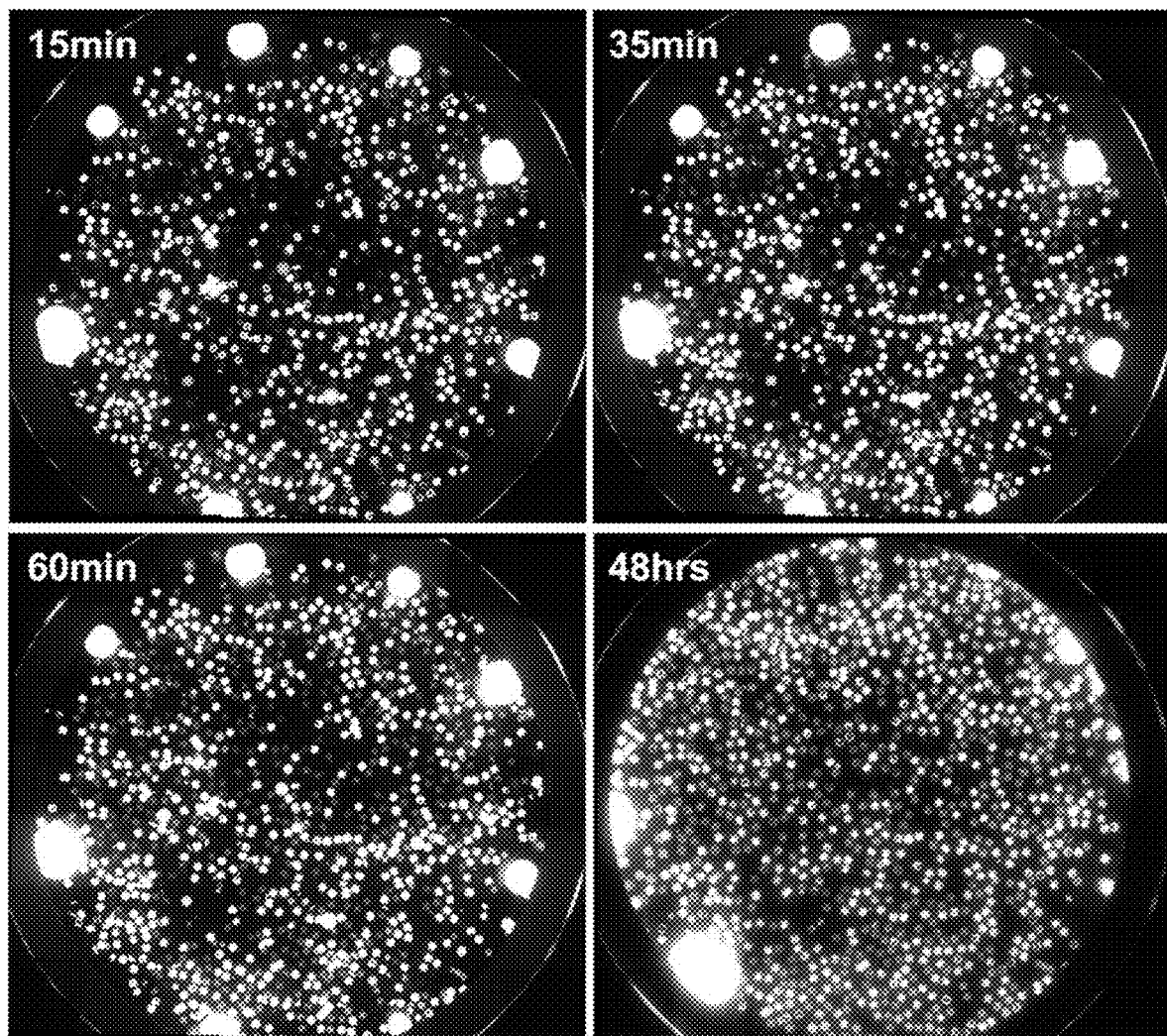
FIG. 29 illustrates fluorescence microscope images of fluorescent particle-drops with drop-carrier particles of two shapes following the same protocol (QuantaRed™) as shown in FIG. 23A. A duplex assay is performed as shown in FIG. 24A where plus (+)-shaped particles are negative/contain no biotin and H-shaped particles are positive/contain biotin and can bind streptavidin HRP. Particles were incubated with 0.1 nM streptavidin HRP. A single well of a well plate at different times (15 min, 35 min, 60 min, 48 hours) after reaction initiation are shown. The images show the ability to perform a duplex assay with shape-coded drop-carrier particles demonstrating minimum crosstalk over time. At 48 hrs, some of the compartmentalized fluid volumes within the drop-carrier particles are partially evaporated but the signal between particle-drop populations with negative and positive signals remain to be noticeably different.

It should be appreciated that the particle-drop system 10 also permits duplex or multiplex (3+) assays to be performed as there is little crosstalk between particle-drops 20 over time. FIG. 29, for example, illustrates a fluorescence microscopic image showing the same well at 15 min, 35 min, 60 min, and 48 hrs after reaction. At 48 hrs, some of the aqueous fluid volumes 18 of the particle-drops 20 are partially evaporated but the signal between particle-drop 20 populations with negative and positive particle-drops 20 remain noticeably different even after the passage of significant time.

While embodiments of the present invention have been shown and described, various modifications may be made without departing from the scope of the present invention. The invention, therefore, should not be limited, except to the following claims, and their equivalents.

What is claimed is:

1. A method of simultaneously forming a plurality of droplets, the method comprising:

forming a suspension comprising a plurality of cells, a plurality of particles and an oil phase by combining the plurality of cells, the plurality of particles and the oil phase, wherein each particle of the plurality of particles has a first characteristic diameter; and simultaneously forming the plurality of droplets by mixing the suspension such that the plurality of droplets comprises a subset of droplets wherein each droplet of the subset of droplets has a second characteristic diameter and comprises not more than a single particle and not more than a single cell, and wherein the second characteristic diameter of each droplet of the subset of droplets is defined by the first characteristic diameter of each single particle of each corresponding droplet of the subset of droplets.

2. The method of claim 1, wherein each particle of the plurality of particles comprises a barcode.

3. The method of claim 2, wherein each barcode of each particle is a nucleic acid barcode.

4. The method of claim 2, wherein each barcode of each particle is unique for each particle of the plurality of particles.

5. The method of claim 4, wherein the barcode of each particle comprises a plurality of identical barcodes.

6. The method of claim 2, further comprising generating released nucleic acid molecules by releasing nucleic acid molecules from at least one single cell.

7. The method of claim 6, wherein the releasing nucleic acid molecules from at least one single cell comprises lysing the at least one single cell.

8. The method of claim 6, further comprising associating the released nucleic acid molecules with a respective barcode in a respective droplet.

9. The method of claim 8, wherein the released nucleic acid molecules comprise mRNA molecules.

10. The method of claim 9, wherein the barcode comprises a poly-T sequence to capture the mRNA molecules.

11. The method of claim 9, further comprising forming cDNA molecules by reverse transcribing the mRNA molecules.

12. The method of claim 11, wherein the cDNA molecules comprise a barcoded nucleic acid sequence corresponding to the respective barcode.

13. The method of claim 11, further comprising forming amplified cDNA molecules by amplifying the cDNA molecules.

14. The method of claim 13, further comprising generating sequencing reads by sequencing the amplified cDNA molecules.

15. The method of claim 14, further comprising, prior to the sequencing, pooling mRNA molecules from different single cells, or CDNA molecules or amplified cDNA molecules generated therefrom, wherein the mRNA molecules from different single cells, or the cDNA molecules or the amplified cDNA molecules generated therefrom are associated with different barcodes.

16. The method of claim 15, further comprising assigning a cell of origin to the mRNA molecules based on a particular barcode of the different barcodes.

17. The method of claim 1, wherein each particle of the plurality of particles comprises a hydrogel.

18. The method of claim 17, wherein the hydrogel comprises a polyethylene glycol (PEG) hydrogel or a poly (ethylene glycol) diacrylate (PEGDA) hydrogel.

19. The method of claim 1, wherein the mixing comprises vortexing the suspension.

* * * * *